(12) United States Patent
Ohkura et al.

(10) Patent No.: US 6,417,362 B1
(45) Date of Patent: Jul. 9, 2002

(54) NITROGENOUS HETEROCYCLIC COMPOUNDS AND HYPERLIPEMIA REMEDY CONTAINING THE SAME

(75) Inventors: Naoto Ohkura; Takashi Tsuruoka; Takayuki Usui; Yukiko Hiraiwa; Tetsuya Matsushima; Masaharu Shiotani; Tetsutaro Niizato; Yuuko Nakatani; Shigeki Suzuki; Chidsuko Kuroda; Kiyoaki Katano, all of Yokohama (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 0 days.

(21) Appl. No.: 09/424,708

(22) PCT Filed: Jun. 1, 1998

(86) PCT No.: PCT/JP98/02411
§ 371 (c)(1),
(2), (4) Date: Nov. 30, 1999

(87) PCT Pub. No.: WO98/54135
PCT Pub. Date: Dec. 3, 1998

(30) Foreign Application Priority Data

May 30, 1997 (JP) ............................................ 9-141410

(51) Int. Cl.[7] .................... C07D 241/04; C07D 217/00; C07D 217/22; A61K 31/495; A61K 31/50

(52) U.S. Cl. ....................... 544/358; 544/373; 544/363; 514/252.12; 514/252.13; 514/253.05; 514/307; 514/313; 514/314; 546/141; 546/143; 546/146; 546/149; 546/151

(58) Field of Search ................... 514/252.12, 252.13, 514/253.05, 307, 313, 314; 546/141, 143, 146, 149, 151; 544/363, 358, 373

(56) References Cited

FOREIGN PATENT DOCUMENTS

| EP | 0 643 057 | 3/1995 |
| WO | 96/26187 | 8/1996 |
| WO | 9626187 | * 8/1996 |
| WO | 98/00134 | 1/1998 |

OTHER PUBLICATIONS

Hutchinson et al., "Non–Peptide Glycoprotein llb/llla Antagonists. 11. Design and in Vivo Evaluation of 3,4–Dihydro–1 (1H)–isoquinolinone–Based Antagonists and Ethyl Ester Prodrugs", J. Med. Chem. 1996, 39, 4583–4591.

Prueksaritanont et al., "In Vitro and In Vivo Evaluations of the Metabolism, Pharmacokinetics, and Bioavailability of Ester Prodrugs of L–767,679, A Potent Fibrinogen Receptor Antagonist", Drug Metabolism and Disposition, vol. 25, No. 8, 1997, pp. 978–984.

Prueksaritanont et al., "Analysis of Metabolite Kinetics by Deconvolution and In Vivo–In Vitro Correlations of Metabolite Formation Rates: Studies of Fibrinogen Receptor Antagonist Ester Prodrugs", Journal of Pharmaceutical Sciences, vol. 86, No. 12, Dec. 1997, pp. 1345–1351.

* cited by examiner

Primary Examiner—Mukund J. Shah
Assistant Examiner—Sudhaker B. Patel
(74) Attorney, Agent, or Firm—Wenderoth, Lind & Ponack, L.L.P.

(57) ABSTRACT

Disclosed are compounds represented by formula (I) and pharmaceutically acceptable salts and solvates thereof. The compounds can inhibit the biosynthesis of triglycerides in the liver and can inhibit the secretion of lipoprotein containing apolipoprotein B from the liver. Therefore, they are useful for the prevention or treatment of hyperlipidemia (particularly hyper-very-low-density-lipoproteinemia) and arteriosclerotic diseases, such as cardiac infarction, or pancreatitis induced by hyperlipidemia.

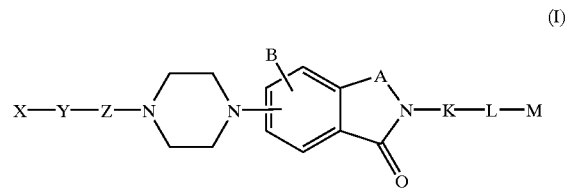

(I)

wherein A represents group —$CR^1R^2$—$(CH_2)_i$— where $R^1$ and $R^2$ each represent a hydrogen atom or alkyl, —CH=CH—, —O—$CH_2$—, or —S(O)$_j$—$CH_2$—; B represents a hydrogen or halogen atom; X represents —$CR^3R^4R^5$, —$NR^6R^7$, —($CH_2$—CH=C($CH_3$)—$CH_2$)$_p$—$CH_2$CH=C($CH_3$)$_2$, alkyl, cycloalkyl, phenyl, cinnamyl, or heteroaromatic ring; Y represents —($CH_2$)$_q$—, —CH=CH—, —$NR^8$—, an oxygen atom, or a bond; Z represents carbonyl or a bond; K represents alkylene or a bond; L represents —CH=CH— or a bond; and M represents a hydrogen atom, alkyl, cycloalkyl, phenyl, heterocyclic ring, biphenyl, or diphenylmethyl.

11 Claims, No Drawings

NITROGENOUS HETEROCYCLIC COMPOUNDS AND HYPERLIPEMIA REMEDY CONTAINING THE SAME

This application is a 371 application of PCT/JP98/02411 filed Jun. 1, 1998.

BACKGROUND OF THE INVENTION

1. Field of the Invention

The present invention relates to compounds having inhibitory activity against the biosynthesis of triglycerides and inhibitory activity against the secretion of lipoprotein containing apolipoprotein B, and prophylactic or therapeutic agents for hyperlipidemia comprising the same.

2. Background Art

A change in eating habits and an increase in the aged population have resulted in increased arteriosclerotic diseases. One of major risk factors of this group of diseases is an abnormal increase in cholesterol or triglycerides (hyperlipidemia). For example, the proportion of familial composite hyperlipidemia (FCHL) in patients suffering from cardiac infarction is about 30% which is higher than other basal diseases, and hyperlipidemia is known to be a basal disease which has a high risk of onset of ischemic heart disease (Lipid, 2, 373 (1991)).

Further, hyperlipidemia, which is a complication of obesity or diabetes, has been recognized as a risk factor of arteriosclerosis (Diabetes, 37, 1595(1988) and Int. J. Obesity, 15, 1 (1991)).

Among various types of hyperlipidemia, hypertriglyceridemia is known to involve a complication of pancreatitis or the like (Medical Practice, 12, 957 (1995)).

Therefore, the treatment of hyperlipidemia is important for the prevention or treatment of arteriosclerotic diseases, such as ischemic heart diseases and cerebrovascular diseases, or pancreatitis. Further, it has been pointed out that there is a possibility that hyperlipidemia involved in renal diseases progresses renal disorders (Molecular Medicine, 31, 536 (1994)). This has led to a proposal on the necessity of treating hyperlipidemia.

For the treatment or prevention of hyperlipidemia and arteriosclerotic diseases, medicaments for inhibiting the biosynthesis of cholesterol, particularly statin compounds (such as lovastatin) as medicaments for inhibiting 3-hydroxy-3-methylglutaryl-coenzyme A reductase and fibrate compounds (such as bezafibrate) as medicaments for reducing the level of triglycerides have been clinically used as pharmaceuticals.

Further, in recent years, reducing the serum triglyceride value and the level of serum apolipoprotein B-containing lipoprotein, which has been considered to induce arteriosclerosis, is expected to be effective in preventing or treating the above diseases (Arterioscler. Thromb., 12, 1284 (1992) and Circulation, 85, 37 (1992)). One of bases for this is that artoriosclerosis is not developed in patients suffering from β-alipoproteinemia, from whom apolipoprotein B-containing lipoprotein is not detected in blood (Clin. Chem., 34, B9-12 (1988).

Pyrrolecarboxylic acid derivatives, sulfonamide derivatives, biphenyl-2-carboxylic acid derivatives, phenylpiperazine derivatives and the like are known as compounds having the above activity. Further, isoindolone derivatives having a substituent only in their nitrogen atom at the 2-position are known (EP643057A1 and WO96/26205).

On the other hand, compounds having piperazine on the benzene in the isoindolone and isoquinolone skeletons are known (WO96/26187). These compounds, however, are different from the compounds of the present invention in the substituent of nitrogen at the 2-position, and, in addition, have activity as fibrinogen receptor antagonist. Therefore, they and the present invention are different form each other in idea.

So far as the present inventors know, compounds having inhibitory activity against the secretion of apolipoprotein B-containing lipoprotein among the compounds having piperazine on the benzene ring in the isoindolone and isoquinoline skeletons are not known.

Accordingly, the development of medicaments, which have activity to reduce the level of serum triglycerides and, based on a novel mechanism of action, activity to reduce the level of apolipoprotein B-containing lipoprotein in blood and, at the same time, do not cause any side effect of the accumulation of lipid such as found in β-alipoproteinemia within the liver, have been desired for use of these medicaments as prophylactic or therapeutic agents for hyperlipidemia or arteriosclerotic diseases (The Metabolic Basis of Inherited Disease, Sixth edition, 1139 (1989)).

SUMMARY OF THE INVENTION

The present inventors have now found that novel nitrogen-containing heterocyclic compounds having piperazine on a benzene ring of isoindolone and isoquinolone skeletons or skeletons similar thereto have high activity to reduce the level of lipid in blood, particularly high activity to reduce the level of triglycerides in blood and high activity to reduce the level of lipoprotein containing apolipoprotein B in blood by virtue of inhibitory activity against the biosynthesis of triglycerides and inhibitory activity against the secretion of lipoprotein containing apolipoprotein B in the liver, and thus are useful as therapeutic and prophylactic agents for hyperlipidemia, arteriosclerotic diseases, and pancreatitis.

Thus, according to the present invention, there is provided a compound represented by formula (I) and pharmaceutically acceptable salt and solvate thereof:

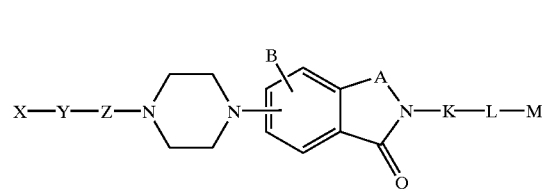

(I)

wherein

A represents group —$CR^1R^2$—$(CH_2)_i$— wherein $R^1$ and $R^2$, which may be the same or different, each represent a hydrogen atom or alkyl having 1 to 6 carbon atoms and i is an integer of 0 or 1,

—CH=CH—,

—O—$CH_2$—, or

—$S(O)_j$—$CH_2$— wherein j is an integer of 0 to 2;

B represents a hydrogen or halogen atom;

X represents

—$CR^3R^4R^5$ wherein $R^3$, $R^4$, and $R^5$, which may be the same or different, each represent a hydrogen atom or phenyl, provided that any one of $R^3$, $R^4$, and $R^5$ represents phenyl and one or more hydrogen atoms on phenyl may be substituted by a halogen atom, hydroxy, nitro, phenyl, or alkoxy having 1 to 6 carbon atoms, —$NR^6R^7$ wherein $R^6$ and $R^7$, which may be the same or different, each represent a hydrogen atom, phenyl, or benzyl, —$(CH_2—CH=C(CH_3)—CH_2)_p—CH_2CH=C(CH_3)_2$ wherein p is an integer of 0 to 2, alkyl having 1 to 18 carbon atoms, cycloalkyl having 3 to 8 carbon atoms, optionally substituted phenyl, optionally substituted cinnamyl, or a five- or six-membered heteroaromatic ring containing up to two hetero atoms;

Y represents —$(CH_2)_q$— wherein q is an integer of 1 to 6,

—CH=CH—,

—$NR^8$— wherein $R^8$ represents a hydrogen atom or alkyl having 1 to 6 carbon atoms, an oxygen atom, or a bond;

Z represents carbonyl or a bond;

K represents optionally substituted alkylene having 1 to 6 carbon atoms or a bond;

L represents —CH=CH— or a bond; and

M represents a hydrogen atom, optionally substituted alkyl having 1 to 6 carbon atoms, optionally substituted cycloalkyl having 3 to 8 carbon atoms, optionally substituted phenyl, optionally substituted five- or six-membered, saturated or unsaturated heterocyclic ring containing up to two hetero atoms, optionally substituted biphenyl, or optionally substituted diphenylmethyl.

The compounds represented by formula (I) according to the present invention inhibit the biosynthesis of triglycerides in the liver and inhibit the secretion of lipoprotein containing apolipoprotein B from the liver. Therefore, they can exhibit activity to reduce the level of serum triglycerides and activity to reduce the level of lipoprotein containing apolipoprotein B in blood and, at the same time, can prevent accumulation of lipid within hepatic cells.

Accordingly, the compounds represented by formula (I) and pharmacologically acceptable salts and solvates thereof according to the present invention are useful for the prevention or treatment of hyperlipidemia (particularly hyper-very-low-density-lipoproteinemia) and arteriosclerotic diseases, such as cardiac infarction, or pancreatitis induced by hyperlipidemia.

DETAILED DESCRIPTION OF THE INVENTION

Definition

As used herein, the term "alkyl" or "alkoxy" as a group or a part of a group means a straight chain or branched chain alkyl. The term "halogen" used herein means fluorine, chlorine, bromine, or iodine. The term "hetero atom" used herein means a nitrogen, oxygen, or sulfur atom.

Compounds represented by formula (I)

In formula (I), A represents —$CR^1R^2—(CH_2)_i$— wherein $R^1$ and $R^2$, which may be the same or different, each represent a hydrogen atom or alkyl having 1 to 6 carbon atoms and i is an integer of 0 or 1; —CH=CH—; —O—$CH_2$—; or —$S(O)_j$—$CH_2$— wherein j is an integer of 0 to 2. Preferably, A represents —$CH_2$— or —$CH_2CH_2$—.

In formula (I), B represents a hydrogen or halogen atom, preferably a hydrogen, fluorine, or chlorine atom.

X represents

—$CR^3R^4R^5$ wherein $R^3$, $R^4$, and $R^5$, which may be the same or different, each represent a hydrogen atom or phenyl, provided that any one of $R^3$, $R^4$, and $R^5$ represents phenyl and one or more hydrogen atoms on phenyl may be substituted by a halogen atom, hydroxy, nitro, phenyl, or alkoxy having 1 to 6 carbon atoms;

—$NR^6R^7$ wherein $R^6$ and $R^7$, which may be the same or different, each represent a hydrogen atom, phenyl or benzyl;

—$(CH_2—CH=C(CH_3)—CH_2)_p—CH_2CH=C(CH_3)_2$ wherein p is an integer 0 to 2;

alkyl having 1 to 18 carbon atoms;

cycloalkyl having 3 to 8 carbon atoms;

optionally substituted phenyl;

optionally substituted cinnamyl; or a five- or six-membered aromatic ring having up to two hetero atoms.

Preferred examples of group —$CR^3R^4R^5$ represented by X include those wherein one or two of $R^3$, $R^4$, and $R^5$ represent phenyl with the remaining one representing a hydrogen atom and the phenyl may be unsubstituted, or alternatively one hydrogen atom on the phenyl may be substituted by a fluorine or chlorine atom.

Preferred examples of group —$NR^6R^7$ represented by X include those wherein $R^6$ and $R^7$ each represent phenyl or benzyl.

Preferred examples of group —$(CH_2—CH=C(CH_3)—CH_2)_p—CH_2CH=C(CH_3)_2$ represented by X include those wherein p is 1 or 2.

The alkyl having 1 to 18 carbon atoms represented by X is preferably alkyl having 1 to 12 carbon atoms, more preferably alkyl having 1 to 6 carbon atoms.

The cycloalkyl having 3 to 8 carbon atoms represented by X is preferably cycloalkyl having 3 to 7 carbon atoms, and preferred examples thereof include cyclopropyl, cyclobutyl, cyclopentyl, cyclohexyl, and cycloheptyl.

One or more hydrogen atoms on phenyl represented by X may be substituted, and an example of substituents usable herein is a group selected from the group consisting of hydroxy, halogens (preferably fluorine, chlorine, and bromine) atoms, nitro, alkoxys having 1 to 6 carbon atoms (preferably methoxy and ethoxy), and phenyl. When there are a plurality of substituents, they may be the same or different.

One or more hydrogen atoms on cinnamyl represented by X may be substituted, and an example of substituents usable herein is a group selected from the group consisting of hydroxy, halogens (preferably fluorine, chlorine, and bromine) atoms, nitro, phenyl, and alkoxys having 1 to 6 carbon atoms (preferably methoxy and ethoxy). When there are a plurality of substituents, they may be the same or different.

An example of preferred five- or six-membered heteroaromatic rings containing up to two hetero atoms represented by X is a ring selected from the group consisting of pyridine, thiophene, pyrrole, furan, pyrazole, imidazole, oxazole, thiazole, pyran, pyridazine, pyrimidine, and pyrazine. More preferred examples thereof include pyridine, thiophene, furan, imidazole, oxazole, and thiazole.

In formula (I), Y represents —(CH$_2$)$_q$— wherein q is an integer of 1 to 6; —CH═CH—; NR$^8$— wherein R$^8$ represents a hydrogen atom or alkyl having 1 to 6 carbon atoms, an oxygen atom, or a bond. Preferably, Y represents —(CH$_2$)$_q$— wherein q is an integer of 1 to 6; —NH—; an oxygen atom, or a bond.

Z represents carbonyl or a bond.

In formula (I), K represents an optionally substituted alkylene having 1 to 6 carbon atoms or a bond, preferably an optionally substituted alkylene having 1 to 3 carbon atoms or a bond.

One or more hydrogen atoms on the alkylene may be substituted, and an examples of substituents usable herein is a group selected from the group consisting of hydroxy, halogens (preferably fluorine, chlorine, and bromine) atoms, alkyl having 1 to 6 carbon atoms, and alkoxys having 1 to 6 carbon atoms (preferably methoxy and ethoxy). When there are a plurality of substituents, they may be the same or different.

L represents —CH═CH— or a bond.

M represents a hydrogen atom, alkyl having 1 to 6 carbon atoms, cycloalkyl having 3 to 8 carbon atoms, phenyl, a five- or six-membered heterocyclic ring containing up to two hetero atoms, biphenyl, or diphenylmethyl, preferably a hydrogen atom, cycloalkyl having 3 to 8 carbon atoms, phenyl, five- or six-membered, saturated or unsaturated heterocyclic ring containing up to two hetero atoms.

One or more hydrogen atoms on the alkyl represented by M may be substituted, and an example of substituents usable herein is a group selected from the group consisting of hydroxyl, halogens (preferably fluorine, chlorine, and bromine) atoms, amino, alkoxys having 1 to 6 carbon atoms (preferably methoxy and ethoxy), and alkoxycarbonyls having 1 to 4 carbon atoms (preferably methoxycarbonyl and ethoxycarbonyl). When there are a plurality of substituents, they may be the same or different.

One or more hydrogen atoms on the cycloalkyl having 3 to 8 carbon atoms represented by M may be substituted, and an example of substituents usable herein is a group selected from the group consisting of hydroxy, halogens (preferably fluorine, chlorine, and bromine) atoms, amino, alkoxys having 1 to 6 carbon atoms (preferably methoxy and ethoxy), alkylcarbonyloxys having 1 to 4 carbon atoms (preferably acetoxy and ethylcarbonyloxy), and alkoxycarbonyls having 1 to 4 carbon atoms (preferably, methoxycarbonyl and ethoxycarbonyl). When there are a plurality of substituents, they may be the same or different.

One or more hydrogen atoms on the benzene ring having phenyl, biphenyl, or diphenylmethyl represented by M may be substituted, and an example of substituents usable herein is a group selected from the group consisting of alkyls having 1 to 4 carbon atoms, trifluoromethyl, nitro, hydroxyl, halogens (preferably fluorine, chlorine, and bromine) atoms, amino, alkoxys having 1 to 4 carbon atoms (preferably methoxy and ethoxy), alkylcarbonyls having 1 to 4 carbon atoms (preferaby acetyl and ethylcarbonyl), and alkoxycarbonyls having 1 to 4 carbon atoms (preferably methoxycarbonyl and ethoxycarbonyl). When there are a plurality of substituents, they may be the same or different.

An example of five- or six-membered, saturated or unsaturated heterocyclic rings containing up to two hetero atoms represented by M is a ring selected from the group consisting of pyridine, thiophene, pyrrole, furan, pyrazole, imidazole, oxazole, thiazole, pyran, pyridazine, pyrimidine, pyrazine, and oxane. Preferred examples thereof include pyridine, thiophene, furan, imidazole, oxazole, thiazole, and oxane. One or more hydrogen atoms on the heterocyclic ring represented by M may be substituted, and examples of substituents usable herein include alkyls having 1 to 4 carbon atoms. When there are a plurality of substituents, they may be the same or different.

Examples of preferred groups represented by formula X-Y-Z- include (a) dibenzylaminoethyl, (b) isoprenyl, (c) geranyl, (d) farnesyl, (e) t-butyloxycarbonyl, (f) ethoxycarbonyl, (g) pivaloyl, (h) cyclohexyl methyl, (i) pyridylmethyl, (j) nicotihoyl, (k) thienylmethyl, (1) benzyl, (m) benzoyl, (n) benzyloxycarbonyl, (o) phenylpropyl, (p) cinnamyl, (q) biphenyl, (r) biphenylmethyl, (s) diphenyl C$_{1-4}$ alkyl, (t) diphenylmethylcarbonyl, and (u) benzhydryloxycarbonyl. In this case, one or more hydrogen atoms on the benzene ring in (1) benzyl, (m) benzoyl, (n) benzyloxycarbonyl, (o) phenylpropyl, (p) cinnamyl, (q) biphenyl, (r) biphenylmethyl, (s) diphenyl C$_{1-4}$ alkyl, (t) diphenylmethylcarbonyl, and (u) benzhydryloxycarbonyl may be substituted, and examples of substituents usable herein include hydroxy, halogens (preferably fluorine, chlorine, and bromine) atoms, nitro, and C$_{1-6}$ alkoxys (preferably methoxy and ethoxy).

Examples of preferred groups represented by formula —K—L—M include:

cycloalkyls having 3 to 8 carbon atoms wherein one or more hydrogen atoms on the cycloalkyl may be substituted by hydroxy or acyloxy having 1 to 4 carbon atoms;

phenyl-C$_{1-6}$ alkylene- wherein one or more hydrogen atoms on the phenyl or alkylene may be substituted by hydroxy, a halogen atom, alkoxy having 1 to 6 carbon atoms, nitro, alkyl having 1 to 4 carbon atoms, trifluoromethyl, or alkoxycarbonyl having 1 to 4 carbon atom;

C$_{3-8}$ cycloalkyl-C$_{1-6}$ alkylene- wherein one or more hydrogen atoms on the cycloalkyl may be substituted by hydroxy or acyloxy having 1 to 4 carbon atoms;

alkyls having 1 to 6 carbon atoms wherein one or more hydrogen atoms in the alkyl may be substituted by alkoxycarbonyl having 1 to 4 carbon atoms;

allyl;

cinnamyl;

a five- or six-membered heterocylic ring containing up to two hetero atoms-C$_{1-6}$ alkylene- wherein one or more hydrogen atoms on the heterocyclic ring may be substituted by alkyl having 1 to 4 carbon atoms;

diphenylmethyl-C$_{1-6}$ alkylene-; and biphenyl-C$_{1-6}$ alkylene-.

Among the compounds represented by formula (I) according to the present invention, a group of preferred compounds include compounds wherein A represents group —CH$_2$— or —CH$_2$CH$_2$—;

B represents a hydrogen or halogen atom;

X represents —CR$^3$R$^4$R$^5$ wherein R$^3$, R$^4$, and R$^5$ each are as defined above in connection with formula (I), —NR$^6$R$^7$ wherein R$^6$ and R$^7$ each are as defined above in connection with formula (I), —(CH$_2$—CH═C(CH$_3$)—CH$_2$)$_p$—CH$_2$CH═C(CH$_3$)$_2$ wherein p is as defined above in connection with formula (I), alkyl having 1 to 18 carbon atoms, cycloalkyl having 3 to 8 carbon atoms, optionally substituted phenyl, optionally substituted cinnamyl, or a five- or six-membered aromatic ring containing up to two hetero atoms;

Y represents —$(CH_2)_q$— wherein q is as defined above in connection with formula (I),

—NH—, an oxygen atom, or a bond;

Z represents carbonyl or a bond;

K represents optionally substituted alkylene having 1 to 6 carbon atoms or a bond;

L represents —CH═CH— or a bond; and

M represents a hydrogen atom, optionally substituted alkyl having 1 to 6 carbon atoms, optionally substituted cycloalkyl having 3 to 8 carbon atoms, optionally substituted phenyl, an optionally substituted five- or six-membered, saturated or unsaturated heterocyclic ring containing up to two hetero atoms, optionally substituted biphenyl, or optionally substituted diphenylmethyl.

According to a preferred embodiment of the present invention, a group of preferred compounds represented by formula (I) according to the present invention include a group of compounds represented by formula (II):

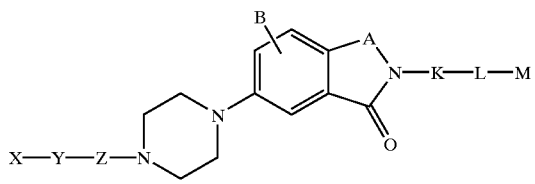

(II)

wherein A, B, X, Z, K, L, and M each are as defined above in connection with formula (I); and Y represents $(CH_2)_q$— with q being an integer of 1 to 6, —NH—, an oxygen atom, or a bond, provided that compounds, wherein —K—L—M represents —H, are excluded.

Among the group of compounds represented by formula (II), a group of further preferred compounds include compounds wherein A represents group —$CH_2$— or —$CH_2CH_2$—;

B represents a hydrogen or halogen atom;

X represents —$CR^3R^4R^5$ wherein $R^3$, $R^4$, and $R^5$ each are as defined above in connection with formula (I), —$NR^6R^7$ wherein $R^6$ and $R^7$ each are as defined above in connection with formula (I), —$(CH_2$—$CH$═$C(CH_3)$—$CH_2)_p$—$CH_2CH$═$C(CH_3)_2$ wherein p is as defined above in connection with formula (I), alkyl having 1 to 18 carbon atoms, cycloalkyl having 3 to 8 carbon atoms, optionally substituted phenyl, optionally substituted cinnamyl, or a five- or six-membered heteroaromatic ring containing up to two hetero atoms;

Y represents —$(CH_2)_q$— with q being an integer of 1 to 6, —NH—, an oxygen atom, or a bond;

Z represents carbonyl or a bond;

K represents optionally substituted alkylene having 1 to 6 carbon atoms or a bond;

L represents —CH═CH— or a bond; and

M represents a hydrogen atom, optionally substituted alkyl having 1 to 6 carbon atoms, optionally substituted cycloalkyl having 3 to 8 carbon atoms, optionally substituted phenyl, an optionally substituted five- or six-membered, saturated or unsaturated heterocyclic ring containing up to two hetero atoms, optionally substituted biphenyl, or optionally substituted diphenylmethyl.

Further, a group of further preferred compounds represented by formula (II) include compounds wherein A represents group —$CR^1R^2$—$(CH_2)_i$— wherein $R^1$ and $R^2$, which may be the same or different, each represent a hydrogen atom or alkyl having 1 to 6 carbon atoms and i is an integer of 0 or 1,

—CH═CH—,

—O—$CH_2$—, or

—$S(O)_j$—$CH_2$— wherein j is an integer of 0 to 2;

B represents a hydrogen or halogen atom;

X represents —$CR^3R^4R^5$ wherein $R^3$, $R^4$, and $R^5$ each are as defined above in connection with formula (I) or —$(CH_2$—$CH$═$C(CH_3)$—$CH_2)_p$—$CH_2CH$═$C(CH_3)_2$ wherein p is as defined above in connection with formula (I);

Y represents —$(CH_2)_q$— wherein q is an integer of 1 to 6,

—NH—, an oxygen atom, or a bond;

Z represents carbonyl or a bond;

K represents optionally substituted alkylene having 1 to 6 carbon atoms or a bond;

L represents —CH═CH— or a bond; and

M represents a hydrogen atom, optionally substituted alkyl having 1 to 6 carbon atoms, optionally substituted cycloalkyl having 3 to 8 carbon atoms, optionally substituted phenyl, an optionally substituted, five- or six-membered, saturated or unsaturated heterocyclic ring containing up to two heterol atoms, optionally substituted biphenyl, or optionally substituted diphenylmethyl.

Further, a group of further preferred compounds represented by formula (II) include compounds wherein A represents group —$CR^1R^2$—$(CH_2)_i$— wherein $R^1$, $R^2$, and i each are as defined above in connection with formula (I),

—CH═CH—,

—O—$CH_2$—, or

—$S(O)_j$—$CH_2$— wherein j is as defined above in connection with formula (I);

B represents a hydrogen or halogen atom;

X represents —$CR^3R^4R^5$ wherein $R^3$, $R^4$, and $R^5$ each are as defined above in connection with formula (I), —$NR^6R^7$ wherein $R^6$ and $R^7$ each are as defined above in connection with formula (I), —$(CH_2$—$CH$═$C(CH_3)$—$CH_2)_p$—$CH_2CH$═$C(CH_3)_2$ wherein p is as defined above in connection with formula (I), alkyl having 1 to 18 carbon atoms, cycloalkyl having 3 to 8 carbon atoms, optionally substituted phenyl, optionally substituted cinnamyl, or a five- or six-membered heteroaromatic ring containing up to two hetero atoms;

Y represents —$(CH_2)_q$— wherein q is as defined in claim 1,

—NH—, an oxygen atom, or a bond;

Z represents carbonyl or a bond;

K represents optionally substituted alkylene having 1 to 3 carbon atoms or a bond;

L represents —CH=CH— or a bond; and

M represents a hydrogen atom, optionally substituted cycloalkyl having 3 to 8 carbon atoms, optionally substituted phenyl, or an optionally substituted, five- or six-membered heterocyclic ring containing up to two hetero atoms.

Specific examples of compounds represented by formula (I) according to the invention include 2-cyclohexyl-6-[4-(trans,trans-farnesyl)piperazin-1-yl]-2,3-dihydro-1H-isoindol-1-one, 2-cyclohexyl-6-[4-(3,3-diphenyl-1-propyl)piperazin-1-yl]-2,3-dihydro-1H-isoindol-1-one, 6-[4-(N,N-dibenzylaminoethyl)piperazin-1-yl]-2-cyclohexyl-2,3-dihydro-1H-isoindol-1-one, 2-(4-acetoxy)cyclohexyl-6-[4-(3,3-diphenyl-1-propyl) piperazin-1-yl]-2,3-dihydro-1H-isoindol-1-one, 2-benzyl-6-[4-(3,3-diphenyl-1-propyl)piperazin-1- yl]-2,3-dihydro-1H-isoindol-1-one, 2-cyclohexyl-7-[4-(3,3-diphenyl-1-propyl)piperazin-1-yl]-3,4-dihydro-2H-isoquinolin-1-one, 2-cyclohexyl-6-[4-(2-diphenylethyl)piperazin-1-yl]-2,3-dihydro-1H-isoindol-1-one, 2-benzyl-6-[4-(t-butoxycarbonyl)piperazin-1-yl]-2,3-dihydro-1H-isoindol-1-one, 3-cyclohexyl-6-[4-(3,3-diphenyl-1-propyl)piperazin-1-yl]3,4-dihydro-2H-1,3-benzoxazin-4-one, 2-cyclohexyl-6-[4-(geranyl)piperazin-1-yl]-2,3-dihydro-1H-isoindol-1-one, 2-cyclohexyl-6-[4-(benzhydryl)piperazin-1-yl)-2,3-dihydro-1H-isoindol-1-one, 2-cyclohexyl-6-{4-[3,3-bis(4-chlorophenyl)-1-propyl] piperazin-1-yl}-2,3-dihydro-1H-isoindol-1-one, 2-cyclohexyl-6-[4-(3,3-diphenyl-1-propyl)piperazin-1-yl]-4-fluoro-2,3-dihydro-1H-isoindol-1-one, 2-cyclohexyl-6-[4-(3,3-diphenyl-1-propyl)piperazin-1-yl]-5-fluoro-2,3-dihydro-1H-isoindol-1-one, 2-cyclohexyl-6-[4-(3,3-diphenyl-1-propyl)piperazin-1-yl]-7-fluoro-2,3-dihydro-1H-isoindol-1-one, 2-benzyl-7-[4-(3,3-diphenyl-1-propyl)piperazin-1- yl]-3,4-dihydro-2H-isoquinolin-1-one, 2-cyclohexylmethyl-7-[4-(3,3-diphenyl-1-propyl)piperazin-1-yl]-3,4-dihydro-2H-isoquinolin-1-one, 6-[4-(3,3-diphenyl-1-propyl)piperazin-1-yl)-2-(4-methoxybenzyl)-2,3-dihydro-1H-isoindol-1-one, 2-(4-bromobenzyl)-6-[4-(3,3-diphenyl-1-propyl)piperazin-1-yl]-2,3-dihydro-1H-isoindol-1-one, Ethyl{6-[4-(3,3-diphenyl-1-propyl)piperazin-1-yl]-1-oxo 1,3-dihydro-1H-isoindol-2-yl}acetate, 2-(4-chlorobenzyl)-7-[4-(3,3-diphenyl-1-propyl)piperazin-1-yl]-3,4-dihydro-2H-isoquinolin-1-one, 2-cyclopropyl-6-[4-(3,3-diphenyl-1-propyl)piperazin-1-yl]-2,3-dihydro-1H-isoindol-1-one, 2-cyclohexylmethyl-6-[4-(3,3-diphenyl-1-propyl)piperazin-1-yl]-2,3-dihydro-1H-isoindol-1-one, 2-cyclopropylmethyl-6-[4-(3,3-diphenyl-1-propyl) piperazin-1-yl]-2,3-dihydro-1H-isoindol-1-one, 2-(2-chlorobenzyl)-7-[4-(3,3-diphenyl-1-propyl)piperazin-1-yl]-3,4-dihydro-2H-isoquinolin-1-one, 2-(3-chlorobenzyl)-7-[4-(3,3-diphenyl-1-propyl)piperazin-1-yl]-3,4-dihydro-2H-isoquinolin-1-one, 6-[4-(benzhydryloxycarbonyl)piperazin-1-yl]-2-cyclohexyl-2,3-dihydro-1H-isoindol-1-one, 2-cyclohexyl-7-[4-(3,3-diphenyl-1-propyl)piperazin-1-yl]-2H-isoquinolin-1-one, 2-cyclohexyl-6-{4-[3,3-bis(4-methoxyphenyl)-1-propyl] piperazin-1-yl}-2,3-dihydro-1H-isoindol-1-one, 2-benzyl-7-(4-t-butoxycarbonylpiperazin-1-yl)-3,4-dihydro-2H-isoquinolin-1-one, 2-(4-bromobenzyl)-6-(4-t-butoxycarbonylpiperazin-1-yl)-2,3-dihydro-1H-isoindol-1-one, 3-cyclohexyl-6-[4-(3,3-diphenyl-1-propyl)piperazin-1-yl]-3,4-dihydro-2H-1,3-benzothiazin-4-one, 2-cyclopropylmethyl-7-[4-(3,3-diphenyl-1-propyl) piperazin-1-yl]-3,4-dihydro-2H-isoquinolin-1-one, 7-chloro-2-cyclohexyl-6-[4-(3,3-diphenyl-1-propyl) piperazin- 1-yl]-2,3-dihydro-1H-isoindol-1-one, 5-chloro-2-cyclohexyl-6-[4-(3,3-diphenyl-1-propyl) piperazin-1-yl]-2,3-dihydro-1H-isoindol-1-one, 4-chloro-2-cyclohexyl-6-[4-(3,3-diphenyl-1-propyl) piperazin-1-yl]-2,3-dihydro-1H-isoindol-1-one, 2-cyclobutyl-6-[4-(3,3-diphenyl-1-propyl)piperazin-1-yl]-2,3-dihydro-1H-isoindol-1-one, 2-cyclopentyl-6-[4-(3,3-diphenyl-1-propyl)-piperazin-1-yl]-2,3-dihydro-1H-isoindol-1-one, 2-cycloheptyl-6-[4-(3,3-diphenyl-1-propyl)-piperazin-1-yl]-2,3-dihydro-1H-isoindol-1-one, 2-cyclobutylmethyl-6-[4-(3,3-diphenyl-1-propyl)piperazin-1-yl]-2,3-dihydro-1H-isoindol-1-one, 2-cyclopentylmethyl-6-[4-(3,3-diphenyl-1-propyl) piperazin-1-yl]-2,3-dihydro-1H-isoindol-1-one, 2-cycloheptylmethyl-6-[4-(3,3-diphenyl-1-propyl) piperazin-1-yl]-2,3-dihydro-1H-isoindol-1-one, 2-cyclopropyl-7-[4-(3,3-diphenyl-1-propyl)piperazin-1-yl)-3,4-dihydro-2H-isoquinolin-1-one, 2-cyclobutyl-7-[4-(3,3-diphenyl-1-propyl)piperazin-1-yl]-3,4-dihydro-2H-isoquinolin-1-one, 2-cyclopentyl-7-[4-(3,3-diphenyl-1-propyl)-piperazin-1-yl]-3,4-dihydro-2H-isoquinolin-1-one, 2-cycloheptyl-7-[4-(3,3-diphenyl-1-propyl)-piperazin-1-yl]-3,4-dihydro-2H-isoquinolin-1-one, 2-cyclobutylmethyl-7-[4-(3,3-diphenyl-1-propyl)piperazin-1-yl]-3,4-dihydro-2H-isoquinolin-1-one, 2-cyclopentylmethyl-7-[4-(3,3-diphenyl-1-propyl) piperazin-1-yl]-3,4-dihydro-2H-isoquinolin-1-one, 2-cycloheptylmethyl-7-[4-(3,3-diphenyl-1-propyl) piperazin-1-yl]-3,4-dihydro-2H-isoquinolin-1-one, 6-[4-(3,3-diphenyl-1-propyl)piperazin-1-yl]-2-phenyl-2,3-dihydro-1H-isoindol-1-one, 6-[4-(3,3-diphenyl-1-propyl)piperazin-1-yl]-2-(4-hydroxyphenyl)-2,3-dihydro-1H-isoindol-1-one, 6-[4-(3,3-diphenyl-1-propyl)piperazin-1-yl]-2-(4-fluorophenyl)-2,3-dihydro-1H-isoindol-1-one, 2-(4-chlorophenyl)-6-[4-(3,3-diphenyl-1-propyl)piperazin-1-yl]-2,3-dihydro-1H-isoindol-1-one, 2-(4-bromophenyl)-6-[4-(3,3-diphenyl-1-propyl)piperazin-1-yl]-2,3-dihydro-1H-isoindol-1-one, 2-(4-aminophenyl)-6-[4-(3,3-diphenyl-1-propyl)piperazin-1-yl]-2,3-dihydro-1H-isoindol-1-one, 6-[4-(3,3-diphenyl-1-propyl)piperazin-1-yl]-2-(4-methoxyphenyl)-2,3-dihydro-1H-isoindol-1-one,
6-[4-(3,3-diphenyl-1-propyl)piperazin-1-yl]-2-(4-ethoxyphenyl)-2,3-dihydro-1H-isoindol-1-one,
6-[4-(3,3-diphenyl-1-propyl)piperazin-1-yl]-2-(4-methoxycarbonylphenyl)-2,3-dihydro-1H-isoindol-1-one,
6-[4-(3,3-diphenyl-1-propyl)piperazin-1-yl]-2-(4-ethoxycarbonylphenyl)-2,3-dihydro-1H-isoindol-1-one,
6-[4-(3,3-diphenyl-1-propyl)piperazin-1-yl]-2-(4-hydroxybenzyl)-2,3-dihydro-1H-isoindol-1-one,
6-[4-(3,3-diphenyl-1-propyl)piperazin-1-yl]-2-(4-fluorobenzyl)-2,3-dihydro-1H-isoindol-1-one,
2-(4-chlorobenzyl)-6-[4-(3,3-diphenyl-1-propyl)piperazin-1-yl]-2,3-dihydro-1H-isoindol-1-one,
2-(4-aminobenzyl)-6-[4-(3,3-diphenyl-1-propyl) piperazin-1-yl]-2,3-dihydro-1H-isoindol-1-one,
6-[4-(3,3-diphenyl-1-propyl)piperazin-1-yl]-2-(4-ethoxybenzyl)-2,3-dihydro-1H-isoindol-1-one,
6-[4-(3,3-diphenyl-1-propyl)piperazin-1-yl]-2-(4-methoxycarbonylbenzyl)-2,3-dihydro-1H-isoindol-1-one,
7-[4-(3,3-diphenyl-1-propyl)piperazin-1-yl]-2-phenyl-3,4dihydro-2H-isoquinolin-1-one,
7-[4-(3,3-diphenyl-1-propyl)piperazin-1-yl]-2-(4-hydroxyphenyl)-3,4-dihydro-2H-isoquinolin-1-one,
7-[4-(3,3-diphenyl-1-propyl)piperazin-1-yl]-2-(4-fluorophenyl)-3,4-dihydro-2H-isoquinolin-1-one,
2-(4-chlorophenyl)-7-[4-(3,3-diphenyl-1-propyl)piperazin-1-yl]-3,4-dihydro-2H-isoquinolin-1-one,
2-(4-bromophenyl)-7-[4-(3,3-diphenyl-1-propyl)piperazin-1-yl]-3,4-dihydro-2H-isoquinolin-1-one,
2-(4-aminophenyl)-7-[4-(3,3-diphenyl-1-propyl)piperazin-1-yl]3,4-dihydro-2H-isoquinolin-1-one,
7-[4-(3,3-diphenyl-1-propyl)piperazin-1-yl]-2-(4-methoxyphenyl)-3,4-dihydro-2H-isoquinolin-1-one,
7-[4-(3,3-diphenyl-1-propyl)piperazin-1-yl]-2-(4-ethoxyphenyl)-3,4-dihydro-2H-isoquinolin-1-one,
7-[4-(3,3-diphenyl-1-propyl)piperazin-1-yl]-2-(4methoxycarbonylphenyl)-3,4-dihydro-2H-isoquinolin-1-one,
7-[4-(3,3-diphenyl-1-propyl)piperazin-1-yl]-2-(4-ethoxycarbonylphenyl)-3,4-dihydro-2H-isoquinolin-1-one,
7-[4-(3,3-diphenyl-1-propyl)piperazin-1-yl]-2-(4-hydroxybenzyl)-3,4-dihydro-2H-isoquinolin-1-one,
7-[4-(3,3-diphenyl-1-propyl)piperazin-1-yl]-2-(4-fluorobenzyl)-3,4-dihydro-2H-isoquinolin-1-one,
2-(4-bromobenzyl)-7-[4-(3,3-diphenyl-1-propyl)piperazin-1-yl]-3,4-dihydro-2H-isoquinolin-1-one,
2-(4-aminobenzyl)-7-[4-(3,3-diphenyl-1-propyl)piperazin-1-yl]-3,4-dihydro-2H-isoquinolin-1-one,
7-[4-(3,3-diphenyl-1-propyl)piperazin-1-yl]-2-(4-methoxybenzyl)-3,4-dihydro-2H-isoquinolin-1-one,
7-[4-(3,3-diphenyl-1-propyl)piperazin-1-yl]-2-(4-ethoxybenzyl)-3,4-dihydro-2H-isoquinolin-1-one,
7-[4-(3,3-diphenyl-1-propyl)piperazin-1-yl]-2-(4-methoxycarbonylbenzyl)-3,4-dihydro-2H-isoquinolin-1-one,
7-[4-(3,3-diphenyl-1-propyl)piperazin-1-yl]-2-(4-ethoxycarbonylbenzyl)-3,4-dihydro-2H-isoquinolin-1-one,
2-benzyl-7-[4-(3,3-diphenyl-1-propyl)piperazin-1-yl]-4-fluoro-3,4-dihydro-2H-isoquinolin-1-one,
2-benzyl-7-[4-(3,3-diphenyl-1-propyl)piperazin-1-yl]-5-fluoro-3,4-dihydro-2H-isoquinolin-1-one,
2-benzyl-7-[4-(3,3-diphenyl-1-propyl)piperazin-1-yl]-7-fluoro-3,4-dihydro-2H-isoquinolin-1-one,
2-benzyl-4-chloro-7-[4-(3,3-diphenyl-1-propyl)piperazin-1-yl]-3,4-dihydro-2H-isoquinolin-1-one,
2-benzyl-5-chloro-7-[4-(3,3-diphenyl-1-propyl)piperazin-1-yl]-3,4-dihydro-2H-isoquinolin-1-one,
2-benzyl-7-chloro-7-[4-(3,3-diphenyl-1-propyl)piperazin-1-yl]-3,4-dihydro-2H-isoquinolin-1-one,
7-[4-(3,3-diphenyl-1-propyl)piperazin-1-yl-]4-fluoro-2-phenyl-3,4-dihydro-2H-isoquinolin-1-one,
7-[4-(3,3-diphenyl-1-propyl)piperazin-1-yl]-5-fluoro-2-phenyl-3,4-dihydro-2H-isoquinolin-1-one,
7-[4-(3,3-diphenyl-1-propyl)piperazin-1-yl]-7-fluoro-2-phenyl-3,4-dihydro-2H-isoquinolin-1-one,
2-cyclohexyl-6-[4-(4,4-diphenyl-1-butyl)piperazin-1-yl]-2,3-dihydro-1H-isoindol-1-one,
2-benzyl-7-[4-(4,4-diphenyl-1-butyl)piperazin-1-yl]-3,4-dihydro-2H-isoquinolin-1-one,
2-cyclopropyl-6-[4-(4,4-diphenyl-1-butyl)piperazin-1-yl]-2,3-dihydro-1H-isoindol-1-one,
2-cyclopropyl-7-[4-(4,4-diphenyl-1-butyl)piperazin-1-yl]-3,4-dihydro-2H-isoquinolin-1-one,
6-[4-(4,4-diphenyl-1-butyl)piperazin-1-yl]-2-phenyl-2,3-dihydro-1H-isoindol-1-one,
7-[4-(4,4-diphenyl-1-butyl)piperazin-1-yl]-2-phenyl-3,4-dihydro-2H-isoquinolin-1-one,
6-[4-(benzyl)piperazin-1-yl]-2-cyclohexyl-2,3-dihydro-1H-isoindol-1-one,
6-[4-(4-chlorobenzyl)piperazin-1-yl]-2-cyclohexyl-2,3-dihydro-1H-isoindol-1-one,
2-cyclohexyl-6-[4-(3-pyridylmethyl)piperazin-1-yl]-2,3dihydro-1H-isoindol-1-one,
2-cyclohexyl-6-[4-(octadecyl)piperazin-1-yl]-2,3-dihydro-1H-isoindol-1-one,
2-cyclohexyl-6-[4-(2-thenyl)piperazin-1-yl]-2,3-dihydro-1H-isoindol-1-one,
2-cyclohexyl-6-[4-(cyclohexylmethyl)piperazin-1-yl]-2,3-dihydro-1H-isoindol-1-one,
2-cyclohexyl-6-[4-(4-methoxybenzyl)piperazin-1-yl]-2,3-dihydro-1H-isoindol-1-one,
2-cyclohexyl-6-[4-(isoprenyl)piperazin-1-yl]-2,3-dihydro-1H-isoindol-1-one,
2-cyclohexyl-6-[4-(4-fluorobenzyl)piperazin-1-yl]-2,3-dihydro-1H-isoindol-1-one,
2-cyclohexyl-6-[4-(4-nitrobenzyl)piperazin-1-yl]-2,3-dihydro-1H-isoindol-1-one,
2-cyclohexyl-6-[4-(3-phenyl-1-propyl)piperazin-1-yl]-2,3-dihydro-1H-isoindol-1-one,
6-[4-(cinnamyl)piperazin-1-yl]-2-cyclohexyl-2,3-dihydro-1H-isoindol-1-one,
6-[4-(3-chlorobenzyl)piperazin-1-yl]-2-cyclohexyl-2,3-dihydro-1H-isoindol-1-one,
6-[4-(4-bromobenzyl)piperazin-1-yl]-2-cyclohexyl-2,3-dihydro-1H-isoindol-1-one,
6-[4-(2-chlorobenzyl)piperazin-1-yl]-2-cyclohexyl-2,3-dihydro-1H-isoindol-1-one,
2-cyclohexyl-6-[4-(triphenylmethyl)piperazin-1-yl]-2,3-dihydro-1H-isoindol-1-one, 2-cyclohexyl-6-[4-(3,4-dichlorobenzyl)piperazin-1-yl]2,3-dihydro-1H-isoindol-1-one,
2-cyclohexyl-6-[4-(4-biphenylmethyl)piperazin-1-yl]-2,3-dihydro-1H-isoindol-1-one,
6-[4-(3,3-diphenyl-1-propyl)piperazin-1-yl]-2-(4-hydroxy)cyclohexyl-2,3-dihydro-1H-isoindol-1-one,
6-[4-(benzyloxycarbonyl)piperazin-1-yl]-2-cyclohexyl-2,3-dihydro-1H-isoindol-1-one,
2-cyclohexyl-6-[4-(ethoxycarbonyl)piperazin-1-yl]-2,3-dihydro-1H-isoindol-1-one,
6-[4-(t-butoxycarbonyl)piperazin-1-yl]-2-cyclohexyl-2,3-dihydro-1H-isoindol-1-one, 6-[4-(benzoyl)piperazin-1-yl]-2-cyclohexyl-2,3-dihydro-1H-isoindol-1-one,
2-cyclohexyl-6-[4-(pivaloyl)piperazin-1-yl]-2,3-dihydro-1H-isoindol-1-one,
2-cyclohexyl-6-[4-(methoxybenzyloxycarbonyl)-piperazin-1-yl]-2,3-dihydro-1H-isoindol-1-one,
2-cyclohexyl-6-[4-(3,5-dimethoxy-4-hydroxybenzoyl)-piperazin-1-yl]-2,3-dihydro-1H-isoindol-1-one,
2-cyclohexyl-6-[4-(pyridine-3-carbonyl)piperazin-1-yl]-2,3-dihydro-1H-isoindol-1-one,
2-cyclohexyl-6-[4-diphenylacetylpiperazin-1-yl]-2,3-dihydro-1H-isoindol-1-one,
2-cyclohexyl-6-[4-(4-hydroxyphenyl)methylpiperazin-1-yl]2,3-dihydro-1H-isoindol-1-one,
2-cyclohexyl-5-[4-(3,3-diphenyl-1-propyl)piperazin-1-yl]2,3-dihydro-1H-isoindol-1-one,
2-cyclohexyl-5-[4-(trans,trans-farnesyl)piperazin-1-yl]2,3-dihydro-1H-isoindol-2-one,
6-[4-(t-butoxycarbonyl)piperazin-1-yl]-7-chloro-2-cyclohexyl-2,3-dihydro-1H-isoindol-1-one,
6-[4-(t-butoxycarbonyl)piperazin-1-yl]-5-chloro-2-cyclohexyl-2,3-dihydro-1H-isoindol-1-one,
6-[4-(t-butoxycarbonyl)piperazin-1-yl]-2,3-dihydro-1H-isoindol-1-one,
6-[4-(3,3-diphenyl-1-propyl)piperazin-1-yl]-2,3-dihydro-1H-isoindol-1-one,
6-(4-t-butoxycarbonylpiperazin-1-yl)-2-(4chlorobenzyl)-2,3-dihydro-1H-isoindol-1-one,
6-(4-t-butoxycarbonylpiperazin-1-yl)-2-(4-methoxy-benzyl)-2,3-dihydro-1H-isoindol-1-one,
6-(4-t-butoxycarbonylpiperazin-1-yl)-2-cyclopropyl-methyl-2,3-dihydro-1H-isoindol-1-one,
6-(4-t-butoxycarbonylpiperazin-1-yl)-2-cyclohexyl-methyl-2,3-dihydro-1H-isoindol-1-one,
6-[4-(t-butoxycarbonyl)piperazin-1-yl]-2-methyl-2,3-dihydro-1H-isoindol-1-one,
6-[4-(3,3-diphenyl-1-propyl)piperazin-1-yl]-2-methyl-2,3-dihydro-1H-isoindol-1-one,
6-(4-t-butoxycarbonylpiperazin-1-yl)-2-(4-nitro-benzyl)-2,3-dihydro-1H-isoindol-1-one,
Ethyl[6-(4-t-butoxycarbonylpiperazin-1-yl)-1-oxo-1,3-dihydro-isoindol-2-yl]acetate,
2-cyclohexyl-7-(4-t-butoxycarbonylpiperazin-1-yl)-3,4-dihydro-2H-isoquinolin-1-one,
2-cyclohexyl-7-(4-t-butoxycarbonylpiperazin-1-yl)-2H-isoquinolin-1-one,
2-methyl-7-(4-t-butoxycarbonylpiperazin-1-yl)-3,4-dihydro-2H-isoquinolin-1-one,
7-[4-(3,3-diphenyl-1-propyl)piperazin-1-yl]-2 -methyl-3,4-dihydro-2H-isoquinolin-1-one,
2-cyclohexylmethyl-7-(4-t-butoxycarbonylpiperazin-1-yl)-3,4-dihydro-2H-isoquinolin-1-one,
2-cyclopropylmethyl-7-(4-t-butoxycarbonylpiperazin-1-yl)-3,4-dihydro-2H-isoquinolin-1-one,
2-(4-chlorobenzyl)-7-(4-t-butoxycarbonylpiperazin-1-yl)-3,4-dihydro-2H-isoquinolin-1-one,
7-[4-(3,3-diphenyl-1-propyl)piperazin-1-yl]-3,4-dihydro-2H-isoquinolin-1-one,
3,3-dimethyl-6-[4-(3,3-diphenyl-1-propyl)piperazin-1-yl]-2,3-dihydro-1H-isoindol-1-one,
3-cyclohexyl-6-[4-(3,3-diphenyl-1-propyl)piperazin-1-yl]-3,4-dihydro-2H-1,3-benzoxazin-4-one,
2-cyclohexyl-6-[4-(2-diphenylamino-ethyl)piperazin-1-yl]2,3-dihydro-1H-isoindol-1-one,
4-(2-cyclohexyl-1-oxo-2,3-dihydro-1H-isoindol-6-yl)piperazine-1-carboxylic acid benzhydrylamide,
7-[4-(benzhydryloxycarbonyl)piperazin-1-yl]-2-benzyl-3,4-dihydro-2H-isoquinolin-1-one,
2-benzyl-7-[4-(4-chlorobenzyl)piperazin-1-yl]-3,4-dihydro-2H-isoquinolin-1-one,
6-[4-(3,3-diphenyl-1-propyl)piperazin-1-yl]-2-isopropyl-2,3-dihydro-1H-isoindol-1-one,
2-alyl-6-[4-(3,3-diphenyl-1-propyl)piperazin-1-yl]-2,3-dihydro-1H-isoindol-1-one,
2-cinnamyl-[4-(3,3-diphenyl-1-propyl)piperazin-1-yl]-2,3-dihydro-1H-isoindol-1-one,
6-[4-(3,3-diphenyl-1-propyl)piperazin-1-yl]-2-(3-methoxybenzyl)-2,3-dihydro-1H-isoindol-1-one,
6-[4-(3,3-diphenyl-1-propyl)piperazin-1-yl]-2-(3-methylbenzyl)-2,3-dihydro-1H-isoindol-1-one,
6-[4-(3,3-diphenyl-1-propyl)piperazin-1-yl]-2-(3-trifluoromethylbenzyl)-2,3-dihydro-1H-isoindol-1-one,
6-[4-(3,3-diphenyl-1-propyl)piperazin-1-yl]-2-(3-nitrobenzyl)-2,3-dihydro-1H-isoindol-1-one,
6-[4-(3,3-diphenyl-1-propyl)piperazin-1-yl]-2-(thiazol-4-yl)methyl-2,3-dihydro-1H-isoindol-1-one,
2-benzyl-3,3-dimethyl-6-[4-(3,3-diphenyl-1-propyl)piperazin-1-yl]-2,3-dihydro-1H-isoindol-1-one,
3,3-dimethyl-6-[4-(3,3-diphenyl-1-propyl)piperazin-1-yl]-2-(2-methylbenzyl)-2,3-dihydro-1H-isoindol-1-one,
3,3-dimethyl-6-[4-(3,3-diphenyl-1-propyl)piperazin-1-yl]-2-(1-phenylethyl)-2,3-dihydro-1H-isoindol-1-one,
2-allyl-7-[4-(3,3-diphenyl-1-propyl)piperazin-1-yl]-3,4-dihydro-2H-isoquinolin-1-one,
2-cinnamyl-7-[4-(3,3-diphenyl-1-propyl)piperazin-1-yl]-3,4-dihydro-2H-isoquinolin-1-one,
7-[4-(3,3-diphenyl-1-propyl)piperazin-1-yl]-2-(3-phenyl-1-propyl)-3,4-dihydro-2H-isoquinolin-1-one,
7-[4-(3,3-diphenyl-1-propyl)piperazin-1-yl]-2-phenyletyl-3,4-dihydro-2H-isoquinolin-1-one,
2-(3,3-diphenyl-1-propyl)-7-[4-(3,3-diphenyl-1-propyl)piperazin-1-yl]-3,4-dihydro-2H-isoquinolin-1-one,
7-[4-(3,3-diphenyl-1-propyl)piperazin-1-yl]-2-(2-methylbenzyl)-3,4-dihydro-2H-isoquinolin-1-one,
7-[4-(3,3-diphenyl-1-propyl)piperazin-1-yl]-2-(3-methylbenzyl)-3,4-dihydro-2H-isoquinolin-1-one,
7-[4-(3,3-diphenyl-1-propyl)piperazin-1-yl]-2-(4-methylbenzyl)-3,4-dihydro-2H-isoquinolin-1-one,
2-(3,4-dimethylbenzyl)-7-[4-(3,3-diphenyl-1-propyl)piperazin-1-yl]-3,4-dihydro-2H-isoquinolin-1-one,
2-(2,5-dimethylbenzyl)-7-[4-(3,3-diphenyl-1-propyl)piperazin-1-yl]-3,4-dihydro-2H-isoquinolin-1-one,
7-[4-(3,3-diphenyl-1-propyl)piperazin-1-yl]-2-(2,4,6-trimethylbenzyl)-3,4-dihydro-2H-isoquinolin-1-one,
7-[4-(3,3-diphenyl-1-propyl)piperazin-1-yl]-2-(1-phenylethyl)-3,4-dihydro-2H-isoquinolin-1-one,
7-[4-(3,3-diphenyl-1-propyl)piperazin-1-yl]-2-(4-trifluoromethylbenzyl)-3,4-dihydro-2H-isoquinolin-1-one,
7-[4-(3,3-diphenyl-1-propyl)piperazin-1-yl]-2-(3-trifluoromethylbenzyl)-3,4-dihydro-2H-isoquinolin-1-one,
7-[4-(3,3-diphenyl-1-propyl)piperazin-1-yl]-2-(3-fluorobenzyl)-3,4-dihydro-2H-isoquinolin-1-one,
2-(3-bromobenzyl)-7-[4-(3,3-diphenyl-1-propyl)piperazin-1-yl]-3,4-dihydro-2H-isoquinolin-1-one,
2-(3,4-dichlorobenzyl)-7-[4-(3,3-diphenyl-1-propyl)piperazin-1-yl]-3,4-dihydro-2H-isoquinolin-1-one,
2-(2,4-dichlorobenzyl)-7-[4-(3,3-diphenyl-1-propyl)piperazin-1-yl]-3,4-dihydro-2H-isoquinolin-1-one,
7-[4-(3,3-diphenyl-1-propyl)piperazin-1-yl]-2-(3-methoxybenzyl)-3,4-dihydro-2H-isoquinolin-1-one,
2-(3,5-dimethoxybenzyl)-7-[4-(3,3-diphenyl-1-propyl)piperazin-1-yl]-3,4-dihydro-2H-isoquinolin-1-one,
7-[4-(3,3-diphenyl-1-propyl)piperazin-1-yl]-2-(3-hydroxybenzyl)-3,4-dihydro-2H-isoquinolin-1-one, 2-(3,5-dihydroxybenzyl)-7-[4-(3,3-diphenyl-1-propyl) piperazin-1-yl]-3,4-dihydro-2H-isoquinolin-1-one, 2-(2-hydroxy-2-phenyl)ethyl-7-[4-(3,3-diphenyl-1-propyl) piperazin-1-yl]-3,4-dihydro-2H-isoquinolin-1-one, 2-(2-biphenylmethyl)-7-[4-(3,3-diphenyl-1-propyl) piperazin-1-yl]-3-3,4-dihydro-2H-isoquinolin-1-one, 7-[4-(3,3-diphenyl-1-propyl)piperazin-1-yl]-2-(tetrahydropyran-2-yl)methyl-3,4-dihydro-2H-isoquinolin-1-one, 7-[4-(3,3-diphenyl-1-propyl)piperazin-1-yl]-2-(thiazol-4-yl)methyl-3,4-dihydro-2H-isoquinolin-1-one, 7-[4-(3,3-diphenyl-1-propyl)piperazin-1-yl]-2-(4-methylthiazol-5-yl)methyl-3,4-dihydro-2H-isoquinolin-1-one, 7-[4-(3,3-diphenyl-1-propyl)piperazin-1-yl]-2-(pyridine-4-yl)methyl-3,4-dihydro-2H-isoquinolin-1-one, 7-[4-(3,3-diphenyl-1-propyl)piperazin-1-yl]-2-(pyridine-2-yl)methyl-3,4-dihydro-2H-isoquinolin-1-one, and 2-benzyl-7-[4-(3,3-diphenyl-1-propyl)piperazin-1-yl]-4,4-dimethyl-3,4-dihydro-2H-isoquinolin-1-one.

The compounds according to the present invention may exist as salts. Preferred salts include pharmaceutically acceptable nontoxic salts, for example, lithium, sodium, potassium, magnesium, and calcium salts, salts with ammonia and suitable nontoxic amines, for example, $C_1$–$C_6$ alkylamines (for example, triethylamine) salts, $C_1$–$C_6$ alkanolamines (for example, diethanolamine or triethanolamine) salts, procaine salts, cyclohexylamine (for example, dicyclohexylamine) salts, benzylamine (for example, N-methylbenzylamine, N-ethylbenzylamine, N-benzyl-β-phenetylamine, N,N-dibenzylethylenediamine or dibenzylamine) salts, and heterocyclic amines (for example, morpholine or N-ethylpyridine) salts, hydrohalogenic acid salts, such as hydrofluoride salts, hydrochloride salts, hydrobromide salts, and hydroiodide salts, inorganic acid salts, such as sulfuric acid salts, nitric acid salts, phosphoric acid salts, perchloric acid salts, and carbonic acid salts, carboxylic acid salts, such as acetic acid salts, trichloroacetic acid salts, trifluoroacetic acid salts, hydroxyacetic acid salts, lactic acid salts, citric acid salts, tartaric acid salts, oxalic acid salts, benzoic acid salts, mandelic acid salts, butyric acid salts, maleic acid salts, propionic acid salts, formic acid salts, and malic acid salts, amino acid salts, such as alginic acid salts, aspartic acid salts, and glutamic acid salts, and other organic acid salts, such as methanesulfonic acid salts and p-toluenesulfonic acid salts. Preferred are acid addition salts, such as trifluoroacetic acid salts, hydrochloric acid salts, sulfuric acid salts, oxalic acid salts, methanesulfonic acid salts, and citric acid salts, and amino acid salts, such as glutamic acid salts and aspartic acid salts.

The compounds according to the present invention may exist as solvates. Preferred solvates include hydrates of the compounds and solvation products between the compounds and ethanol.

Use of Compounds Represented by Formula (I)/ Pharmaceutical Composition

The compounds represented by formula (I) and pharmacologically acceptable salts and solvates thereof according to the present invention have triglyceride biosynthesis inhibitory activity and inhibitory activity against secretion of apolipoprotein B-containing lipoproteins in liver. Therefore, the compounds according to the present invention can lower the amount of serum triglycerides and serum apolipoprotein B-containing lipoproteins, and thus can be used as prophylactic or therapeutic agents for hyperlipidemia (particularly hyper-very-low-density-lipoproteinemia) and/or arteriosclerotic diseases, such as cardiac infarction, or pancreatitis induced by hyperlipidemia. The compounds represented by formula (I) according to the present invention are especially advantageous in that they inhibit biosynthesis of lipids within hepatic cells and hence are not considered to have such side effect as will cause accumulation of hepatolipids.

The compounds and pharmacologically acceptable salts and solvates thereof according to the present invention may be administered to human beings and animals other than human beings by way of any one of routes including oral and parenteral administration, such as intravenous injection, intramuscular injection, subcutaneous administration, intraperitoneal administration, rectal administration, or percutaneous administration.

Accordingly, the compounds and pharmacologically acceptable salts and solvates thereof according to the present invention may be formed into appropriate dosage forms depending on its administration routes, and specifically prepared primarily into any one of the preparation forms including injections such as intravenous injection and intramuscular injection, preparations for oral administration such as capsules, tablets, granules, powders, pills, particulates, and troches, preparations for rectal administration, fatty suppositories, and aqueous suppositories.

These preparations can be prepared by conventional methods with ordinarily used excipients, fillers, binders, humidifiers, disintegrants, surface active agents, lubricants, dispersants, buffers, preservatives, dissolution aids, antiseptics, flavoring agents, analgesic agents, stabilizers and the like. Such non-toxic additives usable herein include, for example, lactose, fructose, glucose, starch, gelatin, magnesium carbonate, synthetic magnesium silicate, talc, magnesium stearate, methylcellulose or a salt thereof, gum arabic, polyethylene glycol, syrup, petrolatum, glycerol, ethanol, propylene glycol, citric acid, sodium chloride, sodium sulfite, and sodium phosphate.

The content of the compound according to the present invention in the pharmaceutical composition may vary according to its dosage forms. In general, however, the content of the compound may be about 1 to 70% by weight, preferably about 5 to 50% by weight, based on the whole composition.

The dosage may be appropriately determined in consideration of the dosage route and the age, sex, condition of patients and the like, and the preparation may be administered for the treatment of hyperlipidemia usually in an amount of about 0.1 to 5000 mg, preferably 1 to 600 mg per day per adult in one or several portions.

Synthesis of Compounds Represented by Formula (I)

Preferably, the compounds represented by formula (I) according to the present invention are synthesized by the following synthesis processes 1 to 10. In the following synthesis, protective groups or $C_1$–$C_4$ acyl groups on substituents may be if necessary introduced and removed by conventional means.

It will be apparent to a person having ordinary skill in the art that, in the following production processes, the order of synthesis may be determined so as not to cause any side reaction in functional groups not involved in the reaction and, in addition, functional groups may be protected by a suitable protective group in order to prevent the progress of unfavorable reactions.

Synthesis Process 1

Among the compounds represented by formula (I), compounds, wherein A represents group —$CH_2$— or —$CH_2CH_2$—, are preferably produced by the following process.

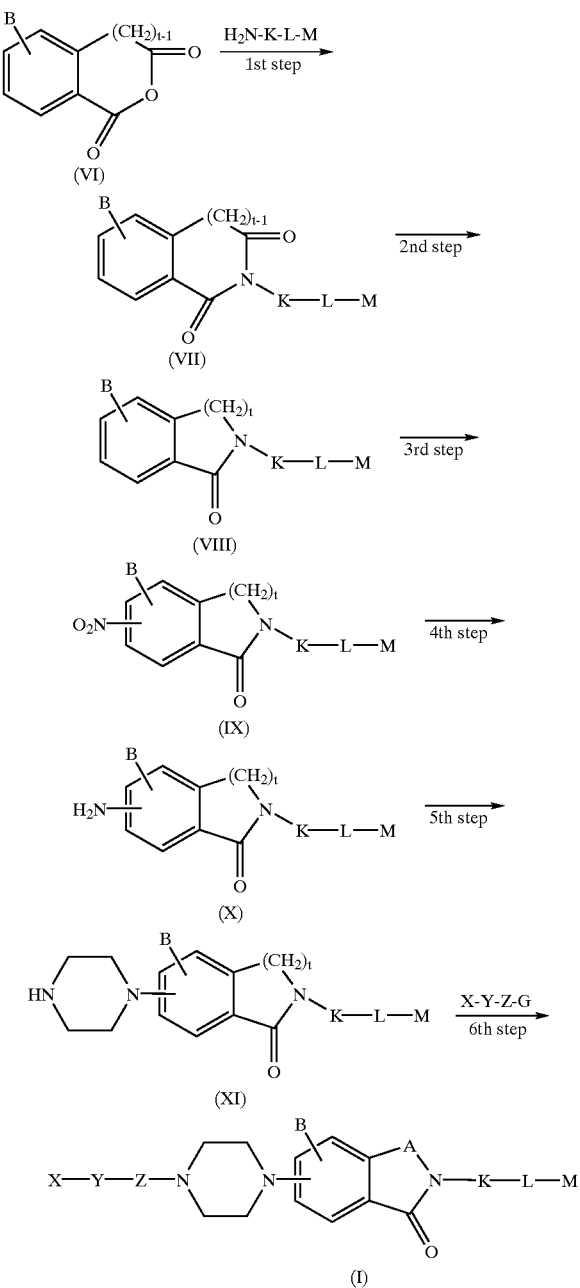

The first step is an imidation reaction of an acid anhydride. A compound represented by formula (VI), wherein t is an integer of 1 or 2 and B represents a hydrogen or halogen atom, may be reacted with a compound represented by formula $H_2N-K-L-M$, wherein K, L, and M each are as defined above in connection with formula (I), in the presence or absence of a base in a solvent not involved in the reaction (for example, tetrahydrofuran, benzene, toluene, or xylene) or under solvent-free conditions for 0.5 to 48 hr, preferably 1 to 24 hr, at 50 to 200° C., preferably 100 to 180° C., to obtain a compound represented by formula (VII) wherein t is an integer of 1 or 2 and B, K, L, and M each are as defined above in connection with formula (I).

The second step is a reduction reaction for converting the imide to a lactam. The compound represented by formula (VII) may be reduced in a solvent not involved in the reaction (for example, acetic acid, N,N-dimethylformamide, dimethyl sulfoxide, tetrahydrofuran, benzene, or toluene) in the presence of a reducing agent (for example, zinc-acetic acid, tin, sodium boron hydride, or zinc boron hydride) for 0.5 to 48 hr, preferably 1 to 24 hr, at 50 to 200° C, preferably 80–150° C., to obtain a compound represented by formula (VIII) wherein t, B, K, L, and M each are as defined above.

The third step is a nitration reaction. Conventional nitrating agents may be used in the nitration. The compound represented by formula (VIII) is reacted with a nitrating agent (preferably, nitric acid or potassium nitrate) in concentrated sulfuric acid for 0.5 to 48 hr, preferably 0.5 to 24 hr, at −20 to 100° C., preferably −20 to 50° C., to obtain a compound represented by formula (IX) wherein t, B, K, L, and M each are as defined above.

In the fourth step, the compound represented by formula (IX) is reduced to convert the nitro group to an amino group. Specifically, this conversion is carried out by catalytic reduction in the presence of palladium-carbon, palladium black, palladium hydroxide, platinum oxide, or Raney nickel, a reduction reaction using tin, zinc, iron or the like and an acid, such as acetic acid, or reduction with sodium boron hydride or hydrazine, preferably catalytic reduction in the presence of palladium-carbon or palladium black or a reduction reaction with iron and acetic acid, in a solvent not involved in the reaction (for example, methanol, ethanol, tetrahydrofuran, N,N-dimethylformamide, or benzene) for 0.5 to 48 hr, preferably for 0.5 to 30 hr, at 0 to 100° C., preferably 0 to 50° C., to obtain a compound represented by formula (X) wherein t, B, K, L, and M each are as defined above.

The fifth step is piperazination of the amine. The compound represented by formula (X) is reacted in the presence of 1 to 5 equivalents of bischloroethylamine and in the presence or absence of 1 to 3 equivalents of an acid, such as hydrochloric acid, in a solvent not involved in the reaction (for example, n-butanol, xylene, or toluene) for 0.5 hr to 7 days, preferably 1 hr to 5 days, at 50 to 200° C., preferably 60 to 180° C., to obtain a compound represented by formula (XI) wherein t, B, K, L, and M each are as defined above.

The sixth step is a condensation reaction with a compound represented by formula X—Y—Z—G. This reaction may be carried out by any one of the following methods (i) to (iii).

Method (i): A compound represented by formula X—Y—Z—G, wherein G represents a halogen atom, such as chlorine, bromine, or iodine, $C_1$-$C_4$ alkylsulfonyl such as methanesulfonyl, or arylsulfonyl, such as p-toluenesulfonyl, X and Y each are as defined above in connection with formula (I), and Z represents a bond, is reacted with the compound represented by formula (XI) in the presence or absence of a base in a solvent not involved in the reaction (for example, dichloromethane, tetrahydrofuran, N,N-dimethylformamide, or dimethyl sulfoxide) for 10 min to 48 hr, preferably 10 min to 24 hr, at −20 to 150° C., preferably0–100° C., to obtain a compound represented by formula (I) wherein A represents —$CH_2$— or —$CH_2CH_2$—, B, K, L, M, X, and Y each are as defined above in connection with formula (I), and Z represents a bond).

Method (ii): The compound represented by formula X—Y—Z—G, wherein X and Y are as defined in connection with formula (I), Z represents carbonyl or, together with group G, represents a carboxylic acid residue which has been activated by an acid halide, an acid anhydride or an activator, is reacted with the compound represented by formula (XI) in the presence or absence of a base in a solvent not involved in the reaction (for example, dichloromethane, tetrahydrofuran, N,N-dimethylformamide, or dioxane) for 1 min to 48 hr, preferably 1 min to 24 hr, at −20 to 100° C., preferably 0 to 50° C., to obtain a compound represented by formula (I) wherein A represents —CH$_2$— or —CH$_2$CH$_2$—, B, K, L, M, X, and Y each are as defined above in connection with formula (I), and Z represents carbonyl.

Method (iii): When the compound represented by formula X—Y—Z—G is X—(CH$_2$)$_{(q-1)}$—CHO wherein q represents an integer of 1 to 6 and X is as defined above in connection with formula (I), this compound and the compound represented by formula (XI) may be subjected to reductive alkylation with 1 to 5 equivalents of a reducing agent, for example, a metal hydride reagent, such as sodium boron cyanohydride, lithium boron cyanohydride, sodium boron hydride, lithium boron hydride, or sodium boron triacetoxyhydride) in the presence or absence of 0.1 to 5 equivalents of an acid, such as acetic acid or hydrochloric acid, in a solvent not involved in the reaction (for example, dichloroethane, dichloromethane, or tetrahydrofuran) for 0.5 to 48 hr, preferably 1 to 24 hr, at −20 to 100° C., preferably 0 to 70° C., to obtain a compound represented by formula (I) wherein A represents —CH$_2$— or —CH$_2$CH$_2$—, B, K, L, M, and X each are defined above in connection with formula (I), Y represents —(CH$_2$)$_q$— wherein q is an integer of 1 to 6, and Z represents a bond.

The compound represented by formula (VIII), wherein A represents —CH$_2$CH$_2$—, may also be synthesized by the method described in "Yakugaku Zasshi, 96, 176–179 (1976).

Bases usable in the reaction in synthesis process 1 include pyridine, triethylamine, N-methylmorpholine, and dimethylaminopyridine. Preferably, the base is used in an amount of 0.1 to 5 equivalents.

Preferred activators for carboxylic acids in the condensation of the compound represented by formula (XI) with the compound represented by X—Y—Z—G in method (ii) include 1,3-dicyclohexylcarbodiimide and 1-(3-dimethylaminopropyl)-3-ethylcarbodiimide.

Synthesis Process 2

As described below, among the compounds represented by formula (I), compounds, wherein B represents a halogen atom, may be produced by halogenating a corresponding compound wherein B represents a hydrogen atom.

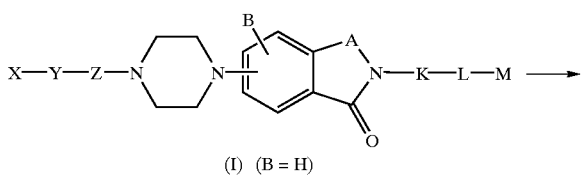

(I) (B = H)

-continued

X—Y—Z—N⟨piperazine⟩N—⟨ring B⟩—N—K—L—M (I) (B = halogen)

Specifically, the compound represented by formula (I), wherein A, K, L, M, X, Y, and Z each are as defined above in connection with formula (I) and B represents a hydrogen atom), is halogenated using a radical initiator (for example, N-halosuccinimide, preferably N-chlorosuccinimide, or N-bromosuccinimide) preferably in the presence of 0.01 to 3 equivalents of 2,2'-azobisisobutyronitrile in a solvent not involved in the reaction (for example, carbon tetrachloride, tetrahydrofuran, or benzene) for 0.5 to 48 hr, preferably for 1 to 24 hr, at −20 to 150° C., preferably at 0 to 120° C. to give the compound represented by formula (I) wherein B represents a halogen atom.

Synthesis Process 3

Among the compounds represented by formula (I), compounds, wherein A represents —CH=CH—, may be produced by dehydrogenating corresponding compounds wherein A represents —CH$_2$CH$_2$—.

X—Y—Z—N⟨piperazine⟩N—⟨ring B⟩—N—K—L—M ⟶

(I) (A = -CH$_2$CH$_2$-)

X—Y—Z—N⟨piperazine⟩N—⟨ring B⟩—N—K—L—M (I) (A = -CH = CH-)

Specifically, according to the method described in J. Med. Chem. 39, 4583–4591 (1996), the compound represented by formula (I), wherein B, K, L, M, X, Y, and Z each are as defined above in connection with formula (I) and A represents —CH$_2$CH$_2$—, may be dehydrogenated in the presence of palladium-carbon or palladium black in a solvent not involved in the reaction (for example, methanol, ethanol, tetrahydrofuran, N,N-dimethylformamide, or benzene) for 0.5 to 48 hr, preferably for 0.5 to 30 hr, at 0 to 100° C., preferably at 0 to 80° C. to give the compound represented by formula (I) wherein A represents —CH=CH—.

Synthesis Process 4

Among the compounds represented by formula (I), compounds, wherein A represents group —CH$_2$— or —CH$_2$CH$_2$—, may also be produced preferably through route A or route B.

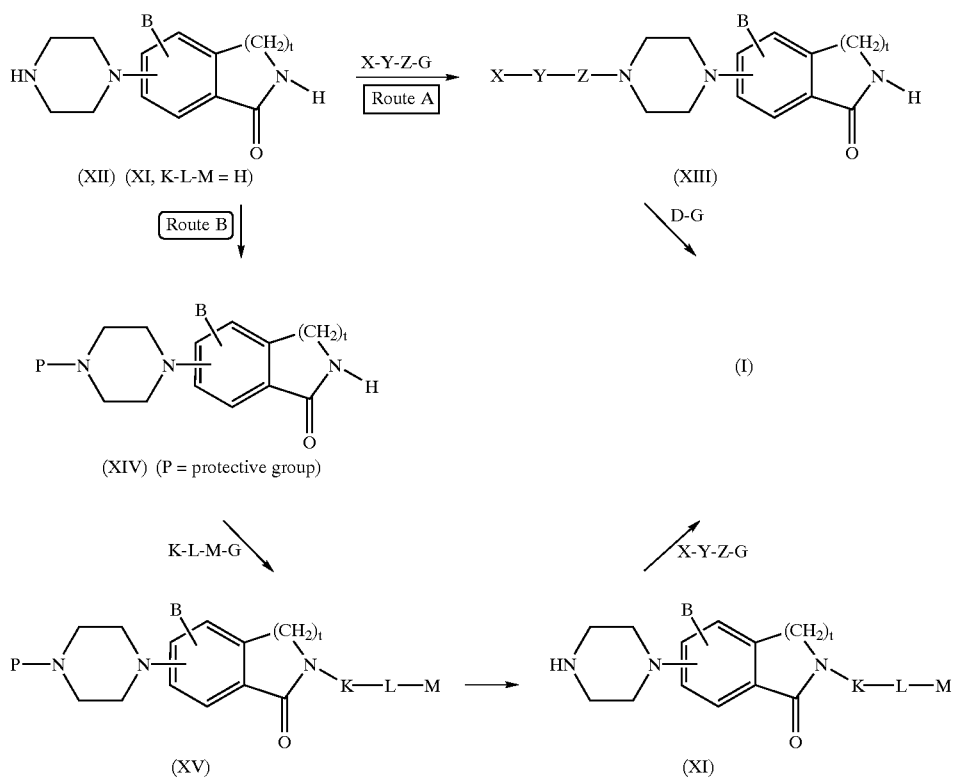

Route A

According to step 6 in synthesis process 1, a compound represented by formula (XII), wherein t is an integer of 1 or 2 and B is as defined above in connection with formula (I), is condensed with a compound represented by formula X—Y—Z—G wherein X, Y, and Z each are as defined above in connection with formula (I), G represents a halogen atom, such as chlorine, bromine, or iodine, $C_1$–$C_4$ alkylsulfonyl, such as methanesulfonyl, or arylsulfonyl, such as p-toluenesulfonyl, thereby providing a compound represented by formula (XIII) wherein t is an integer of 1 or 2, B, X, Y, and Z each are as defined as above in connection with formula (I).

Next, according to the description of J. Med. Chem. 39, 4583–4591 (1996) or Synthesis, 79, 527–529 (1979), the compound represented by formula (XIII) is reacted with a compound represented by formula G—K—L—M wherein G represents a halogen atom, such as chlorine, bromine, or iodine, $C_1$–$C_4$ alkylsulfonyl, such as methanesulfonyl, arylsulfonyl, such as p-toluenesulfonyl, and K, L, and M each are as defined above in connection with formula (I), thereby providing the compound represented by formula (I) wherein A represents group —$CH_2$— or —$CH_2CH_2$—.

Route B

The compound represented by formula (XII) in its piperazine is protected by a protective group, followed by a reaction according to the method described in J. Med. Chem. 39, 4583–4591 (1996). Protective groups usable for piperazine include conventional protective groups commonly used in synthesis of peptides, and preferred examples thereof include t-butoxycarbonyl, benzyloxycarbonyl, p-methoxybenzyloxycarbonyl, 2,2,2-trichloroethoxycarbonyl, trifluoroacetyl, allyloxycarbonyl and trityl. At the outset, the compound represented by formula (XII) in its piperazine portion is protected by a conventional method to give a compound represented by formula (XIV) wherein t is an integer of 1 or 2, B is as defined above in connection with formula (I) and P represents a protective group of amino. Next, the compound represented by formula (XIV) is reacted with a compound represented by formula G—K—L—M, wherein G, K, L, and M each are as defined above in connection with route A, according the method described in the literature noted above, thereby providing a compound represented by formula (XV). The protective group in the compound represented by formula (XV) is removed by a conventional method to give a compound represented by formula (XI). The compound represented by formula (XI) is condensed with a compound represented by formula X—Y—Z—G, wherein X, Y, Z, and G each are as defined above in connection with route A, according to step 6 in synthesis process 1, thereby providing the compound represented by formula (I) wherein A represents group —$CH_2$— or —$CH_2CH_2$—.

Synthesis Process 5

Among the compounds represented by formula (I), compounds, wherein A represents group —$CH_2$— or —$CH_2CH_2$—, may also be produced preferably by the following process.

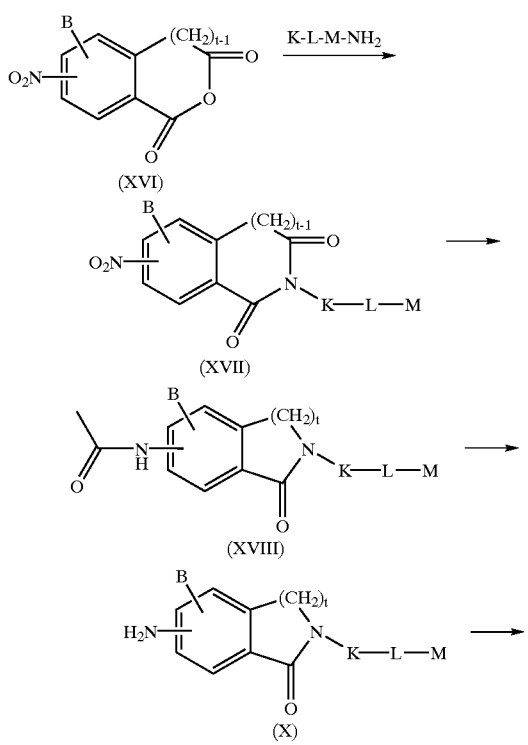

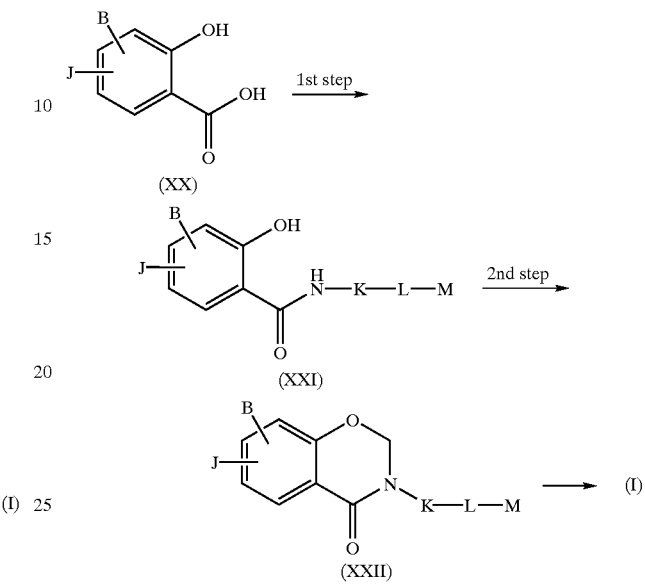

Synthesis Process 7

Among the compounds represented by formula (I), compounds, wherein A represents group —OCH$_2$—, are preferably produced by the following process.

A compound represented by formula (XVI), wherein t is an integer of 1 or 2 and B is as defined above in connection with formula (I), is reacted with a compound represented by formula H$_2$N—K—L—M according to step 1 in synthesis process 1, thereby providing a compound represented by formula (XVII). The compound represented by formula (XVII) is then subjected to a reduction reaction using zinc and acetic acid according to step 2 in synthesis process 1 to give a compound represented by formula (XVIII). The acetamide thus obtained is hydrolyzed under acidic conditions to give a compound represented by formula (X). Thereafter, the compound represented by formula (I), wherein A represents group —CH$_2$— or —CH$_2$CH$_2$—, may be produced according to step 5 and later steps in synthesis process 1.

Synthesis Process 6

Among compounds represented by formula (I), compounds wherein A represents group —CR$^1$R$^2$—, where R$^1$ and R$^2$ each represent C$_1$–C$_6$ alkyl, may be synthesized by producing a compound represented by formula (XIX) according to the method described in Angew. Chem. Int. Ed. Engl. 7, 373 (1968) and then subjecting the compound represented by formula (XIX) to step 3 and later steps in synthesis process 1 or the method in synthesis process 4:

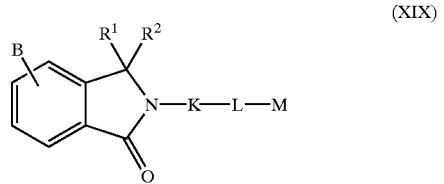

wherein R$^1$ and R$^2$ each represent C$_1$–C$_6$ alkyl and B, K, L, and M each are as defined above in connection with formula (I).

A compound represented by formula (XX), wherein J represents a hydrogen atom or nitro and B is as defined above in connection with formula (I), is amidated by the method described in Nobuo Izumiya et al., "Peptide Gosei no Kiso to Jikken (Bases and Experiments on Synthesis of Peptides)" (published by Maruzen Co., Ltd.) to obtain a compound represented by formula (XXI) wherein J is as defined above and B, K, L, and M each are as defined above in connection with formula (I). Next, this compound represented by formula (XXI) is converted to a compound represented by formula (XXII), wherein J is as defined above and B, K, L, and M each are as defined above in connection with formula (I), according to the method described in Tetrahedron, 48, 4963 (1992). The compound represented by formula (XXII), wherein J represents a hydrogen atom, is nitrated according to step 3 in synthesis process 1. The compound represented by formula (XXII), wherein J represents nitro, is treated according to step 4 and later steps in synthesis process 1 to obtain the compound represented by formula (I) wherein A represents group —OCH$_2$—.

Synthesis Process 8

Among the compounds represented by formula (I), compounds, wherein A represents group —SCH$_2$—, are preferably produced by the following process.

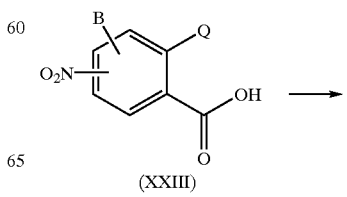

-continued

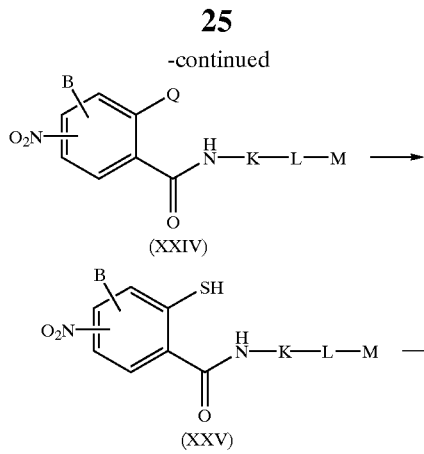

A compound represented by formula (XXIII), wherein Q represents a halogen atom and B is as defined above in connection with formula (I), is amidated by the method described in Nobuo Izumiya et al., "Peptide Gosei no Kiso to Jikken (Bases and Experiments on Synthesis of Peptides)" (published by Maruzen Co., Ltd.) to obtain a compound represented by formula (XXIV) wherein Q is as defined above and B, K, L, and M each are as defined above in connection with formula (I). Next, the compound represented by formula (XXIV) is reacted with 1 to 5 equivalents of potassium hydrosulfide or potassium thioacetate in a solvent not involved in the reaction (for example, ethanol, tetrahydrofuran, 1,4-dioxane, N,N-dimethylformamide, or acetonitrile), and, when potassium thioacetate is used, the reaction product is further hydrolyzed. Thus, a compound is obtained which is represented by formula (XXV) wherein B, K, L, and M each are as defined above in connection with formula (I). This reaction may be carried out at 0 to 200° C. for 1 to 72 hr, preferably at 50 to 150° C. for 1 to 48 hr. The compound represented by formula (XXV) is further treated in step 2 and later steps in synthesis process 7 to give the compound represented by formula (I) wherein A represents group —SCH$_2$—.

Synthesis Process 9

Among the compounds represented by formula (I), compounds, wherein K and L each represent a bond and M represents optionally substituted phenyl or an optionally substituted, saturated or unsaturated, five-membered or six-membered heterocyclic ring containing up to two hetero atoms, are preferably produced by the following process.

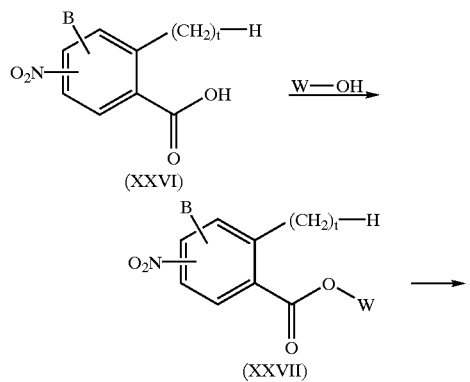

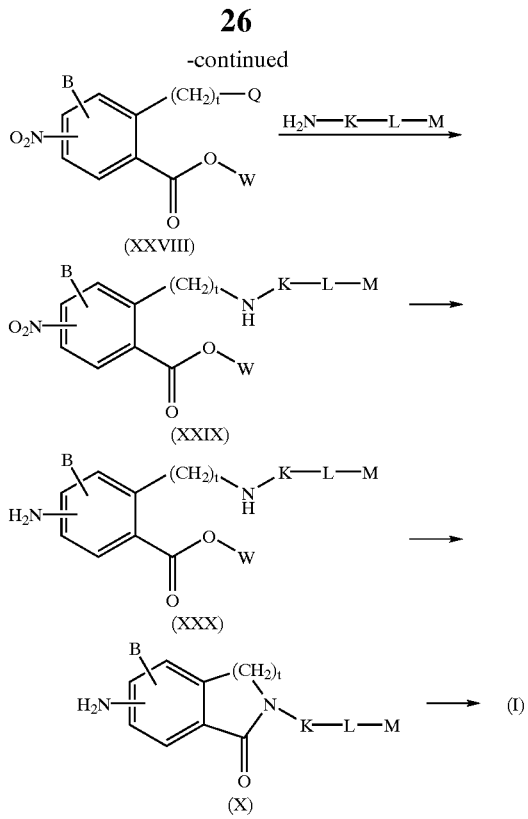

A compound represented by formula (XXVI), wherein t represents an integer of 1 or 2 and B is as defined above in connection with formula (I), and a compound represented by formula W—OH, wherein W represents C$_1$-C$_3$ alkyl, are esterified according to the method described in "Jikken Kagaku Koza 22," 4th edition, edited by The Chemical Society of Japan (published by Maruzen Co., Ltd.), pp. 43–47 to give a compound represented by formula (XXVII). Next, the compound represented by formula (XXVII) is halogenated according to the method described in "Jikken Kagaku Koza 19," 4th edition, edited by The Chemical Society of Japan(published by Maruzen Co., Ltd.), pp. 422–438 to give a compound represented by formula (XXVIII) wherein Q represents a halogen atom and t, B, and W each are as defined above. The compound represented by formula (XXVIII) is reacted with a compound represented by formula H$_2$N—K—L—M in the presence or absence of a base in a solvent not involved in the reaction (for example, methanol, ethanol, tetrahydrofuran, N,N-dimethylformamide, or dichloromethane) for 10 min to 48 hr, preferably 10 min to 24 hr, at −20 to 150° C., preferably at 0 to 100° C., to give a compound represented by formula (XXIX) wherein t, B, W, K, L, and M each are as defined above. The compound represented by formula (XXIX) is then reduced in the presence of palladium-carbon according to step 4 in synthesis process 1 to give a compound represented by formula (XXX) wherein t, B, W, K, L, and M each are as defined above. The compound represented by formula (XXX) is reacted in the presence or absence of a base or an acid in a solvent not involved in the reaction (for example, ethanol, tetrahydrofuran, N,N-dimethylformamide, dichloromethane, or toluene) for 10 min to 48 hr, preferably 10 min to: 24 hr, at −20 to 150° C., preferably at 0 to 100° C., to give a compound represented by formula (X) wherein t, B, K, L, and M each are as defined above. The compound represented by formula (X) may be then treated by step 5 and later steps in synthesis process 1 to give the compound repressed by formula (I) wherein K and L represent a bond and M represents an optionally substituted phenyl or an optionally substituted, saturated or unsaturated, five-membered or six-membered heterocyclic ring containing up to two hetero atoms.

Synthesis Process 10

Among the compounds represented by formula (I), compounds, wherein A represents group —$CR^1R^2$—$CH_2$— wherein $R^1$ and $R^2$ each represent $C_1$–$C_6$ alkyl, are preferably produced by synthesizing a compound represented by formula (XXXI) according to the method described in J. Heterocycl. Chem. 7, 615 (1970) and then treating the compound represented by formula (XXXI) according to step 3 and later steps in synthesis process 1 or alternatively the synthesis process 4:

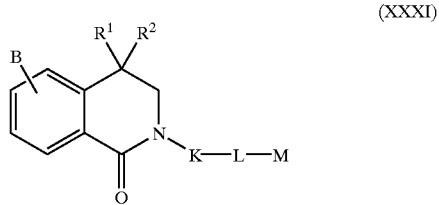

(XXXI)

wherein $R^1$ and $R^2$ each represent $C_1$–$C_6$ alkyl; and B is as defined above in connection with formula (I).

EXAMPLES

The following examples further illustrate the present invention, but are not intended to limit it.

Example 1

6-[4-(Benzyl)piperazin-1-yl]-2-cyclohexyl-2,3-dihydro-1H-isoindol-1-one (a) Cyclohexylamine (50.20 ml, 0.44 mol) and triethylamine (51.76 ml, 0.37 mol) were added to a suspension of phthalic anhydride (50.00 g, 0.34 mol) in toluene (500 ml) at room temperature. The mixture was stirred at 110° C. overnight. The temperature of the system was then returned to room temperature, and a 0.1 N aqueous citric acid solution was added thereto. The mixture was extracted with ethyl acetate. The extract was washed with saturated saline and dried over an hydrous $MgSO_4$. The solvent was then removed by distillation under the reduced pressure. The precipitated crystals were collected by suction filtration, washed with hexane, and then dried to give 55.28 g (71%) of 2-cyclohexylphthalimide as a white crystalline product.

$^1$H-NMR(CDCl$_3$) δ: 1.24–1.45 (3H, m), 1.67–1.75 (3H, m), 1.85–1.89 (2H, m), 2.14–2.28 (2H, m), 4.06–4.17 (1H, m), 7.68–7.71 (2H, m), 7.80–7.83 (2H, m)

EIMS(M/Z): 229 (M$^+$)

(b) Zinc powder (63.19 g, 0.97 mol) was added at room temperature to a solution of the compound (22.93 g, 0.1 mol), obtained in step (a) just above, in acetic acid (500 ml). The mixture was stirred at 100° C. for 2 hr. The temperature of the system was returned to room temperature, followed by filtration through Celite. The solvent was removed from the filtrate by distillation under the reduced pressure. Ethyl acetate was added to the residue. The mixture was washed with water, a saturated aqueous NaHCO$_3$ solution, and saturated saline in that order, and then dried over anhydrous MgSO$_4$. The solvent was then removed by distillation under the reduced pressure. The precipitated crystals were collected by suction filtration, washed with hexane, and then dried to give 15.27 g (71%) of 2-cyclohexyl-2,3-dihydro-1H-isoindol-1-one as a white crystalline product.

$^1$H-NMR(CDCl$_3$) δ: 1.11–1.24 (1H, m), 1.40–1.55 (4H, m), 1.68–1.80 (1H, m), 1.80–1.94 (4H, m), 4.21–4.31 (1H, m), 4.35 (2H, s), 7.42–7.55 (3H, m), 7.84–7.87 (1H, m)

EIMS(M/Z): 215(M$^+$)

(c) The compound (50.00 g, 0.23 mol) obtained in step (b) just above was dissolved at 0° C. in concentrated sulfuric acid (413 ml). Potassium nitrate (36.63 g, 0.36 mol) was added to the solution. The mixture was stirred overnight while gradually raising the temperature from 0° C. to room temperature. The reaction solution was poured into ice water (2000 ml), and then extracted with ethyl acetate. The extract was then washed with water, a saturated aqueous NaHCO$_3$ solution, and saturated saline in that order, and then dried over anhydrous MgSO$_4$. The solvent was removed by distillation under the reduced pressure. The precipitated crystals were collected by suction filtration, washed with hexane, and then dried to give 49.78 g (82%) of 2-cyclohexyl-2,3-dihydro-6-nitro-1H-isoindol-1-one as a pale yellow crystalline product.

$^1$H-NMR(CDCl$_3$) δ: 1.15–1.25 (1H, m), 1.41–1.57 (4H, m), 1.73–1.79 (1H, m), 1.83–1.92 (4H, m), 4.24–4.31(1H, m), 4.48 (2H, s), 7.63 (1H, d, J=8.3 Hz), 8.41 (1H, dd, J=2.1, 8.3 Hz), 8.69 (1H, d, J=2.1 Hz)

EIMS(M/Z): 260(M$^+$)

(d) 5% palladium-carbon (1 g) was added at room temperature to absolution of the compound (26.03 g, 0.1 mol), obtained in step (c) just above, in methanol (250 ml), followed by catalytic reduction. After stirring at room temperature for 26 hr, the reaction solution was filtered through Celite. The solvent was removed from the filtrate by distillation under the reduced pressure. The precipitated crystals were collected by suction filtration, washed with hexane, and then dried to give 15.36 g (67%) of 6-amino-2-cyclohexyl-2,3-dihydro-1H-isoindol-1-one as a brown crystalline product.

$^1$H-NMR(CDCl$_3$) δ: 1.12–1.18 (1H, m), 1.42–1.53 (4H, m), 1.69–1.79 (1H, m), 1.83–1.86 (4H, m), 3.82 (2H, br s), 4.22 (1H, m), 4.24 (2H, s), 6.83 (1H, dd, J=2.3, 8.0 Hz), 7.12 (1H, d, J=2.3 Hz), 7.20 (1H, d, J=8.0 Hz)

EIMS(M/Z): 230(M$^+$)

(e) Bis(2-chloroethyl)amine hydrochloride (9.82 g, 55.0 mmol) was added at room temperature to a solution of the compound (11.52 g, 50.0 mmol), obtained in step(d) just above, in xylene (200 ml). The mixture was then stirred by means of a mechanical stirrer at 140° C. for 3 days. The temperature of the reaction solution was returned to room temperature, and a 1 N aqueous sodium hydroxide solution (200 ml) was added thereto. The mixture was extracted with ethyl acetate. The extract was washed with saturated saline, and then dried over anhydrous MgSO$_4$. The solvent was then removed by distillation under the reduced pressure. The precipitated crystals were collected by suction filtration, washed with hexane and diethyl ether in that order, and then dried to give 11.33 g (76%) of 2-cyclohexyl-2,3-dihydro-6-(piperazin-1-yl)-1H-isoindol-1-one as a pale yellow crystalline product.

$^1$H-NMR(CDCl$_3$) δ: 1.13–1.26 (1H, m), 1.43–1.54 (4H, m), 1.69–1.76 (1H, m), 1.80–1.90(4H, m), 3.04–3.08 (4H, m), 3.19–3.22 (4H, m), 4.25 (1H, m), 4.27 (2H, s), 7.11 (1H, dd, J=2.4, 8.4 Hz), 7.31 (1H, d, J=8.4 Hz), 7.36 (1H, d, J=2.4 Hz)

EIMS(M/Z): 299(M$^+$)

(f) Potassium carbonate (111 mg, 0.8 mmol) and benzyl bromide (0.048 ml, 0.4 mmol) were added at 0° C. to a solution of the compound (120 mg, 0.4 mmol), obtained in step (e) just above, in dichloromethane (2 ml). The mixture was stirred for one day while gradually raising the temperature from 0° C. to room temperature. A 0.1 N aqueous citric acid solution was then added thereto. The mixture was then extracted with ethyl acetate. The extract was washed with saturated saline, and then dried over anhydrous $MgSO_4$. The solvent was then removed by distillation under the reduced pressure. The residue was then purified by column chromatography on silica gel (hexane:ethyl acetate=1:1) to give 99 mg (64%) of the title compound.

$^1$H-NMR(CDCl$_3$) δ: 1.12–1.22 (1H, m), 1.38–1.53 (4H, m), 1.68–1.78 (1H, m), 1.78–1.86 (4H, m), 2.61–2.64 (4H, m), 3.23–3.26 (4H, m), 3.57 (2H, s), 4.23 (1H, m), 4.26 (2H, s), 7.09 (1H, dd, J=2.4, 8.3 Hz), 7.24–7.37 (7H, m)

ESIMS(M/Z): 390(M+H)$^+$

Example 2

6-[4-(4-Chlorobenzyl)piperazin-1-yl]-2-cyclohexyl-2,3-dihydro-1H-isoindol-1-one

The title compound was obtained in the same manner as in step (f) of Example 1, except that 4-chloro benzyl bromide was used instead of benzyl bromide.

$^1$H-NMR(CDCl$_3$) δ: 1.12–1.25 (1H, m), 1.38–1.53 (4H, m), 1.64–1.79 (1H, m), 1.80–1.86 (4H, m), 2.59–2.62 (4H, m), 3.22–3.26 (4H, m), 3.53 (2H, s), 4.24 (1H, m), 4.26 (2H, s), 7.09 (1H, dd, J=2.3, 8.4 Hz), 7.29–7.33 (5H, m), 7.35 (1H, d, J=2.3 Hz)

TSIMS(M/Z): 424(M+H)$^+$

Example 3

2-Cyclohexyl-2,3-dihydro-6-[4-(3-pyridylmethyl)piperazin-1-yl]-1H-isoindol-1-one The title compound was obtained in the same manner as in step (f) of Example 1, except that 3-pyridylmethyl chloride hydrochloride was used instead of benzyl bromide.

$^1$H-NMR(CDCl$_3$) δ: 1.13–1.26 (1H, m), 1.43–1.53 (4H, m), 1.69–1.80 (1H, m), 1.81–1.92 (4H, m), 2.62–2.65 (4H, m), 3.23–3.27 (4H, m), 3.59 (2H, s), 4.23 (1H, m), 4.26 (2H, s), 7.10 (1H, dd, J=2.3, 8.4 Hz), 7.29 (1H, d, J=7.8 Hz), 7.31 (1H, d, J=8.4 Hz), 7.35 (1H, d, J=2.3 Hz), 7.72 (1H, d, J=7.8 Hz), 8.52–8.58 (2H, m)

TSIMS(M/Z): 391(M+H)$^+$

Example 4

2-Cyclohexyl-2,3-dihydro-6-[4-(octadecyl)piperazin-1-yl]-1H-isoindol-1-one

The title compound was obtained in the same manner as in step(f) of Example 1, except that octadecyl bromide was used instead of benzyl bromide.

$^1$H-NMR(CDCl$_3$) δ: 0.88 (1H, t, J=6.7 Hz), 1.18–1.22 (1H, m), 1.25–1.31 (30H, m), 1.43–1.53 (6H, m), 1.70 (1H, m), 1.75–1.87 (4H, m), 2.36–2.41 (2H, m), 2.60–2.63 (4H, m), 3.24–3.28 (4H, m), 4.24 (1H, m), 4.26 (2H, s), 7.11 (1H, dd, J=2.3, 8.4 Hz), 7.31 (1H, d, J=8.4 Hz), 7.36 (1H, d, J=2.3 Hz)

TSIMS(M/Z): 552(M+H)$^+$

Example 5

2-Cyclohexyl-2,3-dihydro-6-[4-(trans,trans-farnesyl)piperazin-1-yl]-1H-isoindol-1-one The title compound was obtained in the same manner as in step(f) of Example 1, except that trans, trans-farnesyl bromide was used instead of benzyl bromide.

$^1$H-NMR(CDCl$_3$) δ: 1.15–1.19 (1H, m), 1.43–1.53 (4H, m), 1.61 (6H, s), 1.67 (3H, s), 1.68 (3H, s), 1.73–1.80 (1H, m), 1.81–1.94 (4H, m), 1.95–2.03 (2H, m), 2.05–2.18 (6H, m), 2.61–2.65 (4H, m), 3.05 (2H, d, J=6.9 Hz), 3.25–3.28 (4H, m), 4.25 (1H, m), 4.26 (2H, s), 5.07–5.12 (2H, m), 5.28–5.33 (1H, m), 7.11 (1H, dd, J=2.4, 8.3 Hz), 7.31 (1H, d, J=8.3 Hz), 7.36 (1H, d, J=2.4 Hz)

TSIMS(M/Z): 504(M+H)$^+$

Example 6

2-Cyclohexyl-2,3-dihydro-6-[4-(2-thenyl)piperazin-1-yl]-1H-isoindol-1-one

The title compound was obtained in the same manner as in step(f) of Example 1, except that 2-thenyl chloride was used instead of benzyl bromide.

$^1$H-NMR(CDCl$_3$) δ: 1.13–1.20 (1H, m), 1.43–1.53 (4H, m), 1.70–1.79 (1H, m), 1.80–1.92 (4H, m), 2.65–2.68 (4H, m), 3.25–3.28 (4H, m), 3.79 (2H, s), 4.24 (1H, m), 4.26 (2H, s), 6.95–6.98 (2H, m), 7.09 (1H, dd, J=2.3, 8.3 Hz), 7.25 (1H, m), 7.30 (1H, d, J=8.3 Hz), 7.35 (1H, d, J=2.3 Hz)

TSIMS(M/Z): 396(M+H)$^+$

Example 7

2-Cyclohexyl-6-[4-(cyclohexylmethyl)piperazin-1-yl]-2,3-dihydro-1H-isoindol-1-one The title compound was obtained in the same manner as in step(f) of Example 1, except that cyclohexylmethyl bromide was used instead of benzyl bromide.

$^1$H-NMR(CDCl$_3$) δ: 0.83–0.97 (2H, m), 1.10–1.33 (5H, m), 1.38–1.58 (5H, m), 1.63–1.92 (9H, m), 2.04–2.21 (2H, m), 2.54–2.58 (4H, m), 3.22–3.26 (4H, m), 4.23 (1H, m), 4.26 (2H, s), 7.10 (1H, dd, J=2.4, 8.5 Hz), 7.30 (1H, d, J=8.5 Hz), 7.35 (1H, d, J=2.4 Hz)

TSIMS(M/Z): 396(M+H)$^+$

Example 8

2-Cyclohexyl-2,3-dihydro-6-[4-(3,3-diphenyl-1-propyl)piperazin-1-yl]-1H-isoindol-1-one The title compound was obtained in the same manner as in step(f) of Example 1, except that 3,3-diphenyl-1-propyl bromide was used instead of benzyl bromide.

$^1$H-NMR(CDCl$_3$) δ: 1.19–1.23 (1H, m), 1.43–1.49 (4H, m), 1.69–1.74 (1H, m), 1.83–1.86 (4H, m), 2.27–2.36 (4H, m), 2.56–2.60 (4H, m), 3.22–3.26 (4H, m), 4.02 (1H, t, J=7.2 Hz), 4.25 (1H, m), 4.26 (2H, s), 7.19 (1H, dd, J=2.3, 8.3 Hz), 7.16–7.20 (2H, m), 7.25–7.28 (8H, m), 7.30 (1H, d, J=8.3 Hz), 7.35(1H, d, J=2.3 Hz)

TSIMS(M/Z): 494(M+H)$^+$

Example 9

2-Cyclohexyl-2,3-dihydro-6-[4-(4-methoxybenzyl)-piperazin-1-yl]-1H-isoindol-1-one The title compound was obtained in the same manner as in step (f) of Example 1, except that 4-methoxybenzyl chloride was used instead of benzyl bromide.

$^1$H-NMR(CDCl$_3$) δ: 1.18–1.25 (1H, m), 1.43–1.53 (4H, m), 1.69–1.77 (1H, m), 1.81–1.86 (4H, m), 2.59–2.62 (4H, m), 3.22–3.26 (4H, m), 3.51 (2H, s), 3.81 (3H, s), 4.23 (1H, m), 4.26 (2H, s), 6.86–6.90 (2H, m), 7.09 (1H, dd, J=2.3, 8.4 Hz), 7.24–7.31 (3H, m), 7.34 (1H, d, J=2.3 Hz)

TSIMS(M/Z): 420(M+H)$^+$

Example 10

2-Cyclohexyl-2,3-dihydro-6-[4-(isoprenyl)piperazin-1-yl]-1H-isoindol-1-one

Title compound was obtained in the same manner as in step(f) of Example 1, except that isoprenyl bromide was used instead of benzyl bromide.

$^1$H-NMR(CDCl$_3$) δ: 7.38–7.25 (2H, m), 7.11 (1H, m), 5.32 (1H, brs), 4.23 (2H, s), 4.22 (1H, brs), 3.28 (4H, t, J=4.5 Hz), 3.16 (2H, d, J=7.0 Hz), 2.66 (4H, t, J=4.5 Hz), 1.93–0.97 (16H, m)

ESIMS(m/z): 368(M+H)$^+$

Example 11

2-Cyclohexyl-2,3-dihydro-6-[4-(geranyl)piperazin-1-yl]-1H-isoindol-1-one

The title compound was obtained in the same manner as in step(f) of Example 1, except that geranyl bromide was used instead of benzyl bromide.

$^1$H-NMR(CDCl$_3$) δ: 7.36 (1H, d, J=2.4 Hz), 7.31 (1H, d, J=7.1 Hz), 7.15 (1H, dd, J=2.2, 8.0 Hz), 5.30 (1H, m), 5.10 (1H, m), 4.27 (2H, s), 4.25 (1H, brs), 3.26 (4H, t, J=4.5 Hz), 3.04 (2H, d, J=7.1 Hz), 2.63 (4H, t, J=5.2 Hz), 2.11 (2H, m), 1.76 (2H, m)

ESIMS(m/z): 436(M+H)$^+$

Example 12

2-Cyclohexyl-2,3-dihydro-6-[4-(4-fluorobenzyl)-piperazin-1-yl]-1H-isoindol-1-one The title compound was obtained in the same manner as in step(f) of Example 1, except that 4-fluoro benzyl bromide was used instead of benzyl bromide.

$^1$H-NMR(CDCl$_3$) δ: 7.36–7.28 (4H, m), 7.12–6.98 (3H, m), 4.27 (2H, s), 4.23 (1H, brs), 3.53 (4H, t, J=4.7 Hz), 2.60 (4H, t, J=4.7 Hz), 1.83–1.18 (10H, m)

EIMS(m/z): 407(M$^+$)

Example 13

2-Cyclohexyl-2,3-dihydro-6-[4-(4-nitrobenzyl)-piperazin-1-yl]-1H-isoindol-1-one

The title compound was obtained in the same manner as in step (f) of Example 1, except that 4-nitro benzyl bromide was used instead of benzyl bromide.

$^1$H-NMR(CDCl$_3$) δ: 8.21 (2H, d, J=8.6 Hz), 7.55 (2H, d, J=8.6 Hz), 7.36 (2H, m), 7.13 (1H, dd, J=2.3, 7.6 Hz), 4.27 (2H, s), 4.23 (1H, brs), 3.53 (4H, t, J=4.7 Hz), 2.60 (4H, t, J=4.7 Hz), 1.83–1.18 (10H, m)

FABMS(m/z): 435(M+H)$^+$

Example 14

2-Cyclohexyl-2,3-dihydro-6-[4-(benzhydryl)-piperazin-1-yl]-1H-isoindol-1-one

The title compound was obtained in the same manner as in step(f) of Example 1, except that benzhydryl bromide was used instead of benzyl bromide.

$^1$HNMR(CDCl$_3$) δ: 7.45 (4H, d, J=8.0 Hz), 7.34–7.25 (6H, m), 7.19 (2H, t, J=8.0 Hz), 7.07 (1H, dd, J=2.2, 8.3 Hz), 4.26 (4H, m), 3.23 (4H, t, J=4.7 Hz), 2.58 (4H, t, J=4.7 Hz), 1.83–1.18 (10H, m)

EIMS(m/z): 465(M$^+$)

Example 15

6-[4-(N,N-Dibenzylamino-2-ethyl)piperazin-1-yl]-2-cyclohexyl-2,3-dihydro-1H-isoindol-1-one The title compound was obtained in the same manner as in step(f) of Example 1, except that N,N-dibenzylaminoethyl chloride hydrochloride was used instead of benzyl bromide.

$^1$H-NMR(CDCl$_3$) δ: 1.17 (1H, m), 1.39–1.54 (4H, m), 1.69–1.80 (1H, m), 1.84–1.89 (4H, m), 2.53–2.56 (4H, m), 2.59–2.67 (4H, m), 3.18–3.21 (4H, m), 3.62 (4H, s), 4.24 (1H, m), 4.26 (2H, s), 7.08 (1H, dd, J=2.4, 8.4 Hz), 7.20–7.40 (12H, m)

TSIMS(M/Z): 523(M+H)$^+$

Example 16

2-Cyclohexyl-2,3-dihydro-6-[4-(3-phenyl-1-propyl)piperazin-1-yl]-1H-isoindol-1-one The title compound was obtained in the same manner as in step (f) of Example 1, except that 3-phenyl-1-propyl bromide was used instead of benzyl bromide.

$^1$H-NMR(CDCl$_3$) δ: 1.18 (1H, m), 1.43–1.53 (4H, m), 1.67–1.75 (1H, m), 1.81–1.92 (6H, m), 2.41–2.47 (2H, m), 2.60–2.70 (6H, m), 3.24–3.28 (4H, m), 4.25 (1H, m), 4.26 (2H, s), 7.11 (1H, dd, J=2.3, 8.4 Hz), 7.16–7.21 (3H, m), 7.27–7.32 (3H, m), 7.36 (1H, d, J=2.3 Hz)

TSIMS(M/Z): 418(M+H)$^+$

Example 17

6-[4-(Cinnamyl)piperazin-1-yl]-2-cyclohexyl-2,3-dihydro-1H-isoindol-1-one

The title compound was obtained in the same manner as in step(f) of Example 1, except that cinnamyl bromide was used instead of benzyl bromide.

$^1$H-NMR(CDCl$_3$) δ: 1.18 (1H, m), 1.43–1.64 (4H, m), 1.68–1.80 (1H, m), 1.84–1.87 (4H, m), 2.68–2.71 (4H, m), 3.22–3.30 (6H, m), 4.25 (1H, m), 4.27 (2H, s), 6.31 (1H, dt, J=6.7, 15.7 Hz), 6.57 (1H, d, J=15.7 Hz), 7.12 (1H, dd, J=2.3, 8.4 Hz), 7.22–7.41 (7H, m)

TSIMS(M/Z): 416(M+H)$^+$

Example 18

6-[4-(3-Chlorobenzyl)piperazin-1-yl]-2-cyclohexyl-2,3-dihydro-1H-isoindol-1-one

The title compound (14 mg) was obtained in the same manner as in step(f) of Example 1, except that the compound (30 mg) obtained in step (e) of Example 1 and 3-chlorobenzyl bromide (23 mg) were used.

$^1$H-NMR(CDCl$_3$) δ: 1.46 (10H, m), 2.62 (4H, t, J=5.0 Hz), 3.15 (4H, t, J=5.0 Hz), 3.54 (2H, s), 4.20 (1H, m), 4.26 (2H, s), 7.10 (1H, dd, J=2.5, 8.4 Hz), 6.90 (2H, m), 7.12 (2H, m), 7 .33 (4H, m)

FABMS(m/z): 424(M+H)$^+$

Example 19

6-[4-(4-Bromobenzyl)-piperazin-1-yl]-2-cyclohexyl-2,3-dihydro-1H-isoindol-1-one the title compound (45 mg) was obtained in the same manner as in step (f) of Example 1, except that the compound(30 mg) obtained in step (e) of Example 1 and 4-bromobenzyl bromide (30 mg) were used.

$^1$H-NMR(CDCl$_3$) δ: 1.60 (10H, m), 2.60 (4H, t, J=5.2 Hz), 3.24 (4H, t, J=5.2 Hz), 3.52 (2H, s), 4.22 (1H, m), 4.26 (2H, s), 7.09 (1H, dd, J=2.5, 8.4 Hz), 7.24 (2H, d, J=8.2 Hz), 7.30 (1H, d, J=8.4 Hz), 7.35 (1H, d, J=2.5 Hz), 7.45 (2H, d, J=8.2 Hz)

FABMS(m/z): 468(M+H)$^+$

Example 20

6-[4-(2-Chlorobenzyl)-piperazin-1-yl]-2-cyclohexyl-2,3-dihydro-1H-isoindol-1-one The title compound (37 mg) was obtained in the same manner as in step (f) of Example 1, except that the compound (30 mg) obtained in step (e) of Example 1 and 2-chlorobenzyl bromide (23 mg) were used.

$^1$H-NMR(CDCl$_3$) δ: 1.65 (10H, m), 2.70 (4H, t, J=4.9 Hz), 3.27 (4H, t, J=4.9 Hz), 3.70 (2H, s), 4.02 (1H, m), 4.02 (2H, s), 7.11 (1H, dd, J=1.9, 8.3 Hz), 7.30 (5H, m), 7.52 (1H, d, J=7.7 Hz)

FABMS(m/z): 424(M+H)$^+$

Example 21

2-Cyclohexyl-2,3-dihydro-6-(4-triphenylmethyl-piperazin-1-yl)-1H-isoindol-1-one

The title compound (49 mg) was obtained in the same manner as in step (f) of Example 1, except that the compound (30 mg) obtained in step (e) of Example 1 and triphenylmethyl chloride (33 mg) were used.

$^1$H-NMR(CDCl$_3$) δ: 1.57 (10H, m), 1.85 (4H, bs), 3.37 (4H, bs), 4.26 (3H, bs), 7.05 (1H, dd, J=2.0, 7.1 Hz), 7.18 (2H, m), 7.30 (9H, m), 7.52 (6H, m)

FABMS(m/z): 542(M+H)$^+$

Example 22

2-Cyclohexyl-6-[4-(3,4-dichlorobenzyl)piperazin-1-yl]-2,3-dihydro-1H-isoindol-1-one The title compound (32 mg) was obtained in the same manner as in step (f) of Example 1, except that the compound (30 mg) obtained in step (e) of Example 1 and 2-chlorobenzyl bromide (24 mg) were used.

$^1$H-NMR(CDCl$_3$) δ: 1.67 (10H, m), 2.60 (4H, t, J=5.1 Hz), 3.25 (4H, t, J=5.1 Hz), 3.51 (2H, s), 4.27 (3H, m), 7.10 (1H, dd, J=2.3, 8.3 Hz), 7.20 (1H, dd, J=2.0, 8.2 Hz), 7.31 (1H, d, J=8.3 Hz), 7.35 (1H, d, J=2.3 Hz), 7.41 (1H, d, J=8.2 Hz), 7.79 (1H, d, J=2.0 Hz)

EIMS(m/z): 457 (M$^+$)

Example 23

2-Cyclohexyl-6-[4-(4-biphenylmethyl)-piperazin-1-yl]-2,3-dihydro-1H-isoindol-1-one The title compound (43 mg) was obtained in the same manner as in step (f) of Example 1, except that the compound (30 mg) obtained instep (e) of Example 1 and 4-(chloromethyl)biphenyl (24 mg) were used.

$^1$H-NMR(CDCl$_3$) δ: 1.60 (10H, m), 2.67 (4H, t, J=4.7 Hz), 3.28 (4H, t, J=4.7 Hz), 3.63 (2H, s), 4.26 (1H, m), 4.27 (2H, s), 7.10 (1H, dd, J=2.3, 8.3 Hz), 7.30 (1H, d, J=8.3 Hz), 7.36 (2H, m), 7.45 (4H, m), 7.59 (4H, m)

TSIMS(m/z): 466(M+H)$^+$

Example 24

2-Cyclohexyl-2,3-dihydro-6-[4-(3,3-diphenyl-1-propyl)piperazin-1-yl]-5-fluoro-1H-isoindol-1-one 2-Cyclohexyl-2,3-dihydro-5-fluoro-6-(piperazin-1-yl)-1H-isoindol-1-one was synthesized using 4-fluorophthalic anhydride and cyclohexylamine according to step (a) and later steps of Example 1. In the same manner as in step (f) of Example 1, the title compound was obtained from this compound and 3,3-diphenylpropyl bromide.

$^1$H-NMR(CDCl$_3$) δ: 1.17 (1H, m), 1.42–1.54 (4H, m), 1.65–1.75 (1H, m), 1.80–1.90 (4H, m), 2.26–2.39 (4H, m), 2.59–2.62 (4H, m), 3.11–3.14 (4H, m), 4.02 (1H, t, J=7.2 Hz), 4.21 (1H, m), 4.26 (2H, s), 7.09 (1H, d, J=11.3 Hz), 7.12–7.22 (2H, m), 7.25–7.31 (8H, m), 7.42 (1H, d, J=7.9 Hz)

ESIMS(M/Z): 512(M+H)$^+$

Example 25

2-Cyclopropyl-2,3-dihydro-6-[4-(3,3-diphenyl-1-propyl)piperazin-1-yl]-1H-isoindol-1-one 2-Cyclopropyl-2,3-dihydro-6-(piperazin-1-yl)-1H-isoindol-1-one was synthesized from phthalic anhydride and cyclopropylamine in the same manner as in Example 1. In the same manner as in step (f) of Example 1, the title compound was obtained from this compound and 3,3-diphenylpropyl bromide.

$^1$H-NMR(CDCl$_3$) δ: 0.81–0.94 (4H, m), 2.26–2.37 (4H, m), 2.56–2.60 (4H, m), 2.89–2.95 (1H, m), 3.22–3.25 (4H, m), 4.02 (1H, t, J=7.1 Hz), 4.22 (2H, s), 7.09 (1H, dd, J=2.4, 8.4 Hz), 7.15–7.20 (2H, m), 7.22–7.29 (9H, m), 7.32 (1H, d, J=2.4 Hz)

TSIMS(M/Z): 452(M+H)$^+$

Example 26

2-(4-Acetoxy)cyclohexyl-2,3-dihydro-6-[4-(3,3-diphenyl-1-propyl)piperazin-1-yl]-1H-isoindol-1-one 2-(4-Acetoxy)cyclohexyl-2,3-dihydro-6-(piperazin-1-yl)-1H-isoindol-1-one was synthesized from phthalic anhydride and 4-hydroxycyclohexylamine hydrochloride in the same manner as in Example 1. In the same manner as in step (f) of Example 1, the title compound was obtained from this compound and 3,3-diphenylpropyl bromide.

$^1$H-NMR(CDCl$_3$) δ: 7.34–7.25 (10H, m), 7.14–7.20 (2H, m), 7.10 (1H, dd, J=2.3, 8.4 Hz), 4.70 (1H, brs), 4.28 (1H, brs), 4.21 (2H, s), 4.01 (1H, t, J=7.3 Hz), 3.25 (4H, t, J=4.7 Hz), 2.59 (4H, t, J=4.7 Hz), 2.31 (4H, brs), 2.19 (2H, brs), 2.13 (3H, s), 1.90 (2H, brs), 1.60 (4H, brq)

TSIMS(m/z): 502(M+H)$^+$

Example 27

2,3-Dihydro-6-[4-(3,3-diphenyl-1-propyl)piperazin-1-yl]-2-(4-hydroxy)cyclohexyl-1H-isoindol-1-one The compound (72 mg) obtained in Example 26 was dissolved in methanol (2 ml). Purified water (0.2 ml) and potassium carbonate (88 mg) were then added to the solution. The mixture was stirred at 30° C. for 2 hr. MEOH was removed by distillation using an evaporator under the reduced pressure. A saturated aqueous ammonium chloride solution (3 ml) was then added to the residue, followed by separation with ethyl acetate and water. The ethyl acetate layer was washed with an aqueous sodium chloride solution, was dried over magnesium sulfate, and then concentrated under the reduced pressure. The residue was purified by chromatography on silica gel (ethyl acetate:hexane=1:1) to give 34 mg of 2,3-dihydro-6-[4-(3,3-diphenyl-1-propyl)piperazin-1-yl]-2-(4-hydroxy)cyclohexyl-1H-isoindol-1-one.

$^1$H-NMR(CDCl$_3$) δ: 7.34–7.25 (10H, m), 7.14–7.20 (2H, m), 7.10 (1H, dd, J=2.3, 8.4 Hz), 4.20 (3H, brs), 4.01 (1H, t, J=7.3 Hz), 3.63 (1H, brs), 3.25 (4H, t, J=4.7 Hz), 2.59 (4H, t, J=4.7 Hz), 2.47 (1H, brs), 2.33 (4H, brs), 2.09 (2H, brq), 1.87 (2H, brd), 1.54 (4H, brq)

TSIMS(m/z): 510(M+H)$^+$

Example 28

6-[4-(Benzyloxycarbonyl)piperazin-1-yl]-2-cyclohexyl-2,3-dihydro-1H-isoindol-1-one Sodium hydrogencarbonate (67 mg, 0.8 mmol) and benzyloxycarbonyl chloride (0.063 ml, 0.44 mmol) were added at 0° C. to a solution of the compound (120 mg, 0.4 mmol), obtained in step (e) of Example 1, in dichloromethane (2 ml). The mixture was stirred for one day while gradually raising the temperature from 0° C. to room temperature. A 0.1 N aqueous citric acid solution was then added thereto. The mixture was then extracted with ethyl acetate. The extract was then washed with saturated saline, and dried over anhydrous MgSO$_4$. The solvent was then removed by distillation under the reduced pressure. The residue was purified by column chromatography on silica gel (hexane:ethyl acetate=1:1) to give 128 mg (74%) of the title compound.

$^1$H-NMR(CDCl$_3$) δ: 1.12–1.25 (1H, m), 1.39–1.53 (4H, m), 1.69–1.79 (1H, m), 1.80–1.87 (4H, m), 3.18–3.21 (4H, m), 3.66–3.70 (4H, m), 4.23 (1H, m), 4.27 (2H, s), 5.17 (2H, s), 7.10 (1H, dd, J=2.4, 8.4 Hz), 7.30–7.40 (7H, m)

ESIMS(M/Z): 434(M+H)$^+$

Example 29

2-Cyclohexyl-2,3-dihydro-6-[4-(ethoxycarbonyl)-piperazin-1-yl]-1H-isoindol-1-one In the same manner as in Example 28, the title compound was prepared from the compound obtained in step (e) of Example 1 and ethoxycarbonyl chloride.

$^1$H-NMR(CDCl$_3$) δ: 1.17–1.19 (1H, m), 1.29 (3H, t, J=7.1 Hz), 1.43–1.50 (4H, m), 1.70–1.75 (1H, m), 1.82–1.87 (4H, m), 3.17–3.21 (4H, m), 3.63–3.66 (4H, m), 4.18 (2H, q, J=7.1 Hz), 4.24 (1H, m), 4.28 (2H, s), 7.11 (1H, dd, J=2.3, 8.3 Hz), 7.33 (1H, d, J=8.3 Hz), 7.36 (1H, d, J=2.3 Hz)

TSIMS(M/Z): 372(M+H)$^+$

Example 30

6-[4-(t-Butoxycarbonyl)piperazin-1-yl]-2-cyclohexyl-2,3-dihydro-1H-isoindol-1-one In the same manner as in Example 28, the title compound was prepared from the compound obtained in step (e) of Example 1 and di-t-butyl dicarbonate.

$^1$H-NMR(CDCl$_3$) δ: 1.17–1.20 (1H, m), 1.43–1.58 (4H, m), 1.48 (9H, s), 1.69–1.77 (1H, m), 1.81–1.93 (4H, m), 3.16–3.19 (4H, m), 3.58–3.61 (4H, m), 4.24 (1H, m), 4.27 (2H, s), 7.11 (1H, dd, J=2.4, 8.4 Hz), 7.33 (1H, d, J=8.4 Hz), 7.36 (1H, d, J=2.4 Hz)

TSIMS(M/Z): 400(M+H)$^+$

Example 31

6-[4-(Benzoyl)piperazin-1-yl]-2-cyclohexyl-2,3-dihydro-1H-isoindol-1-one

In the same manner as in Example 28, the title compound was prepared from the compound obtained in step (e) of Example 1 and benzoyl chloride.

$^1$H-NMR(CDCl$_3$) δ: 1.18–1.26 (1H, m), 1.44–1.54 (4H, m), 1.70–1.81 (1H, m), 1.82–1.92 (4H, m), 3.16–3.33 (4H, m), 3.59–3.69 (2H, m), 3.90–3.99 (2H, m), 4.24 (1H, m), 4.29 (2H, s), 7.12 (1H, dd, J=2.3, 8.6 Hz), 7.35 (1H, d, J=8.6 Hz), 7.37 (1H, d, J=2.3 Hz), 7.45 (5H, s)

ESIMS(M/Z): 404(M+H)$^+$

Example 32

2-Cyclohexyl-2,3-dihydro-6-[4-(pivaloyl)piperazin-1-yl]-1H-isoindol-1-one

In the same manner as in Example 28, the title compound was prepared from the compound obtained in step(e) of Example 1 and pivaloyl chloride.

$^1$H-NMR(CDCl$_3$) δ: 7.34 (1H, d, J=2.2 Hz), 7.30 (2H, d, J=8.3 Hz), 7.18 (1H, dd, J=2.2, 8.3 Hz), 4.25 (2H, s), 4.20 (1H, Brs), 3.80 (4H, t, J=4.9 Hz), 3.18 (4H, t, J=4.9 Hz), 1.83–1.18 (19H, m)

ESMS(m/z): 384(M+H)$^+$

Example 33

6-[4-(Benzhydryloxycarbonyl)piperazin-1-yl]-2-cyclohexyl-2,3-dihydro-1H-isoindol-1-one In the same manner as in Example 28, the title compound was prepared from the compound obtained in step (e) of Example 1 and benzhydryloxycarbonyl azide.

$^1$H-NMR(CDCl$_3$) δ: 1.18 (1H, m), 1.40–1.54 (4H, m), 1.70–1.81 (1H, m), 1.84–1.87 (4H, m), 3.20–3.23 (4H, m), 3.64–3.84 (4H, m), 4.23 (1H, m), 4.27 (2H, s), 6.85 (1H, s), 7.11 (1H, dd, J=2.4, 8.4 Hz), 7.25–7.36 (12H, m)

TSIMS(M/Z): 510(M+H)$^+$

Example 34

2-Cyclohexyl-6-[4-(4-methoxybenzyloxycarbonyl)-piperazin-1-yl]-2,3-dihydro-1H-isoindol-1-one 4-Methoxybenzyl-S-(4,6-dimethylpyrimidin-2-yl)-thiocarbonate (34 mg) was added to a solution of the compound (30 mg) obtained in step (e) of Example 1 in methylene chloride (1 ml). The mixture was stirred at room temperature for 20 min. Water was added to the reaction solution. The mixture was then extracted with ethyl acetate. The extract was dried over anhydrous magnesium sulfate. The solvent was then removed by distillation. The residue was purified by column chromatography on silica gel (hexane:ethyl acetate=1:1) to give the title compound (45 mg).

$^1$H-NMR(CDCl$_3$) δ: 1.59 (10H, m), 3.16 (4H, bs), 3.67 (4H, bs), 3.82 (3H, s), 4.27 (3H, m), 5.10 (2H, s), 6.90 (2H, m), 7.12 (2H, m), 7.33 (4H, m)

ESIMS(m/z): 464(M+H)$^+$

Example 35

2-Cyclohexyl-2,3-dihydro-6-[4-(3,5-dimethoxy-4-hydroxybenzoyl)piperazin-1-yl]-1H-isoindol-1-one A solution of syringic acid (20 mg) in dry DMF (2 ml) was cooled to 0° C. 1-Ethyl-3-(3-dimethylaminopropyl)-carbodiimide hydrochloride (WSCI) and 1-hydroxybenztriazole hydrate (HOBt) were added thereto in that order. The mixture was stirred at 0° C. for one hr. The compound (30 mg) obtained in step (e) of Example 1 and triethylamine were added thereto in that order. The mixture was stirred at 0° C. for one hr, and then stirred at room temperature overnight. A saturated aqueous ammonium chloride solution (5 ml) was added thereto, followed by separation with ethyl acetate and water. The ethyl acetate layer was washed with an aqueous sodium chloride solution, dried over magnesium sulfate, and then concentrated under the reduced pressure. The residue was purified by chromatography on silica gel (chloroform:methanol=20:1) to give 42 mg of the title compound.

$^1$H-NMR(CDCl$_3$) δ: 8.03 (2H, s), 7.35–7.13 (2H, m), 6.72 (2H, d, J=2.2 Hz), 5.80 (1H, s), 4.29 (2H, s), 4.23 (1H, Brs), 3.93 (6H, s), 2.97 (4H, s), 2.89 (4H, s), 1.83–1.18 (10H, m)

ESMS(m/z): 480(M+H)$^+$

Example 36

2-Cyclohexyl-2,3-dihydro-6-[4-(pyridine-3-carbonyl)piperazin-1-yl]-1H-isoindol-1-one In the same manner as in Example 35, the title compound was prepared from the compound obtained in step (e) of Example 1 and nicotinic acid.

$^1$H-NMR(CDCl$_3$) δ: 8.72 (2H, m), 7.81 (1H, td, J=2.1, 7.7 Hz), 7.41 (3H, m), 7.12 (1H, dd, J=2.3, 8.3 Hz), 4.29 (2H, s), 4.24 (1H, Brs), 3.80 (4H, brd), 3.28 (4H, brd), 1.83–1.18 (10H, ESMS(m/z): 405(M+H)$^+$

Example 37

2-Cyclohexyl-2,3-dihydro-6-[4-diphenylacetyl-piperazin-1-yl]-1H-isoindol-1-one

In the same manner as in Example 35, the title compound was prepared from the compound obtained in step (e) of Example 1 and diphenyl acetate.

$^1$H-NMR(CDCl$_3$) δ: 7.34–7.22 (6H, m), 7.19 (2H, t, J=8.0 Hz), 7.07 (1H, dd, J=2.2, 8.3 Hz), 4.26 (4H, m), 3.23 (4H, t, J=4.7 Hz), 2.58 (4H, t, J=4.7 Hz), 1.83–1.18 (10H, m)

EIMS(m/z): 465(M$^+$)

Example 38

2-Cyclohexyl-2,3-dihydro-6-[4-(2,2-diphenylethyl)-piperazin-1-yl]-1H-isoindol-1-one Diphenylacetaldehyde (40 mg) was added to a solution of the compound (60 mg), obtained in step (e) of Example 1, in 1,2-dichloroethane (2 ml). The mixture was stirred at 0° C. Sodium boron triacetoxyhydride (44 mg) was added to the reaction solution, followed by stirring at 0° C. for one hr. The mixture was then stirred at room temperature overnight. A saturated aqueous ammonium chloride solution (5 ml) was then added thereto, followed by separation with ethyl acetate and water. The ethyl acetate layer was washed with an aqueous sodium chloride solution, dried over magnesium sulfate, and then concentrated under the reduced pressure. The residue was purified by chromatography on silica gel (ethyl acetate:hexane=1:1) to give 76 mg of the title compound.

$^1$H-NMR(CDCl$_3$) δ: 7.34–7.25 (9H, m), 7.23–7.16 (2H, m), 7.05 (2H, dd, J=2.0, 8.0 Hz), 4.23 (5H, m), 3.15 (4H, t, J=4.7 Hz) 2.65 (4H, t, J=4.7 Hz), 2.06 (2H, d, J=4.9 Hz), 1.83–1.18 (10H, m)

FABMS(m/z): 480(M+H)$^+$

Example 39

2-Cyclohexyl-2,3-dihydro-6-[4-(4-hydroxyphenyl)-methylpiperazin-1-yl]-1H-isoindol-1-one In the same manner as in Example 38, the title compound was prepared from the compound obtained in step (e) of Example 1 and 4-hydroxybenzaldehyde.

$^1$H-NMR(CDCl$_3$) δ: 1.16 (1H, m), 1.45 (4H, m), 1.71 (1H, br.d), 1.86 (4H, m), 2.58 (4H, m), 3.19 (4H, m), 3.47 (2H, s), 4.23 (1H, m), 4.27 (2H, s), 6.82 (2H, d, J=8.7), 7.09 (1H, dd, J=2.2, 8.3), 7.16 (2H, d, J=8.7), 7.29 (1H, d, J=8.3), 7.34 (1H, dd, J=2.2, 8.3)

FABMS(m/z): 406(M+H)$^+$

Example 40

2-Cyclohexyl-2,3-dihydro-6-[4-(4,4-diphenyl-1-butyl)piperazin-1-yl]-1H-isoindol-1-one In the same manner as in Example 38, the title compound was prepared from the compound obtained in step (e) of Example 1 and 4,4-diphenylbutylaldehyde.

$^1$H-NMR(CDCl$_3$) δ: 1.17 (1H, m), 1.38–1.60 (6H, m), 1.69–1.77 (1H, m), 1.78–1.86 (4H, m), 2.05–2.13 (2H, m), 2.41 (2H, t, J=7.5 Hz), 2.53–2.56 (4H, m), 3.20–3.24 (4H, m), 3.91 (1H, t, J=7.9 Hz), 4.24 (1H, m), 4.26 (2H, s), 7.09 (1H, dd, J=2.4, 8.3 Hz), 7.14–7.19 (2H, m), 7.20–7.31 (9H, m), 7.34 (1H, d, J=2.4 Hz)

TSIMS(M/Z): 508(M+H)$^+$

Example 41

2-Cyclohexyl-6-{4-[3,3-bis(4-methoxyphenyl)-1-propyl]-piperazin-1-yl}-2,3-dihydro-1H-isoindol-1-one (a) 10% Pd—C (20 mg) was added to a solution of 3,3-bis(4-methoxyphenyl)-propenenitrile (50 mg), synthesized by the process described in a literature J. Med. Chem., 32, 1820 (1989), in dioxane (5 ml), followed by hydrogenation for 2 hr. Pd—C was removed by filtration through Celite. The solvent was then removed by distillation to give 3,3-bis(4-methoxyphenyl)-propanenitrile (38 mg).

$^1$H-NMR(CDCl$_3$) δ: 2.98 (2H, d, J=7.7 Hz), 3.79 (6H, s), 4.30 (1H, t, J=7.7 Hz), 6.87 (4H, d, J=8.6 Hz), 7.15 (4H, d, J=8.6 Hz)

EIMS(m/z): 267 (M$^+$)

(b) A 1.5 M toluene solution (0.37 ml) of DIBAL-H was added to a solution of the compound (100 mg) obtained in step (a) in toluene (10 ml) under cooling at −40° C. The mixture was stirred for 2.5 hr. A 1 N aqueous HCl solution was added to the reaction solution. The mixture was extracted with ethyl acetate. The extract was dried over anhydrous magnesium sulfate. The solvent was then removed by distillation to give 3,3-bis(4-methoxyphenyl)-propanaldehyde.

$^1$H-NMR(CDCl$_3$) δ: 3.10 (2H, dd, J=1.9, 7.7 Hz), 3.79 (6H, s), 4.54 (1H, t, J=7.7 Hz), 6.87 (4H, d, J=8.8 Hz), 7.14 (4H, d, J=8.8 Hz), 9.73 (1H, t, J=1.9)

(c) In the same manner as in Example 38, the title compound (52 mg) was prepared from the compound (47 mg) obtained in step (e) of Example 1 and the compound (110 mg) obtained in step (b).

$^1$H-NMR(CDCl$_3$) δ: 1.47 (10H, m), 2.26 (4H, m), 2.59 (4H, t, J=4.6 Hz), 3.25 (4H, t, J=4.6 Hz), 3.78 (6H, s), 4.26 (1H, m), 4.27 (2H, s), 6.83 (4H, d, J=8.6 Hz), 8.78 (7H, m)

FABMS(m/z): 554(M+H)$^+$

Example 42

2-Cyclohexyl-6-{4-[3,3-bis(4-chlorophenyl)-1-propyl]-piperazin-1-yl}-2,3-dihydro-1H-isoindol-1-one (a) Diethyl cyanomethylphosphonate (1.95 g) was added to a solution of sodium (345 mg) dissolved, under cooling in an ice bath, in ethanol (30 ml). The mixture was heated under reflux for one hr. The reaction solution was concentrated under the reduced pressure. Water was added to the residue, and the mixture was extracted with ethyl acetate. The extract was dried over anhydrous magnesium sulfate. The solvent was then removed by distillation. The residue was purified by chromatography on silica gel (hexane:ethyl acetate=9:1) to give 3,3-bis(4-chlorophenyl)-propenenitrile (2.95 g).

$^1$H-NMR(CDCl$_3$) δ: 5.73 (1H, s), 7.23 (4H, d, J=8.8 Hz), 7.45 ($^4$H, d, J=8.8 Hz)

TSIMS (m/z): 275(M+H)$^+$ (b) Sodium boron hydride (756 mg) was added to a solution of the compound (550 mg), obtained in step (a) just above, in ethanol (20 ml) under cooling in an ice bath. The mixture was then heated under reflux for 1.5 hr. The reaction solution was concentrated under the reduced pressure. Water was added to the residue. The mixture was extracted with ethyl acetate, and then dried over anhydrous magnesium sulfate. The solvent was then removed by distillation. The residue was purified by chromatography on silica gel (hexane:ethyl acetate=9:1) to give 3,3-bis(4-chlorophenyl)-propanenitrile (311 mg).

$^1$H-NMR(CDCl$_3$) δ: 3.00 (2H, d, J=7.6 Hz), 4.35 (1H, t, J=7.6 Hz), 7.15 (4H, d, J=8.4 Hz), 7.33 (4H, d, J=8.4 Hz)

EIMS(m/z): 277(M+H)$^+$ (c) In the same manner as in Example 41, 3,3-bis(4-chlorophenyl)-propanaldehyde was prepared from a solution of the compound (100 mg), obtained in step (b), in tetrahydrofuran (10 ml).

$^1$H-NMR(CDCl$_3$) δ: 3.15 (2H, dd, J=1.6, 7.7 Hz), 4.59 (1H, t, J=7.7 Hz), 7.14 (4H, d, J=8.3 Hz), 7.28 (4H, d, J=8.3 Hz)

EIMS(m/z): 278(M$^+$)

(d) In the same manner as in Example 38, the title compound (52 mg) was prepared from the compound (69 mg) obtained in step (e) of Example 1 and the compound (78 mg) obtained in step (c) just above.

$^1$H-NMR (CDCl$_3$) δ: 1.46 (4H, m), 1.85 (6H, m), 2.30 (4H, m), 2.57 (4H, t, J=4.8 Hz), 3.24 (4H, t, J=4.8 Hz), 4.23 (1H, m), 4.26 (2H, s), 7.10 (1H, dd, J=2.2, 8.3 Hz), 7.15 (4H, d, J=8.5 Hz), 7.26 (4H, d, J=8.5 Hz), 7.30 (1H, d, J=8.3 Hz), 7.35 (1H, d, J=2.2 Hz)

PBCMS (m/z): 562(M+H)$^+$

Example 43

2-Cyclohexyl-2,3-dihydro-5-[4-(3,3-diphenyl-1-propyl)piperazin-1-yl]-1H-isoindol-1-one (a) In the same manner as in step (a) of Example 1, 2-cyclohexyl-5-nitrophthalimide was synthesized from 4-nitrophthalic anhydride and cyclohexylamine.

$^1$H-NMR(CDCl$_3$) δ: 1.19–1.49 (3H, m), 1.61–1.85 (3H, m), 1.88–2.08 (2H, m), 2.14–2.27 (2H, m), 4.11–4.21 (1H, m), 8.01 (1H, d, J=8.1 Hz), 8.58 (1H, dd, J=2.0, 8.1 Hz), 8.64 (1H, d, J=12.0 Hz)

EIMS(M/Z): 274(M$^+$)

(b) The compound obtained instep (a) just above was reduced in the same manner as in step (b) of Example 1 to obtain an about 4:1 mixture (92%) of 5-acetylamino-2-cyclohexyl-2,3-dihydro-1H-isoindol-1-one and 6-acetylamino-2-cyclohexyl-2,3-dihydro-1H-isoindol-1-one.

These position isomers cannot be isolated by column chromatography on silica gel. Therefore, after the formation of these isomers was confirmed by $^1$H-NMR and ESIMS, the following reaction was carried out. Specifically, concentrated hydrochloric acid (15 ml) was added at room temperature to a solution of the mixture of position isomers (0.953 g, 3.5 mmol) in 1,4-dioxane (15 ml). The mixture was stirred at 100° C. for one hr. The temperature of the reaction solution was returned to room temperature. The solvent was then removed by distillation under the reduced pressure. A saturated aqueous NaHCO$_3$ solution was then added to the residue. The mixture was extracted with ethyl acetate. The extract was washed with saturated saline, and then dried over anhydrous MgSO$_4$. The solvent was then removed by distillation under the reduced pressure. The residue was purified by column chromatography on ODS (methanol:water=3:1) to give 513 mg (64%) of 5-amino-2-cyclohexyl-2,3-dihydro-1H-isoindol-1-one and 113 mg (14%) of 6-amino-2-cyclohexyl-2,3-dihydro-1H-isoindol-1-one.

$^1$H-NMR(CDCl$_3$) δ: 1.16 (1H, m), 1.41–1.48 (4H, m), 1.71–1.78 (1H, m), 1.79–1.90 (4H, m), 4.00 (2H, brs), 4.19 (1H, m), 4.23 (2H, s), 6.67–6.71 (2H, m), 7.62 (1H, d, J=8.0 Hz)

TSIMS(M/Z): 231(M+H)$^+$ (c) In the same manner as in step (e) of Example 1, 2-cyclohexyl-2,3-dihydro-5-(piperazin-1-yl)-1H-isoindol-1-one was synthesized from 5-amino-2-cyclohexyl-2,3-dihydro-1H-isoindol-1-one obtained in step (b) just above and bis(2-chloroethyl)amine hydrochloride.

$^1$H-NMR(CDCl$_3$) δ: 1.17 (1H, m), 1.42–1.53 (4H, m), 1.71–1.80 (1H, m), 1.84–1.86 (4H, m), 3.03–3.07 (4H, m), 3.24–3.27 (4H, m), 4.21 (1H, m), 4.27 (2H, s), 6.90 (1H, s), 6.99 (1H, dd, J=2.1, 8.6 Hz), 7.70 (1H, d, J=8.6 Hz)

ESIMS(M/Z): 300(M+H)$^+$ (d) In the same manner as in step (f) of Example 1, the title compound was prepared from the compound obtained in step (c) just above and 3,3-diphenylpropyl bromide.

$^1$H-NMR(CDCl$_3$) δ: 1.17 (1H, m), 1.42–1.52 (4H, m), 1.67–1.79 (1H, m), 1.80–1.90 (4H, m), 2.27–2.38 (4H, m), 2.56–2.59 (4H, m), 3.27–3.30 (4H, m), 4.02 (1H, t, J=7.2 Hz), 4.20 (1H, m), 4.26 (2H, s), 6.88 (1H, s), 6.97 (1H, dd, J=1.9, 8.6 Hz), 7.15–7.24 (2H, m), 7.25–7.31 (8H, m), 7.69 (1H, d, J=8.6 Hz)

EIMS(M/Z): 493(M$^+$)

Example 44

2-Cyclohexyl-2,3-dihydro-5-[4-(trans,trans-farnesyl)piperazin-1-yl]-1H-isoindol-1-one In the same manner as in step (f) of Example 1, the title compound was obtained from the compound obtained in step (c) of Example: 43 and trans,trans-farnesyl bromide.

$^1$H-NMR(CDCl$_3$) δ: 1.17 (1H, m), 1.38–1.58 (4H, m), 1.60 (6H, s), 1.67 (3H, s), 1.68 (3H, s), 1.73–1.78 (1H, m), 1.79–1.85 (4H, m), 1.95–2.01 (2H, m), 2.03–2.17 (6H, m), 2.60–2.63 (4H, m), 3.05 (2H, d, J=6.9 Hz), 3.29–3.32 (4H, m)), 4.20 (1H, m), 4.27 (2H, s), 5.07–5.12 (2H, m), 5.28–5.32 (1H, m)), 6.89 (1H, br s), 6.98 (1H, dd, J=2.1, 8.6 Hz), 7.70 (1H, d, J=8.6 Hz)

EIMS(M/Z): 503(M$^+$)

Example 45

6-[4-(t-Butoxycarbonyl)piperazin-1-yl]-7-chloro-2-cyclohexyl-2,3-dihydro-1H-isoindol-1-one N-Chlorosuccinimide (87 mg, 0.65 mmol) and 2,2'-azobisisobutyronitrile (4 mg, 0.025 mmol) were added at room temperature to a solution of the compound (200 mg, 0.5 mmol), obtained in Example 30, in carbon tetrachloride (5 ml). The mixture was stirred at 90° C. for 4.5 hr. The temperature of the system was returned to room temperature. The solvent was then removed by distillation under the reduced pressure. The residue was diluted with diethyl ether. The diluted solution was washed with water, and then dried over anhydrous $MgSO_4$. The solvent was then removed by distillation under the reduced pressure. The residue was purified by preparative TLC (chloroform:ethyl acetate= 20:1) (number of times of development: three) to give 89 mg; (41%) of 6-[4-(t-butoxycarbonyl)piperazin-1-yl]-7-chloro-2-cyclohexyl-2,3-dihydro-1H-isoindol-1-one and 54 mg (25%) of 6-[4-(t-butoxycarbonyl)piperazin-1-yl]-5-chloro-2-cyclo-hexyl-2,3-dihydro-1H-isoindol-1-one.

$^1$H-NMR(CDCl$_3$) δ: 1.18 (1H, m), 1.42–1.63 (13H, m), 1.69–1.77 (1H, m), 1.80–1.92 (4H, m), 3.00–3.04 (4H, m), 3.61–3.65 (4H, m), 4.23 (1H, m), 4.25 (2H, s), 7.16 (1H, d, J=8.1 Hz), 7.28 (1H, d, J=8.1 Hz)

TSIMS(M/Z): 434(M+H)$^+$

Example 46

6-[4-(t-Butoxycarbonyl)piperazin-1-yl]-5-chloro-2-cyclohexyl-2,3-dihydro-1H-isoindol-1-one The title compound was obtained in the same manner as in Example 45.

$^1$H-NMR(CDCl$_3$) δ: 1.18 (1H, m), 1.43–1.61 (13H, m), 1.69–1.77 (1H, m), 1.81–1.91 (4H, m), 2.99–3.02 (4H, m), 3.60–3.63 (4H, m), 4.22 (1H, m), 4.28 (2H, s), 7.47 (1H, s), 7.50 (1H, s)

TSIMS(M/Z): 434(M+H)$^+$

Example 47

7-Chloro-2-cyclohexyl-2,3-dihydro-6-[4-(3,3-diphenyl-1-propyl)piperazin-1-yl]-1H-isoindol-1-one Trifluoroacetic acid (0.125 ml) was added at 0° C. to a solution of 6-[4-(t-butoxycarbonyl)piperazin-1-yl]-7-chloro-2-cyclohexyl-2,3-dihydro-1H-isoindol-1-one (43 mg, 0.1 mmol), obtained in Example 45, in dichloromethane (1 ml). The mixture was stirred at room temperature for 2 hr. The reaction solution was concentrated under the reduced pressure. A saturated aqueous NaHCO$_3$ solution was then added thereto. The mixture was extracted with chloroform. The extract was washed with saturated saline, and then dried over anhydrous MgSO$_4$. The solvent was then removed by distillation under the reduced pressure. Potassium carbonate (28 mg, 0.2 mmol) and 3,3-diphenylpropyl bromide (30 mg, 0.11 mmol) were added at 0° C. to a solution of the crude product, thus obtained, in N,N-dimethylformamide (1 ml). The mixture was stirred at 50° C. for 5 hr. The temperature of the system was then returned to room temperature, and a 0.1 N aqueous citric acid solution was added thereto. The mixture was extracted with ethyl acetate, washed with saturated saline, and then dried over anhydrous MgSO$_4$. The solvent was then removed by distillation under the reduced pressure. The residue was purified by preparative TLC (chloroform:methanol=30:1) to give 17 mg (32%) of the title compound.

$^1$H-NMR(CDCl$_3$) δ: 1.17 (1H, m), 1.42–1.52 (4H, m), 1.68–1.80 (1H, m) 1.81–1.87 (4H, m), 2.28–2.40 (4H, m), 2.60–2.69 (4H, m), 3.04–3.12 (4H, m), 4.02 (1H, t, J=7.5 Hz), 4.19–4.24 (3H, m), 7.15–7.21 (3H, m), 7.25–7.31 (9H, m)

TSIMS(M/Z): 528(M+H)$^+$

Example 48

5-Chloro-2-cyclohexyl-2,3-dihydro-6-[4-(3,3-diphenyl-1-propyl)piperazin-1-yl]-1H-isoindol-1-one In the same manner as in Example 47, the title compound was prepared from 6-[4-(t-butoxycarbonyl)piperazin-1-yl]-5-chloro-2-cyclohexyl-2,3-dihydro-1H-isoindol-1-one obtained in Example 45 and 3,3-diphenylpropyl bromide.

$^1$H-NMR(CDCl$_3$) δ: 1.18 (1H, m), 1.41–1.51 (4H, m), 1.70–1.75 (1H, m), 1.82–1.89 (4H, m), 2.27–2.39 (4H, m), 2.58–2.65 (4H, m), 3.07–3.13 (4H, m), 4.02 (1H, t, J=7.4 Hz), 4.05–4.26 (3H, m), 7.17–7.23 (2H, m), 7.25–7.36 (8H, m), 7.44 (1H, s), 7.52 (1H, s)

TSIMS(M/Z): 528(M+H)$^+$

Example 49

6-[4-t-butoxycarbonylpiperazin-1-yl]-2,3-dihydro-1H-isoindol-1-one

In the same manner as in step (b) or later steps of Example 1 and Example 30, the title compound was obtained using phthalimide.

$^1$H-NMR(CDCl$_3$) δ: 7.38–7.35 (2H, m), 7.17 (1H, dd, J=2.2, 8.6), 4.70 (1H, brs), 4.39 (2H, s), 3.59 (4H, t, J=4.8 Hz), 3.18 (4H, t, J=4.8 Hz), 1.77 (1H, s), 1.49 (9H, s)

ESIMS(m/z): 318(M+H)$^+$

Example 50

2,3-Dihydro-6-[4-(3,3-diphenyl-1-propyl)piperazin-1-yl]-1H-isoindol-1-one

In the same manner as in Example 47, the title compound was prepared from the compound obtained in Example 49.

$^1$H-NMR(CDCl$_3$) δ: 2.25–2.38 (4H, m), 2.56–2.60 (4H, m), 3.23–3.27 (4H, m), 4.02 (1H, t, J=7.1 Hz), 4.36 (2H, s), 6.56 (1H, brd), 7.14–7.56 (10H, m)

EIMS(m/z): 411(M$^+$)

Example 51

2-Benzyl-2,3-dihydro-6-[4-(t-butoxycarbonyl)-piperazin-1-yl]-1H-isoindol-1-one

Potassium carbonate (88 mg), sodium hydroxide (44 mg), tetrabutylaummonium hydrogen sulfate (11 mg), and benzyl bromide (81 mg) were added to a solution of the compound (100 mg), obtained in Example 49, in toluene (2 ml). The mixture was stirred at 80° C. overnight. The mixture was then cooled to room temperature. A saturated aqueous ammonium chloride solution (5 ml) was then added thereto, followed by separation with ethyl acetate and water. The ethyl acetate layer was washed with an aqueous sodium chloride solution, dried over magnesium sulfate, and then concentrated under the reduced pressure. The residue was purified by chromatography on silica gel (ethyl acetate:hexane=1:1) to give 111 mg of the title compound.

$^1$H-NMR(CDCl$_3$) δ: 7.40 (1H, d, J=2.2 Hz), 7.31 (1H, d, J=3.3), 7.11 (1H, dd, J=2.2, 3.3 Hz), 4.80 (2H, s), 4.21 (2H, s), 3.61 (4H, t, J=4.9), 3.19 (4H, t, J=4.9), 1.50 (9H, s)

TSIMS(m/z): 408(M+H)$^+$

Example 52

2-Benzyl-2,3-dihydro-6-[4-(3,3-diphenyl-1-propyl)-piperazin-1-yl]-1H-isoindol-1-one (a) Concentrated hydrochloric acid (0.5 ml) was added to a solution of the compound (90 mg), obtained in Example 51, in ethyl acetate (2 ml). The mixture was stirred at room temperature for 45 min. Ethyl acetate and purified water were then added thereto, followed by separation. The aqueous layer was concentrated under the reduced pressure to give 80 mg of 2-benzyl-2,3-dihydro-6-piperazine-1H-isoindol-1-one dihydrochloride.

$^1$H-NMR(D$_2$O) δ: 6.98–6.87 (3H, m), 4.24 (2H, s), 3.64 (2H, s), 3.32 (8H, brs)

(b) In the same manner as in step (f) of Example 1, the title compound was prepared from the compound obtained in step (a) just above and 3,3-diphenylpropyl bromide.

$^1$H-NMR(CDCl$_3$) δ: 7.45–7.08 (18H, m), 4.73 (2H, s), 4.17 (2H, s), 4.02 (1H, t, J=7.3 Hz), 3.26 (4H, t, J=5.0 Hz), 2.59 (4H, t, J=5.0 Hz), 2.32 (4H, m)

TSIMS(m/z): 502(M+H)$^+$

Example 53

2-(4-Bromo)benzyl-6-(4-t-butoxycarbonylpiperazin-1-yl)-2,3-dihydro-1H-isoindol-1-one The title compound was obtained in the same manner as in Example 51, except that 4-bromo benzyl bromide was used instead of benzyl bromide.

$^1$H-NMR(CDCl$_3$) δ: 7.35 (1H, d, J=2.5 Hz), 7.32 (1H, d, J=8.3 Hz), 7.11 (1H, dd, J=2.5, 8.3 Hz), 4.73 (2H, sHz), 4.17 (2H, s), 4.02 (1H, t, J=7.3 Hz), 3.58 (4H, t, J=5.0 Hz), 3.17 (4H, t, J=5.0 Hz), 2.32 (4H, m), 1.49 (9H, s)

TSIMS(m/z): 487(M+H)$^+$

Example 54

2-(4-Bromo)benzyl-2,3-dihydro-6-[4-(3,3-diphenyl-1-propyl)piperazin-1-yl]-1H-isoindol-1-one In the same manner as in Example 52, the title compound was prepared from the compound obtained in Example 53.

$^1$HNMR(CDCl$_3$) δ: 7.45–7.08 (17H, m), 4.73 (2H, s), 4.17 (2H, s) 4.02 (1H, t, J=7.3 Hz), 3.26 (4H, t, J=5.0 Hz), 2.59 (4H, t, J=5.0 Hz), 2.32 (4H, m)

TSIMS(m/z): 582(M+H)$^+$

Example 55

6-(4-t-Butoxycarbonylpiperazin-1-yl)-2-(4-chloro)-benzyl-2,3-dihydro-1H-isoindol-1-one In the same manner as in Example 51, the title compound was obtained from 4-chlorobenzyl chloride.

$^1$H-NMR(CDCl$_3$) δ: 7.35 (1H, d, J=2.5 Hz), 7.32 (1H, d, J=8.3 Hz), 7.11 (1H, dd, J=2.5, 8.3 Hz), 4.73 (2H, sHz), 4.17 (2H, s), 4.02 (1H, t, J=7.3 Hz), 3.58 (4H, t, J=5.0 Hz), 3.17 (4H, t, J=5.0 Hz), 2.32 (4H, m), 1.49 (9H, s)

TSIMS(m/z): 442(M+H)$^+$

Example 56

2-(4-Chloro)benzyl-2,3-dihydro-6-[4-(3,3-diphenyl-1-propyl)piperazin-1-yl]-1H-isoindol-1-one In the same manner as in Example 52, the title compound was prepared from the compound obtained in Example 55.

$^1$H-NMR(CDCl$_3$) δ: 7.45–7.08 (17H, m), 4.73 (2H, s), 4.17 (2H, s3, 4.02 (1H, t, J=7.3 Hz), 3.26 (4H, t, J=5.0 Hz), 2.59 (4H, t!, J=5.0 Hz), 2.32 (4H, m)

TSIMS(m/z): 537(M+H)$^+$

Example 57

6-(4-t-Butoxycarbonylpiperazin-1-yl)-2,3-dihydro-2-(4-methoxy)benzyl-1H-isoindol-1-one The title compound was obtained in the same manner as in Example 51, except that 4-methoxybenzyl chloride was used instead of benzyl bromide.

$^1$H-NMR(CDCl$_3$) δ: 7.32 (1H, d, J=2.4 Hz), 7.17 (2H, m), 7.02 (1H, dd, J=2.4, 8.3 Hz), 6.78 (2H, d, J=8.3 Hz), 4.66 (2H, s), 4.09 (2H, s), 3.72 (3H, s), 3.52 (4H, t, J=5.0 Hz), 3.11 (4H, t, J=5.0 Hz), 1.42 (9H, s)

ESIMS(m/z): 438(M+H)$^+$

Example 58

2,3-Dihydro-6-[4-(3,3-diphenyl-1-propyl)piperazin-1-yl]-2-(4-methoxy)benzyl-1H-isoindol-1-one In the same manner as in Example 52, the title compound was prepared from the compound obtained in Example 57.

$^1$H-NMR(CDCl$_3$) δ: 7.39 (1H,d, J=2.4Hz), 7.24–7.20 (13H, m), 7.60 (1H, dd, J=2.4, 8.3 Hz), 4.73 (2H, s), 4.13 (2H, s), 4.02 (1H, t, J=7.3 Hz), 3.79 (3H, s), 3.24 (4H, t, J=5.0 Hz), 2.57 (4H, t, J=5.0 Hz), 2.30 (4H, m)

TSIMS(m/z): 537(M+H)$^+$

Example 59

6-(4-t-Butoxycarbonylpiperazin-1-yl)-2-cyclopropyl-methyl-2,3-dihydro-1H-isoindol-1-one The title compound was obtained in the same manner as in Example 51, except that cyclopropylmethyl bromide was used instead of benzyl bromide.

$^1$H-NMR(CDCl$_3$) δ: 7.35 (1H, d, J=2.5 Hz), 7.32 (1H, d, J=8.3 Hz), 7.11 (1H, dd, J=2.5, 8.3 Hz), 4.27 (2H, s), 4.01 (1H, t, J=7.5 Hz), 3.58 (4H, t, J=4.8 Hz), 3.50 (2H, d, J=7.4 Hz), 3.17 (4H, t, J=4.8 Hz), 1.49 (9H, s), 1.25–1.11 (5H, m)

TSIMS(m/z): 372(M+H)$^+$

Example 60

2-Cyclopropylmethyl-2,3-dihydro-6-[4-(3,3-diphenyl-1-propyl)piperazin-1-yl]-1H-isoindol-1-one In the same manner as in Example 52, the title compound was prepared from the compound obtained in Example 59.

$^1$H-NMR(CDCl$_3$) δ: 7.33 (1H, d, J=2.2 Hz), 7.30–7.15 (11H, m), 7.69 (1H, dd, J=2.2, 8.3 Hz), 4.27 (2H, s), 4.01 (1H, t, J=7.5 Hz), 3.50 (2H, d, J=7.4 Hz), 3.24 (4H, t, J=5.0 Hz), 2.57 (4H, t, J=5.0 Hz), 2.32 (4H, m), 1.25–1.11 (5H, m)

TSIMS(m/z): 466(M+H)$^+$

Example 61

6-(4-t-Butoxycarbonylpiperazin-1-yl)-2-cyclohexyl-methyl-2,3-dihydro-1H-isoindol-1-one In the same manner as in Example 51, the title compound was obtained from cyclohexylmethyl bromide.

$^1$H-NMR(CDCl$_3$) δ: 7.35 (1H, d, J=2.5 Hz), 7.32 (1H, d, J=8.3 Hz), 7.11 (1H, dd, J=2.5, 8.3 Hz), 4.30 (2H, s), 3.58 (4H, t, J=5.0 Hz), 3.43 (2H, d, J=7.1 Hz), 3.17 (4H, t, J=5.0 Hz), 1.82–1.62 (4H, m), 1.48 (9H, s), 1.19 (11H, m)

TSIMS(m/z): 508(M+H)$^+$

Example 62

2-Cyclohexylmethyl-2,3-dihydro-6-[4-(3,3-diphenyl-1-propyl)piperazin-1-yl]-1H-isoindol-1-one In the same manner as in Example 52, the title compound was prepared from the compound obtained in Example 61.

$^1$H-NMR(CDCl$_3$) δ: 7.33 (1H, d, J=2.2 Hz), 7.30–7.15 (11H, m), 7.09 (1H, dd, J=2.2, 8.3 Hz), 4.27 (2H, s), 4.01

(1H, t, J=7.5 Hz), 3.42 (2H, d, J=7.4 Hz), 3.24 (4H, t, J=5.0 Hz), 2.57 (4H, t, J=5.0 Hz), 2.32 (4H, m), 1.25–1.02 (11H, m)

TSIMS(m/z): 508(M+H)$^+$

Example 63

6-[4-t-Butoxycarbonylpiperazin-1-yl]-2,3-dihydro-2-methyl-1H-isoindol-1-one

In the same manner as in Example 51, the title compound was obtained from methyl iodide.

$^1$H-NMR(CDCl$_3$) δ: 7.35 (1H, d, J=2.5 Hz), 7.32 (1H, d, J=8.3 Hz), 7.11 (1H, dd, J=2.5, 8.3 Hz), 3.60 (4H, t, J=5.0 Hz), 3.20 (4H, m), 1.49 (9H, s)

TSIMS(m/z): 332(M+H)$^+$

Example 64

2,3-Dihydro-6-[4-(3,3-diphenyl-1-propyl)piperazin-1-yl]-2-methyl-1H-isoindol-1-one In the same manner as in Example 52, the title compound was prepared from the compound obtained in Example 63.

$^1$H-NMR(CDCl$_3$) δ: 7.34–7.25 (10H, m), 7.14–7.20 (2H, m), 7.10 (1H, dd, J=2.3, 8.4 Hz), 4.20 (2H, s), 4.00 (1H, t, J=7.3 Hz), 3.25 (4H, t, J=4.7 Hz), 3.18 (3H, s), 2.57 (4H, t, J=4.7Hz), 2.32 (4H, brs), 1.70 (2H, brs)

TSIMS(m/z): 426(M+H)$^+$

Example 65

6-(4-t-Butoxycarbonylpiperazin-1-yl)-2,3-dihydro-2-(4-nitro-benzyl)-1H-isoindol-1-one In the same manner as in Example 51, the title compound was obtained from 4-nitro-benzyl bromide.

$^1$H-NMR(CDCl$_3$) δ: 7.44 (2H, td, J=6.5, 2.3 Hz), 7.39 (1H, d, J=2.3 Hz), 7.29 (1H, d, J=4.7 Hz), 7.16 (2H, d, J=8.4 Hz), 7.11 (1H, dd, J=8.4, 2.3 Hz), 4.74 (2H, s), 3.60 (4H, t, J=5.1 Hz), 3.19 (4H, t, J=5.1 Hz), 1.49 (9H, s)

ESIMS(m/z): 453(M+H)$^+$

Example 66

Ethyl[6-(4-t-Butoxycarbonylpiperazin-1-yl)-1-oxo-1,3-dihydro-isoindol-2-yl]acetate Dry THF (2 ml) was added in an argon atmosphere to the compound (100 mg) obtained in Example 49. The mixture was cooled to −78° C. A 1.0 M THF solution (347 μl) of bis(trimethylsilyl)amide sodium was slowly added thereto. The temperature of the mixture was raised to −50° C., and the mixture was stirred for 30 min. The reaction solution was cooled to −78° C. Ethyl bromoacetate (79 mg) was slowly added thereto. The temperature of the mixture was raised to room temperature, and the mixture was then stirred overnight. A saturated aqueous ammonium chloride solution (5 ml) was then added thereto, followed by separation with ethyl acetate and water. The ethyl acetate layer was washed with an aqueous sodium chloride solution, dried over ma sulfate, and then concentrated under the reduced pressure. The residue was purified by chromatography on silica gel (ethyl acetate:hexane=1:2) to give 119 mg of ethyl[6-(4-t-butoxycarbonylpiperazin-1-yl)-1-oxo-1,3-dihydro-isoindol-2-yl]acetate.

$^1$H-NMR(CDCl$_3$) δ: 7.35 (1H, d, J=2.5 Hz), 7.32 (1H, d, J=8.3 Hz), 7.11 (1H, dd, J=2.5, 8.3 Hz), 4.44 (2H, s), 4.38 (2H, s), 4.21 (2H, q, J=6.9 Hz), 3.58 (4H, t, J=5.0 Hz), 3.17 (4H, t, J=5.0 Hz), 1.49 (9H, s), 1.24 (3H, t, J=6.9 Hz)

TSIMS(m/z): 404(M+H)$^+$

Example 67

Ethyl{6-[4-(3,3-diphenyl-1-propyl)-piperazin-1-yl]-1-oxo-1,3-dihydro-isoindol-2-yl}acetate In the same manner as in Example 52, the title compound was prepared from the compound obtained in Example 66.

$^1$H-NMR(CDCl$_3$) δ: 7.35 (1H, d, J=2.5 Hz), 7.32 (1H, d, J=8.3 Hz), 7.29–7.16 (10H, m), 7.11 (1H, dd, J=2.5, 8.3 Hz), 4.44 (2H, s), 4.38 (2H, s), 4.21 (2H, q, J=6.9 Hz), 4.02 (1H, t, J=7.7 Hz), 3.25 (4H, t, J=4.8 Hz), 2.57 (4H, t, J=4.8 Hz), 2.i32 (4H, brs), 1.24 (3H, t, J=6.9 Hz)

TSIMS(m/z): 498(M+H)$^+$

Example 68

2-Cyclohexyl-7-[4-(3,3-diphenyl-1-propyl)-piperazin-1-yl]-3,4-dihydro-2H-isoquinolin-1-one (a) Cyclohexylamine (5.2 ml) was added to a solution of homophthalic acid (4.86 g) in toluene (100 ml). The mixture was heated under reflux at 110° C. for 6.5 hr. The precipitated crystals were collected by filtration. The filtrate was concentrated under the reduced pressure. The residue was purified by chromatography on silica gel (hexane:ethyl acetate=1:1) to give the title compound (110 mg). Separately, a portion (1.0 g) of the crystals collected by the filtration was stirred with heating at 160° C. for 4 hr. Water was added to the reaction product. The mixture was extracted with ethyl acetate. The extract was dried over anhydrous magnesium sulfate. The solvent was then removed by distillation. The residue was purified by chromatography on silica gel (hexane:ethyl acetate=1:1) to give N-cyclohexylhomophthalimide (424 mg).

$^1$H-NMR(CDCl$_3$) δ: 1.35 (2H, m), 1.68 (6H, m), 2.39 (2H, m), 4.00 (2H,, s), 4.79 (1H, m), 7.23 (1H, d, J=7.5), 7.42 (1H, t, J=7.5), 7.55 (1H, t, J=7.5), 8.11 (1H, d, J=7.5)

EIMS(m/z): 243(M$^+$)

(b) Sodium boron hydride (393 mg) was added to a solution of the compound (420 mg), obtained in step (a) just above, dissolved in a mixed solution (10 ml) of methylene chloride methanol=1:1 under cooling in an ice bath. The mixture was stirred at room temperature for 4 hr. The reaction solution was concentrated to dryness. Water was added to the residue. The mixture was extracted with methylene chloride, and then dried over anhydrous magnesium sulfate. The solvent was then removed by distillation. The residue was purified by chromatography on silica gel ( hexane:ethyl acetate=1:1) to obtain 2-cyclohexyl-3-hydroxy-3,4-dihydro-2H-isoquinolin-1-one (185 mg).

$^1$H-NMR(CDCl$_3$) δ: 1.50 (10H, m), 2.62 (1H, bs), 3.10 (2H, m), 4.56 (1H, m), 5.32 (1H, bs), 7.21 (1H, d, J=7.4), 7.35 (1H, t, J=7.6), 7.44 (1H, dt, J=1.5, 7.4), 8.05 (1H, d, J=1.5, 7.6)

FABMS(m/z): 246(M+H)$^+$ (c) The compound (22 mg) obtained in step (b) just above was stirred in a mixed solution of ethanol:concentrated hydrochloric acid=10:1 at room temperature for 30 min. Water was added to the reaction solution. The mixture was extracted with ethyl acetate, and then dried over anhydrous magnesium sulfate. The solvent was then removed by distillation. The residue was purified by chromatography on silica gel (hexane ethyl acetate=1:1) to give 2-cyclohexyl-2H-isoquinolin-1-one (18 mg).

H-NMR (CDCl$_3$) δ: 1.54 (10H, m), 5.01 (1H, m), 6.50 (1H, d, J=7.6), 7.17 (1H, d, J=7.6), 7.47 (2H, m), 7.62 (1H, dt, J=1.4, 8.0), 8.45 (1H, d, J=8.0)

TSIMS(m/z): 228(M+H)$^+$ (d) The compound (200 mg) obtained in step (c) just above was dissolved in a mixed solution (10.7 ml) of ethanol concentrated hydrochloric acid=15:1. 10% Pd—C (60 mg) was added to the solution, followed by hydrogenation for 3.5 hr. Pd—C was removed by filtration through Celite. The filtrate was concentrated under the reduced pressure. Water was then added the residue. The mixture was extracted with ethyl acetate. The organic layer was then dried over anhydrous magnesium sulfate. The solvent was then removed by distillation to give 2-cyclohexyl-3,4-dihydro-2H-isoquinolin-1-one (168 mg).

$^1$H-NMR(CDCl$_3$) δ: 1.44 (4H, m), 1.79 (6H, m), 2.90 (2H, t, J=6.6), 3.44 (2H, t, J=6.6), 4.65 (1H, m), 7.15 (1H, d, J=7.4), 7.31 (1H, t, J=7.4), 7.38 (1H, t, J=7.6), 8.08 (1H, d, J=7.6)

TSIMS(m/z): 230(M+H)$^+$ (e) In the same manner as in step (c) of Example 1, 2-cyclohexyl-7-nitro-3,4-dihydro-2H-isoquinolin-1-one (142 mg) was prepared from the compound (156 mg) obtained in step (d) just above.

H-NMR(CDCl$_3$) δ: 1.45 (4H, m), 1.79 (6H, m), 3.01 (2H, t, J=6.4), 3.51 (2H, t, J=6.4), 4.63 (1H, m), 7.35 (1H, d, J=8.2), 8.21 (1H, dd, J=2.4, 8.2), 8.87 (1H, d, J=2.4)

TSIMS(m/z): 275(M+H)$^+$ (f) In the same manner as in step (d) of Example 1, 7-amino-2-cyclohexyl-3,4-dihydro-2H-isoquinolin-1-one (117 mg) was prepared from the compound (142 mg) obtained in step (e) just above.

$^1$H-NMR(CDCl$_3$) δ: 1.42 (4H, m), 1.71 (6H, m), 2.78 (2H, t, J=6.5), 3.39 (2H, t, J=6.5), 3.73 (2H, bs), 4.64 (1H, m), 6.72 (1.H, dd, J=2.4, 7.9), 6.94 (1H, d, J=7.9), 7.40 (1H, d, J=;2.4)

TSIMS(m/z): 245(M+H)$^+$ (g) In the same manner as in step (e) of Example 1, 2-cyclohexyl-7-(piperazin-1-yl)-3,4-dihydro-2H-isoquinolin-1-one (310 mg) was prepared from the compound (440 mg) obtained in step (f) just above.

$^1$H-NMR(CDCl$_3$) δ: 1.26 (4H, m), 1.73 (6H, m), 2.83 (2H, t, J=6.4), 3.09 (4H, t, J=2.2), 3.21 (4H, t, J=2.2), 3.42 (2H, t, J=6.4), 4.66 (1H, m), 6.98 (1H, dd, J=2.4, 8.4), 7.07 (1H, d, J=!8.4), 7.65 (1H, d, J=2.4)

TSIMS(m/z): 314(M+H)$^+$ (h) In the same manner as in step (f) of Example 1, the title compound (12 mg) was prepared from the compound (24 mg) obtained in step (g) just above and 3,3-diphenylpropyl bromide.

$^1$H-NMR(CDCl$_3$) δ: 1.45 (10H, m), 2.33 (bs, 4H), 2.57 (4H, t, J=4.6), 2.82 (2H, t, J=6.5), 3.23 (4H, t, J=4.6), 3.42 (2H, t, J=6.5), 4.02 (1H, t, J=7.0), 4.67 (1H, m), 6.98 (1H, dd, J=2.6, 8.3), 7.05 (1H, d, J=8.3), 7.22 (10H, m), 7.65 (1H, d, J=2.6)

TSIMS(m/z): 508(M+H)$^+$

Example 69

2-Cyclohexyl-7-(4-t-butoxycarbonyl-piperazin-1-yl)-3,4-dihydro-2H-isoquinolin-1-one Di-t-butyl dicarbonate (176 mg) and triethylamine (0.12 ml) were added to a solution of the compound (125 mg), obtained in step (g) of Example 68, in tetrahydrofuran (10 ml). The mixture was stirred at room temperature for one hr. Water was added to the reaction solution. The mixture was extracted with ethyl acetate The organic layer was then dried over anhydrous magnesium sulfate. The solvent was then removed by distillation. The residue was purified by chromatography on silica gel (hexane:ethyl acetate=9:1) to give the title compound (157 mg).

$^1$H-NMR(CDCl$_3$) δ: 1.43 (4H, m), 1.49 (9H, s), 1.73 (6H, m), 2.83 (2H, t, J=6.5), 3.15 (4H, t, J=5.2), 3.42 (2H, t, J=6.5), 3.58 (4H, t, J=5.2), 4.65 (1H, m), 6.98 (1H, dd, J=2.5, 8.2), 7.07 (1H, d, J=8.2), 7.65 (1H, d, J=2.5)

TSIMS(m/z): 414(M+H)$^+$

Example 70

2-Cyclohexyl-7-(4-t-butoxycarbonyl-piperazin-1-yl)-2H-isoquinolin-1-one

10% Pd—C(150 mg) was added to a solution of the compound (146 mg), obtained in Example 69, in ethanol (5 ml). The mixture was heated at 75° C. for 4 hr. The Pd—C was removed by filtration through Celite. The filtrate was then concentrated under the reduced pressure to give the title compound (122 mg).

$^1$H-NMR(CDCl$_3$) δ: 1.27 (4H, m), 1.49 (9H, s), 1.92 (6H, m), 3.25 (4H, t, J=5.1), 3.61 (4H, t, J=5.1), 5.00 (1H, m), 6.46 (1H, d, J=7.5), 7.03 (1H, d, J=7.5), 7.31 (1H, dd, J=2.7, 8.7), 7.42 (1H, d, J=8.7), 7.85 (1H, d, J=2.7)

TSIMS(m/z): 412(M+H)$^+$

Example 71

2-Cyclohexyl-7-[4-(3,3-diphenyl-1-propyl)-piperazin-1-yl]-2H-isoquinolin-1-one

Trifluoroacetic acid (1 ml) was added under cooling in an ice bath to the compound (10 mg) obtained in Example 70. The mixture was stirred for 2 hr. A saturated aqueous sodium hydrogencarbonate solution was then added to the reaction solution. The mixture was extracted with ethyl acetate. The organic layer was dried over anhydrous magnesium sulfate. The solvent was then removed by distillation. N,N-dimethylformamide (2 ml) was added to the residue to prepare a solution. Potassium carbonate (lO mg) and 3,3-diphenylpropyl bromide (4 mg) were then added to the solution. The mixture was stirred at room temperature overnight. Water was added to the reaction solution. The mixture was then extracted with ethyl acetate. The organic layer was dried over anhydrous magnesium sulfate. The solvent was then removed by distillation. The residue was purified by preparative TLC (hexane:ethyl acetate=1:1) to give the title compound (10 mg).

$^1$H-NMR(CDCl$_3$) δ: 1.91 (10H, m), 2.34 (4H, m), 2.60 (4H, t, J=5.0), 3.32 (4H, t, J=5.0), 4.02 (1H, t, J=7.0), 5.00 (1H, m), 6.46 (1H, d, J=7.4), 7.02 (1H, d, J=7.4), 7.27 (1H, m), 7.41 (1H, d, J=8.9), 7.84 (1H, d, J=2.2)

TSIMS(m/z): 506(M+H)$^+$

Example 72

2-Benzyl-7-(4-t-butoxycarbonyl-piperazin-1-yl)-3,4-dihydro 2H-isoquinolin-1-one

In the same manner as in Example 66, the title compound (80 mg) was obtained from 7-(4-t-butoxycarbonyl-piperazin-1-yl)-3,4-dihydro-1H-isoquinolin-1-one (100 mg), synthesized according to the method described in J. Med. Chem., 39,4583 (1996), and benzyl bromide (0.053 ml).

¹H-NMR(CDCl₃) δ: 1.49 (9H, s), 2.86 (2H, t, J=6.7), 3.18 (4H, t, J=5.0), 3.47 (2H, t, J=6.7), 3.59 (4H, t, J=5.0), 4.80 (1H, s), 7.01 (1H, dd, J=2.2, 8.3), 7.08 (1H, d, J=8.3), 7.32 (5H, m), 7.72 (1H, d, J=2.2)

ESIMS(m/z): 422(M+H)⁺

Example 73

2-Benzyl-7-[4-(3,3-diphenyl-1-propyl)-piperazin-1-yl]-3,4 dihydro-2H-isoquinolin-1-one The title compound (43 mg) was obtained in the same manner as in Example 71, except that the compound (60 mg) obtained in Example 72 was used as the starting compound and hydrochloric acid was used instead of trifluoroacetic acid.

¹H-NMR(CDCl₃) δ: 2.32 (4H, m), 2.57 (4H, t, J=4.9), 2.84 (2H, t, J=6.5), 3.24 (4H, t, J=4.9), 3.45 (2H, t, J=6.5), 4.10 (1H, t, J=7.1), 6.99 (1H, dd, J=2.5, 8.5), 7.05 (1H, d, J=8.5), 7.30 (14H, m), 7.71 (1H, d, J=2.5)

TSIMS(m/z): 516(M+H)⁺

Example 74

2-Methyl-7-(4-t-butoxycarbonyl-piperazin-1-yl)-3,4-dihydro-2H-isoquinolin-1-one

The title compound was obtained in the same manner as in Example 66, except that methyl iodide was used instead of ethyl bromoacetate.

¹H-NMR(CDCl₃) δ: 1.47 (9H, s), 2.90 (2H, t, J=6.6), 3.13 (m, 7H), 3.54 (6H, m), 6.96 (1H, dd, J=1.2, 8.3), 7.07 (1H, d, J=8.3), 7.64 (1H, d, J=1.2)

TSIMS(m/z): 346(M+H)⁺

Example 75

7-[4-(3,3-Diphenyl-1-propyl)-piperazin-1-yl]-3,4-dihydro2-methyl-2H-isoquinolin-1-one In the same manner as in Example 71, the title compound was obtained from the compound obtained in Example 74.

¹H-NMR(CDCl₃) δ: 2.44 (4H, m), 2.93 (2H, t, J=6.5), 3.16 (7H, m), 3.54 (4H, m), 4.06 (1H, m), 4.11 (2H, t, J=6.5), 6.99 (1H, dd, J=2.6, 8.2), 7.09 (1H, d, J=8.2), 7.26 (10H, m), 7.65 (17, d, J=2.6)

FABMS(m/z): 440(M+H)⁺

Example 76

2-Cyclohexylmethyl-7-(4-t-butoxycarbonyl-piperazin-1-yl)-3,4dihydro-2H-isoquinolin-1-one The title compound was obtained in the same manner as in Example 66, except that cyclohexylmethyl bromide was used instead of ethyl bromoacetate.

¹H-NMR(CDCl₃) δ: 1.23 (5H, m), 1.48 (9H, s), 1.72 (6H, m), 2.89 (2H, t, J=6.5), 3.15 (4H, t, J=5.0), 3.40 (2H, d, J=7.1), 3.52 (2H, t, J=6.5), 3.57 (4H, t, J=5.0), 6.99 (1H, dd, J=2.7, 8.2), 7.08 (1H, d, J=8.2), 7.65 (1H, d, J=2.7)

TSIMS(m/z): 428(M+H)⁺

Example 77

2-Cyclohexylmethyl-7-[4-(3,3-diphenyl-1-propyl)-piperazin-1-yl]-3,4-dihydro-2H-isoquinolin-1-one In the same manner as in Example 71, the title compound was obtained from the compound obtained in Example 76.

¹H-NMR(CDCl₃) δ: 1.72 (5H, m), 2.34 (4H, m), 2.58 (4H, t, J=4.4), 2.89 (2H, t, J=6.6), 3.22 (4H, t, J=4.4), 3.40 (2H, d, J=6.9), 3.51 (2H, t, J=6.6), 4.00 (1H, t, J=7.0), 6.97 (1H, dd, J=2.5, 8.3), 7.06 (1H, d, J=8.3), 7.20 (10H, m), 7.63 (1H, d, J=2.5)

TSIMS(m/z): 522(M+H)⁺

Example 78

2-Cyclopropylmethyl-7-(4-t-butoxycarbonyl-piperazin-1-yl)-3,4-dihydro-2H-isoquinolin-1-one The title compound was obtained in the same manner as in Example 66, except that cyclopropylmethyl bromide was used instead of ethyl bromoacetate.

¹H-NMR(CDCl₃) δ: 0.31 (2H, m), 0.53 (2H, m), 1.04 (1H, m), 1.47 (9H, s), 2.92 (2H, t, J=6.5), 3.15 (4H, t, J=5.1), 3.47 (2H, d, J=6.5), 3.57 (4H, t, J=5.1), 3.62 (2H, t, J=6.5), 6.99 (1H, dd, J=2.7, 8.2), 7.09 (1H, d, J=8.2), 7.65 (1H, d, J=2.7)

TSIMS(m/z): 386(M+H)⁺

Example 79

2-Cyclopropylmethyl-7-[4-(3,3-diphenyl-1-propyl)-piperazin-1-yl]-3,4-dihydro-2H-isoquinolin-1-one In the same manner as in Example 71, the title compound was prepared from the compound obtained in Example 78.

¹H-NMR(CDCl₃) δ: 0.30 (2H, m), 0.52 (2H, m), 1.04 (1H, m), 2.30 (4H, m), 2.57 (4H, t, J=4.9), 2.91 (2H, t, J=6.6), 3.23 (4H, t, J=4.9), 3.47 (2H, d, J=6.9), 3.62 (2H, t, J=6.6), 4.01 (1H:, t, J=7.1), 6.98 (1H, dd, J=2.6, 8.3), 7.07 (1H, d, J=8.3), 7.20 (10H, m), 7.65 (1H, d, J=2.6)

TSIMS(m/z): 480(M+H)⁺

Example 80

2-(4-Chlorobenzyl)-7-(4-t-butoxycarbonyl-piperazin-1-yl)-3,4-dihydro-2H-isoquinolin-1-one The title compound was obtained in the same manner as in Example 66, except that 4-chlorobenzyl chloride was used instead of ethyl bromoacetate.

¹H-NMR(CDCl₃) δ: 1.49 (9H, s), 2.86 (2H, t, J=6.6), 3.17 (4H, t, J=5.0), 3.45 (2H, t, J=6.6), 3.58 (4H, t, J=5.0), 4.74 (2H, s), 7.00 (1H, dd, J=2.6, 8.3), 7.08 (1H, d, J=8.3), 7.28 (4H, m), 7.69 (1H, d, J=2.6)

TSIMS(m/z): 456(M+H)⁺

Example 81

2-(4-Chlorobenzyl)-7-[4-(3,3-diphenyl-1-propyl)-piperazin-1-yl]-3,4-dihydro-2H-isoquinolin-1-one In the same manner as in Example 71, the title compound was prepared from the compound obtained in Example 80.

¹H-NMR(CDCl₃) δ: 2.33 (4H, m), 2.58 (4H, t, J=4.8), 2.85 (2H, t, J=6.6), 3.25 (4H, t, J=4.8), 3.45 (2H, t, J=6.6), 4.03 (11H, t, J=7.1), 4.75 (2H, s), 7.00 (1H, dd, J=2.5, 8.3), 7.06 (1H, d, J=8.3), 7.30 (14H, m), 7.70 (1H, d, J=2.5)

TSIMS(m/z): 550(M+H)⁺

Example 82

7-[4-(3,3-Diphenyl-1-propyl)-piperazin-1-yl]-3,4-dihydro-2H-isoquinolin-1-one

In the same manner as in step (f) of Example 1, the title compound was obtained from 7-(piperazin-1-yl)-3,4-dihydro-2H-isoquinolin-1-one, synthesized according to the method described in J. Med. Chem., 39, 4583 (1996), and 3,3-diphenylpropyl bromide.

¹H-NMR(CDCl₃) δ: 2.32 (4H, m), 2.57 (4H, t, J=5.0), 2.91 (2H, t, J=6.4), 3.24 (4H, t, J=5.0), 3.53 (2H, dt, J=2.9, 6.4), 4.02 (1H, t, J=7.0), 5.96 (1H, bs), 7.02 (1H, dd, J=2.7, 8.4), 7.11 (1H, d, J=8.4), 7.61 (1H, d, J=2.7)

FABMS(m/z): 426(M+H)⁺

Example 83

2-(2-Chlorobenzyl)-7-[4-(3,3-diphenyl-1-propyl)-piperazin-1-yl]-3,4-dihydro-2H-isoquinolin-i-one In the same manner as in Example 66, the title compound was prepared from the compound obtained in Example 82 and 2-chlorobenzyl chloride.

¹H-NMR(CDCl₃) δ: 2.35 (4H, m), 2.60 (4H, t, J=4.8), 2.90 (2H, t, J=6.6), 3.26 (4H, t, J=4.8), 3.53 (2H, t, J=6.6), 4.02 (1H, t, J=7.1), 4.92 (2H, S), 7.01 (1H, dd, J=2.5, 8.3), 7.08 (1H, d, J=8.3), 7.26 (14H, m), 7.70 (1H, d, J=2.5)

TSIMS(m/z): 550(M+H)⁺

Example 84

2-(3-Chlorobenzyl)-7-[4-(3,3-diphenyl-1-propyl)-piperazin-1-yl]-3,4-dihydro-2H-isoquinolin-1-one In the same manner as in Example 66, the title compound was prepared from the compound obtained in Example 82 and 3-chlorobenzyl chloride.

¹H-NMR(CDCl₃) δ: 2.34 (4H, m), 2.59 (4H, t, J=4.6), 2.87 (2H, t, J=6.0), 3.25 (4H, t, J=4.6), 3.47 (2H, t, J=6.0), 4.02 (1H, t, J=7.2), 4.76 (2H, s), 7.00 (1H, dd, J=2.6, 8.3), 7.08 (1H, d, J=8.3), 7.28 (14H, m), 7.71 (1H, d, J=2.6)

TSIMS(m/z): 550(M+H)⁺

Example 85

2,3-Dihydro-3,3-dimethyl-6-[4-(3,3-diphenyl-1-propyl)piperazin-1-yl]-1H-isoindol-1-one 2,3-Dihydro-3,3-dimethyl-1H-isoindol-1-one was synthesized according to the method described in Angew. chem. Int. Ed. Engl., 7, 373 (1968). In the same manner as in step (e) and later steps of Example 68, the title compound was obtained from this compound.

¹H-NMR(CDCl₃) δ: 1.51 (6H, s), 2.25–2.38 (4H, m), 2.58 (4H, m), 3.25 (4H, m), 4.01 (1H, t, J=7.5), 6.15 (1H, s), 7.10–7.39 (13H)

EIMS(m/z): 411 (M)+

Example 86

3-Cyclohexyl-3,4-dihydro-6-[4-(3,3-diphenyl-1-propyl)piperazin-1-yl]-2H-1,3-benzoxazin-4-one (a) Thionyl chloride (20 ml) was added to 5-nitrosalicylic acid (5 g). The mixture was heated under reflux for 2 hr. Thionyl chloride was removed by distillation under the reduced pressure. Toluene was added to the residue, and the mixture was concentrated. This procedure was repeated twice. The residue was dissolved in methylene chloride (40 ml). Cyclohexylamine (9.4 ml) was added under ice cooling to the solution. The mixture was stirred at room temperature overnight. The reaction solution was diluted with ethyl acetate. The diluted solution was washed with water, dilute hydrochloric acid, and water in that order, and then dried over magnesium sulfate. The solvent was then removed by distillation under the reduced pressure to give 6.9 g of N-cyclohexyl-5-nitrosalicylamide.

¹H-NMR(CDCl₃) δ: 1.19–1.50 (5H, m), 1.71 (1H, m), 1.83 (2H, m), 2.06 (2H, m), 3.99 (1H, m), 6.39 (1H, brd, J=6.1), 7.06 (1H, d, J=9.2), 8.27 (1H, dd, J=2.5, 9.2), 8.38 (1H, d, J≦2.5), 13.52 (1H, br.s)

TSIMS(m/z): 263(M−H)⁻

(b) Formic acid (5 ml) and 37% formaldehyde (5 ml) were added to the compound (1 g) obtained in step (a) just above. The mixture was heated under reflux for 5 hr. The reaction solution was cooled. About 20 ml of water was added thereto. The precipitated crystals were collected by filtration, and then dried to give 981 mg of 3-cyclohexyl-3,4-dihydro-6-nitro-2H-benzoxazin-4-one.

¹H-NMR(CDCl₃) δ: 1.15 (1H, m), 1.35–1.52 (4H1, m), 1.73 (1H, brd), 1.87 (4H, brd), 4.48 (1H, m), 5.26 (2H, s), 7.09 (1H, d, J=9.0), 8.31 (1H, dd, J=2.7, 9.0), 8.87 (1H, d, J=2.7)

TSIMS(m/z): 276(M)+

(c) In the same manner as in step (f) and later steps of Example 68, the title compound was obtained from the compound obtained in step (b) just above.

¹H-NMR(CDCl₃) δ: 1.14 (1H, m), 1.34–1.49 (4H, m), 1.70 (1H, brd), 1.83 (4H, brd), 2.22–2.37 (4H, m), 2.57 (4H, m), 3.15 (4H, m), 4.01 (1H, t, J=7.3), 4.46 (1H, m), 5.09 (2H, s), 6.86 (1H, d, J=8.8), 7.04 (1H, dd, J=2.9, 8.8), 7.15–7.30 (10H), 7.47 (1H, d, J=2.9)

TSIMS(m/z): 510(M+H)⁺

Example 87

3Cyclohexyl-3,4-dihydro-6-[4-(3,3-diphenyl-1-propyl)piperazin-1-yl]-2H-1,3-benzothiazin-4-one (a) Isobutyl chloroformate (1.43 ml) was added under ice cooling to a solution of 2-chloro-5-nitrobenzoic acid (2.01 g) and triethylamine (1.53 ml) in methylene chloride (40 ml). The mixture was stirred under ice cooling for 45 min. Thereafter, cyclohexylamine (1.25 ml) was added thereto. The reaction solution was stirred at room temperature for 1.5 hr. The precipitated crystals were dissolved in chloroform. The organic layer was washed with water, dilute hydrochloric acid, and water in that order, dried over magnesium sulfate, and then concentrated under the reduced pressure. Ethyl ether was added to the residue. The precipitated crystals were collected by filtration, and then dried to give 2.63 g of N-cyclohexyl-2-chloro-5-nitrobenzamide.

¹H-NMR(CDCl₃) δ: 1.18–1.81 (8H), 2.07 (2H, m), 4.03 (1H, m), 5.99 (1H, br.s), 7.58 (1H, d, J=8.7), 8.20 (1H, dd, J=2.7, 8.7), 8.47 (1H, d, J=2.7)

(b) A solution of potassium hydrosulfide obtained by passing hydrogen sulfide into an aqueous solution (10 ml) of potassium hydroxide (1.68 g) was added to an ethanol solution (20 ml) of the compound (850 mg) synthesized in step (a) just above. The mixture was stirred at 90° C. for 2 hr. Argon gas was bubbled into the mixture. The solvent was then removed by distillation. Water was added to the residue. The mixture was acidified by the addition of 5 N hydrochloric acid. The precipitated crystals were collected by filtration. Formic acid (6 ml) and 37% formaldehyde (6 ml) were added to the crystals, followed by heating under ref lux for 3 hr. The reaction solution was cooled. Water was added thereto, and the resultant precipitate was collected by filtration. The precipitate collected by filtration was separated with chloroform and water. The insolubles were removed by filtration. The chloroform layer was concentrated. The residue was subjected to column chromatography on silica gel. In this case, elution was carried out using chloroform. Thus, 195 mg of 3-cyclohexyl-3,4-dihydro-6-nitro-2H-benzothiazin-4-one was obtained.

¹H-NMR(CDCl₃) δ: 1.15 (1H, m), 1.39–1.51 (4H, m), 1.73 (1H, br.d), 1.82–1.92 (4H, m), 4.58 (2H, s), 4.61 (1H, m), 7.44 (1H, d, J=8.5), 8.18 (1H, dd, J=2.4, 8.5), 8.97 (1H, d, J=2.4)

TSIMS(m/z): 292(M)⁻

(c) In the same manner as in step (f) and later steps of Example 68, the title compound was obtained from the compound obtained in step (b) just above.

¹H-NMR(CDCl₃) δ: 1.13 (1H, m), 1.37–1.51 (4H, m), 1.70 (1H, br.d), 1.81–1.89 (4H, m), 2.24–2.37 (4H, m), 2.55 (4H), 3.21 (4H), 4.01 (1H, t, J=7.1), 4.45 (2H, s), 4.61 (1H, m), 6.93 (1H, dd, J=2.8, 8.7), 7.13 (1H, d, J=8.7), 7.15–7.31 (10H), 7.66 (1H, d, J=2.8)

TSIMS(m/z): 526(M+H)

Example 88

2-Cyclohexyl-6-[4-(2-diphenylaminoethyl)piperazin-1-yl]-2,3-dihydro-1H-isoindol-1-one (a) In the same manner as described in Heterocycles, Vol. 19, No.1, 75–82 (1982), (2, 2-diethoxyethyl)-diphenylamine was obtained from diphenylamine and bromoacetaldehyde diethyl acetal.

$^1$H-NMR(CDCl$_3$) δ: 1.18 (6H, t, J=12.7 Hz), 3.50 (2H, q, J=12.7 Hz), 3.65 (2H, q, J=12.7 Hz), 3.88 (2H, d, J=5.3 Hz), 4.70 (1H, t, J=5.3 Hz), 6.93 (2H, t, J=7.3 Hz), 7.08 (4H, m), 7.24 (4H, m)

TSIMS(m/z): 286(M+H)$^+$ (b) The compound (700 mg) obtained in step (a) just above was stirred at room temperature overnight in a solvent (40 ml) of acetone:water=7:1 in the presence of Amberlyst 15 (50 mg). The reaction solution was filtered through a filter paper. The filtrate was subjected to distillation under the reduced pressure, and purification was then carried out by column chromatography on silica gel (eluent hexane:ethyl acetate=10:1) to give N,N-diphenylaminoacetaldehyde (250 mg).

$^1$H-NMR(CDCl$_3$) δ: 4.36 (2H, d, J=2.5 Hz), 6.92 (5H, m), 7.25 (5H, m), 9.78 (1H, t, J=2.5 Hz)

TSIMS(m/z): 212(M+H)$^+$ (c) In the same manner as in Example 38, the title compound (50 mg) was obtained from the compound (50 mg) obtained in step (b) just above and the compound (70 mg) obtained in step (e) of Example 1.

$^1$H-NMR(CDCl$_3$) δ: 1.39–1.84 (10H, m), 2.65 (4H, t, J=5.0 Hz), 2.72 (2H, t, J=7.5 Hz), 3.23 (4H, t, J=5.0 Hz), 3.91 (2H, t, J=7.5 Hz), 4.22 (1H, br), 4.25 (2H, s), 6.94 (2H, dt, J=0.9, 7.5 Hz), 7.02 (4H, dd, J=0.7, 7.8 Hz), 7.08 (1H, dd, J=2.5, 8.3 Hz), 7.28 (4H, dt, J=0.7, 7.8 Hz), 7.31 (1H, s), 7.35 (1H, d, J=2.4 Hz)

TSIMS(m/z): 495(M+H)$^+$

Example 89

4-(2-Cyclohexyl-1-oxo-2,3-dihydro-1H-isoindol-6-yl)piperazine-1-carboxylic acid benzhydrylamide (a) Benzhydrylamine (1.83 g) was dissolved in dichloromethane (3.0 ml). Carbonyldiimidazole (1.78 g) was added to the solution. The mixture was stirred at room temperature overnight. Water and dichloromethane were added thereto. The mixture was stirred, and then extracted with dichloromethane. The organic layer was dried over anhydrous magnesium sulfate. The solvent was then removed by distillation to give imidazole-1-carboxylic acid benzhydrylamide.

$^1$H-NMR(CDCl$_3$) δ: 6.29 (1H, d, J=7.7 Hz), 6.92 (1H, bs), 7.34 (12H, m), 7.96 (1H, bs)

TSIMS(M/Z): 278(M+H)$^+$ (b) The compound (138 mg) obtained in step (a) just above was dissolved in toluene (5 ml). The compound (149 mg) obtained in Example 1e and triethylamine (8.3 ml) were added to the solution. The mixture was stirred at room temperature for 1.5 hr. The reaction solution was extracted with ethyl acetate. The extract was dried over anhydrous magnesium sulfate. The solvent was then removed by distillation. The residue was developed in preparative TLC (chloroform:methanol=9:1) to give the title compound (127 mg).

$^1$H-NMR(CDCl$_3$) δ: 1.62 (10H, m), 3.24 (4H, m), 3.60 (4H, m), 4.28 (3H, bs), 5.06 (1H, d, J=7.1 Hz), 6.17 (1H, d, J=7.1 Hz), 7.10 (1H, dd, J=2.5, 8.2 Hz), 7.30 (12H, m)

TSIMS(M/Z): 509(M+H)$^+$

Example 90

2-Benzyl-7-[4-(4,4-diphenyl-1-butyl)piperazin-1-yl]-3,4-dihydro-2H-isoquinolin-1-one The compound (121 mg) obtained in Example 72 was dissolved in ethyl acetate (3.0 ml) and concentrated hydrochloric acid (0.7 ml) The solution was stirred at room temperature for 2 hr. The reaction solution was neutralized with a saturated aqueous sodium hydrogencarbonate solution, and then extracted with ethyl acetate. The organic layer was dried over anhydrous magnesium sulfate. The solvent was then removed by distillation. In the same manner as in Example 38, the title compound (48 mg) was obtained from the residue and 4,4-diphenylbutylaldehyde.

$^1$H-NMR(CDCl$_3$) δ: 1.54 (2H, m), 2.12 (2H, m), 2.45 (2H, t, J=7.5 Hz), 2.57 (4H, m), 2.84 (2H, t, J=6.6 Hz), 3.24 (4H, m), 3.45 (2H, t, J=6.6 Hz), 3.94 (1H, t, J=7.8 Hzm), 4.81 (2H, s), 7.00 (1H, dd, J=2.6, 8.3 Hz), 7.06 (1H, d, J=8.3 Hz), 7.28 (10H, m), 7.73 (1H, d, J=2.6 Hz)

TSIMS(M/Z): 530(M+H)$^+$

Example 91

7-[4-(Benzhydryloxycarbonyl)piperazin-1-yl]-2-benzyl-3,4-dihydro-2H-isoquinolin-1-one The compound (100 mg) obtained in Example 72 was dissolved in ethyl, acetate (2.5 ml) and concentrated hydrochloric acid (0.5 ml). The solution was stirred at room temperature for 2 hr. The reaction solution was neutralized with a saturated aqueous sodium hydrogencarbonate solution, and then extracted with ethyl acetate. The organic layer was dried over anhydrous magnesium sulfate. The solvent was then removed by distillation. In the same manner as in Example 28, the title compound (104 mg) was obtained from the residue and benzhydryloxycarbonyl azide.

$^1$H-NMR(CDCl$_3$) δ: 2.86 (2H, t, J=6.6 Hz), 3.18 (4H, m), 3.47 (2H, t, J=6.6 Hz), 3.76 (4H, m), 4.80 (2H, s), 6.85 (1H, s), 7.00 (1H, dd, J=2.6, 8.3 Hz), 7.08 (1H, d, J=8.3 Hz), 7.35 (15H, m), 7.73 (1H, d, J=2.6 Hz)

TSIMS(M/Z): 532(M+H)$^+$

Example 92

2Benzyl-7-[4-(4-chlorobenzyl)piperazin-1-yl]-3,4-dihydro-2H-isoquinolin-1-one (a) 7-Piperazin-1-yl-3,4-dihydro-2H-isoquinolin-1-one (100 mg) synthesized according to the method described in J. Med. Chem., 39, 4583 (1996) was dissolved in N,N-dimethylformamide (5 ml). Potassium carbonate (71 mg) and 4-chloro benzyl bromide (106 mg) were added to the solution. The mixture was stirred at room temperature for 2 hr. Water was added to the reaction solution. The mixture was then extracted with ethyl acetate. The organic layer was dried over anhydrous magnesium sulfate. The solvent was then removed by distillation under the reduced pressure. The residue was purified by column chromatography on silica gel (chloroform:methanol=9:1) to give 7-[4-(4-chlorobenzyl)piperazin-1-yl]-3,4-dihydro-2H-isoquinolin-1-one (75 mg).

$^1$H-NMR(CDCl$_3$) δ: 2.59 (4H, m), 2.90 (2H, t, J=5.4 Hz), 3.23 (4H, m), 3.52 (4H, m), 6.40 (1H, bs), 7.00 (1H, dd,

J=2.6, 8.3 Hz), 7.10 (1H, d, J=8.3 Hz), 7.29 (4H, m), 7.62 (1H, d, J=2.6 Hz)

FABMS(M/Z): 356(M+H)$^+$

In the same manner as in Example 51, the title compound (45 mg) was obtained from the compound (70 mg) obtained in step (a) just above and benzyl bromide (32 mg).

$^1$H-NMR(CDCl$_3$) δ: 2.60 (4H, m), 2.85 (2H, t, J=6.6 Hz), 3.25 (4H, m), 3.46 (2H, t, J=6.6 Hz), 3.53 (2H, s), 4.79 (2H, s), 6.99 (1H, dd, J=2.5, 8.3 Hz), 7.06 (1H, d, J=8.3 Hz), 7.30 (9H, m), 7.72 (1H, d, J=2.5 Hz)

ESIMS(M/Z): 446(M+H)$^+$

Example 93

2Cyclopropyl-6-[4-(4,4-diphenyl-1-butyl)piperazin-1-yl]-2,3-dihydro-1H-isoindol-1-one In the same manner as in Example 38, the title compound (21 mg) was prepared from 2-cyclopropyl-(6-piperazin-1-yl)-2,3-dihydro-1H-isoindol-1-one (66 mg) obtained in the course of the synthesis of the compound of Example 25 and 4,4-diphenylbutylaldehyde (45 mg).

$^1$H-NMR(CDCl$_3$) δ: 0.81–0.94 (4H, m), 1.46–1.56 (2H, m), 2.09 (2H, dt, J=7.7, 8.0 Hz), 2.40–2.50 (2H, m), 2.55 (4H, m), 2.91–2.97 (1H, m), 3.22 (4H, m), 3.91 (1H, t, J=8.0 Hz), 4.22 (2H, s), 7.09 (1H, dd, J=2.4, 8.3 Hz), 7.14–7.20 (2H, m), 7.23–7.31 (10H, m)

TSIMS(m/z): 466(M+H)$^+$

Example 94

2-Cyclopentyl-6-[4-( 3,3-diphenyl-1-propyl)-piperazin- 1-yl]-2,3-dihydro-1H-isoindol-1-one In the same manner as in Example 51, the title compound (44 mg) was prepared from the compound (50 mg) obtained in Example 50 and cyclopentyl bromide (27 mg).

$^1$H-NMR(CDCl$_3$) δ: 1.56 (m, 8H), 2.33 (4H, m), 2.48 (4H, t, J=4.6 Hz), 3.16 (4H, t, J=4.6 Hz), 3.94 (1H, t, J=7.6 Hz), 4.20 (2H, s), 4.67 (1H, m), 7.02–7.08 (12H, m), 7.26 (1H, d, J=2.5 Hz)

TSIMS(m/z): 480(M+H)$^+$

Example 95

2-Cycloheptyl-6-[4-(3,3-diphenyl-1-propyl)-piperazin-1-yl]-2,3-dihydro-1H-isoindol-1-one In the same manner as in Example 51, the title compound (12 mg) was prepared from the compound (50 mg) obtained in Example 50 and cycloheptyl bromide (32 mg).

$^1$H-NMR(CDCl$_3$) δ: 1.56 (12H, m), 2.33 (4H, m), 2.48 (4H, t, J=4.6 Hz), 3.16 (4H, t, J=4.6 Hz), 3.94 (1H, t, J=7.6 Hz), 4.20 (2H, s), 4.67 (1H, m), 7.02–7.08 (12H, m), 7.26 (1H, d, J=2.5 Hz)

TSIMS(m/z): 508(M+H)$^+$

Example 96

6!-[4-(3,3-Diphenyl-1-propyl)piperazin-1-yl]-2-isopropyl-2,3-dihydro-1H-isoindol-1-one In the same manner as in Example 51, the title compound (32 mg) was prepared from the compound (50 mg) obtained in Example 50 and 2-bromopropane (148 mg).

$^1$H-NMR(CDCl$_3$) δ: 1.27 (6H, d, J=6.8 Hz), 2.33 (4H, m), 2.48 (4H, t, J=4.6 Hz), 3.16 (4H, t, J=4.6 Hz), 3.94 (1H, t, J=7.6 Hz), 4.25 (2H, s), 4.66 (1H, qq, J=6.8, 6.8 Hz), 7.02–7.08 (12H, m), 7.26 (1H, d, J=2.5 Hz)

TSIMS(m/z): 454(M+H)$^+$

Example 97

2-Allyl-6-[4-(3,3-diphenyl-1-propyl)piperazin-1-yl]-2,3-dihydro-1H-isoindol-1-one In the same manner as in Example 51, the title compound (51 mg) was prepared from the compound (50 mg) obtained in Example 50 and allyl bromide (22 mg).

$^1$H-NMR(CDCl$_3$) δ: 2.21 (4H, m), 2.51 (4H, t, J=4.6 Hz), 3.18 (4H, t, J=4.6 Hz), 3.94 (1H, t, J=7.6 Hz), 4.13 (2H, d, J=6.1 Hz), 4.16 (2H, s), 5.10 (1H, S), 5.13 (1H, dd, J=1.3, 6.1 Hz), 5.76 (1H, m)

TSIMS(m/z): 452(M+H)$^+$

Example 98

2-Cinnamyl-[4-(3,3-diphenyl-1-propyl)piperazin-1-yl]-2,3-dihydro-1H-isoindol-1-one In the same manner as in Example 51, the title compound (28 mg) was prepared from the compound (50 mg) obtained in Example 50 and cinnamyl bromide (36 mg).

$^1$H-NMR(CDCl$_3$) δ: 2.21 (4H, m), 2.51 (4H, t, J=4.6 Hz), 3.18 (4H, t, J=4.6 Hz), 3.39 (1H, d, J=1.3 Hz), 3.94 (1H, t, J=7.6 Hz), 4.13 (1H, dd, J=1.3, 6.3Hz), 4.22 (2H, s), 4.29 (2H, d, J=6.3 Hz), 6.13 (1H, m), 6.48 (1H, d, J=15.8 Hz), 7.00–7.34 (16H, m)

TSIMS(m/z): 528(M+H)$^+$

Example 99

6-[4-(3,3-Diphenyl-1-propyl)piperazin-1-yl]-2-(3-methoxybenzyl)-2,3-dihydro-1H-isoindol-1-one In the same manner as in Example 51, the title compound (35 mg) was prepared from the compound (50 mg) obtained in Example 50 and 3-methoxybenzyl chloride (17 mg).

$^1$H-NMR(CDCl$_3$) δ: 2.33 (4H, m), 2.48 (4H, t, J=4.6 Hz), 3.16 (4H; t, J=4.6 Hz), 3.77 (3H, s), 4.02 (1H, t, J=7.6 Hz), 4.18 (2H, s), 4.76 (2H, s), 7.02–7.08 (16H, m), 7.38 (1H, d, J=2.5 Hz)

TSIMS(m/z): 532(M+H)$^+$

Example 100

6-[4-(3,3-Diphenyl-1-propyl)piperazin-1-yl]-2-(3-methylbenzyl)-2,3-dihydro-1H-isoindol-1-one In the same manner as in Example 51, the title compound (48 mg) was prepared from the compound (50 mg) obtained in Example 50 and α-bromo-m-xylene (17 mg).

$^1$H-NMR(CDCl$_3$) δ: 2.33 (7H, m), 2.48 (4H, t, J=4.6 Hz), 3.16 (4H, t, J=4.6 Hz), 3.94 (1H, t, J=7.6 Hz), 4.16 (2H, s), 4.70 (2H, s), 7.00–7.08 (16H, m), 7.26 (1H, d, J=2.5 Hz)

TSIMS(m/z): 516(M+H)$^+$

Example 101

6-[4-(3,3-Diphenyl-1-propyl)piperazin-1-yl]-2-(3trifluoromethylbenzyl)-2,3-dihydro-1H-isoindol-1-one In the same manner as in Example 51, the title compound (52 mg) was prepared from the compound (50 mg) obtained in Example 50 and 3-trifluoromethylbenzyl chloride (35 mg).

¹H-NMR(CDCl₃) δ: 2.33 (4H, m), 2.48 (4H, t, J=4.6 Hz), 3.16 (4H, t, J=4.6 Hz), 3.94 (1H, t, J=7.6 Hz), 4.17 (2H, s), 4.82 (2H, s), 7.00–7.08 (16H, m), 7.26 (1H, d, J=2.5 Hz)

TSIMS(m/z): 570(M+H)⁺

Example 102

6-[4-(3,3-Diphenyl-1-propyl)piperazin-1-yl]-2-(3-nitrobenzyl)-2,3-dihydro-1H-isoindol-1-one In the same manner as in Example 51, the title compound (38 mg) was prepared from the compound (50 mg) obtained in Example 50 and 3-nitro benzyl bromide (39 mg).

¹H-NMR(CDCl₃) δ: 2.33 (4H, m), 2.48 (4H, t, J=4.6 Hz), 3.16 (4H, t, J=4.6 Hz), 3.94 (1H, t, J=7.6 Hz), 4.22 (2H, s), 4.87 (2H, s), 6.98–7.08 (14H, m), 7.26 (1H, d, J=2.5 Hz), 8.12 (2H, d, J=6.9 Hz)

TSIMS(m/z): 547(M+H)⁺

Example 103

6-[4-(3,3-Diphenyl-1-propyl)piperazin-1-yl]-2-(thiazol-4-yl)methyl-2,3-dihydro-1H-isoindol-1-one In the same manner as in Example 51, the title compound (40 mg) was prepared from the compound (50 mg) obtained in Example 50 and 5-thiazolemethyl chloride (24 mg).

¹H-NMR(CDCl₃) δ: 2.23 (4H, m), 2.48 (4H, t, J=4.6 Hz), 3.16 (4H, t, J=4.6 Hz), 3.94 (1H, t, J=7.6), 4.32 (2H, s), 4.87 (2H, s), 7.02 (1H, dd, J=8.3, 2.4 Hz), 7.08–7.23 (11H, m), 7.26 (1H, d, J=2.4 Hz), 8.67–8.71 (2H, m)

TSIMS(m/z): 509(M+H)⁺

Example 104

2-Benzyl-3,3-dimethyl-6-[4-(3,3-diphenyl-1-propyl)-piperazin-1-yl]-2,3-dihydro-1H-isoindol-1-one The title compound (144 mg) was prepared from the compound (150 mg) obtained in Example 85 and benzyl bromide.

¹H-NMR(CDCl₃) δ: 1.32 (6H, s), 2.29–2.35 (4H, m), 2.58, (4H, br.t), 3.26 (4H, br.t), 4.02 (1H, t, J=7.4 Hz), 4.73 (2H, s), 7.10–7.38, 15H)

TSIMS(M/Z): 530(M+H)⁺

Example 105

3,3-Dimethyl-6-[4-(3,3-diphenyl-1-propyl)piperazin-1-yl]-2-(2-methylbenzyl)-2,3-dihydro-1H-isoindol-1-one The title compound (154 mg) was prepared from the compound (150 mg) obtained in Example 85 and 2-methyl benzyl bromide.

¹H-NMR(CDCl₃) δ: 1.30 (6H, s), 2.29–2.36 (4H, m), 2.39 (3H, s), 2.58 (4H, br.t), 3.26 (4H, br.t), 4.02 (1H, t, J=7.2 Hz), 4.74 (2H, s), 7.10–7.38 (14H)

TSIMS(M/Z): 544(M+H)⁺

Example 106

3,3-Dimethyl-6-[4-(3,3-diphenyl-1-propyl)piperazin-1-yl]-2-(1-phenylethyl)-2,3-dihydro-1H-isoindol-1-one The title compound (48 mg) was prepared from the compound (150 mg) obtained in Example 85 and 1-phenylethyl bromide.

¹H-NMR(CDCl₃) δ: 1.41 (3H, s), 1.48 (3H, s), 1.94, (3H, d, J=7.3 Hz), 2.30–2.34 (4H, m), 2.57 (4H, br.t), 3.23 (4H, br.t), 4.01 (1H, t, J=7.3 Hz), 4.74 (1H, q, J=7.3 Hz), 7.08–7.52 (15H)

TSIMS(M/z): 544(M+H)⁺

Example 107

2-Cyclobutyl-7-[4-(3,3-diphenyl-1-propyl)piperazin-1-yl]-3,4,dihydro-2H-isoquinolin-1-one In the same manner as in Example 51, the title compound (21 mg) was prepared from the compound (100 mg) obtained in Example 82 and cyclobutyl bromide (47 mg).

¹H-NMR(CDCl₃) δ: 1.70 (6H, m), 2.32 (4H, bs), 2.57 (4H, m), 2.89 (2H, t, J=5.6 Hz), 3.22 (4H, m), 3.52 (2H, t, J=5.6 Hz), 4.02 (1H, m), 5.20 (1H, m), 6.98 (1H, dd, J=3.0, 8.3 Hz), 7.06 (1H, d, J=8.3 Hz), 7.27 (10H, m), 7.63 (1H, d, J=3.0 Hz)

TSIMS(M/Z): 480(M+H)⁺

Example 108

2-Cyclopentyl-7-[4-(3,3-diphenyl-1-propyl)-piperazin-1-yl]-3,4-dihydro-2H-isoquinolin-1-one In the same manner as in Example 51, the title compound (71 mg) was prepared from the compound (100 mg) obtained in Example 82 and cyclopentyl bromide (52 mg).

¹H-NMR(CDCl₃) δ: 1.73 (8H, m), 2.32 (4H, bs), 2.57 (4H, m), 2.84 (2H, t, J=6.4 Hz), 3.23 (4H, m), 3.40 (2H, t, J=6.4 Hz), 4.02 (1H, t, J=7.0 Hz), 5.20 (1H, m), 6.97 (1H, dd, J=2.6, 8.3 Hz), 7.05 (1H, d, J=8.3 Hz), 7.27 (10H, m), 7.65 (1H, d, J=2.6 Hz)

TSIMS(M/Z): 494(M+H)⁺

Example 109

2-Cycloheptyl-7-[4-(3,3-diphenyl-1-propyl)-piperazin-1-yl]-3,4-dihydro-2H-isoquinolin-1-one In the same manner as in Example 51, the title compound (26 mg) was prepared from the compound (50 mg) obtained in Example 82 and cycloheptyl bromide (30 mg).

¹H-NMR(CDCl₃) δ: 1.67 (12H, m), 2.32 (4H, bs), 2.57 (4H, m), 2.82 (2H, t, J=6.5 Hz), 3.22 (4H, m), 3.43 (2H, t, J=6.5 Hz), 4.01 (1H, t, J=7.2 Hz), 4.78 (1H, m), 6.96 (1H, dd, J=2.5, 8.3 Hz), 7.05 (1H, d, J=8.3 Hz), 7.22 (10H, m), 7.64 (1H, d, J=2.5 Hz)

TSIMS(M/Z): 522(M+H)⁺

Example 110

2-Allyl-7-[4-(3,3-diphenyl-1-propyl)piperazin-1-yl]-3,4-dihydro-2H-isoquinolin-1-one In the same manner as in Example 51, the title compound (12 mg) was prepared from the compound (50 mg) obtained in Example 82 and allyl bromide (21 mg).

¹H-NMR(CDCl₃) δ: 2.30 (4H, bs), 2.57 (4H, m), 2.89 (2H, t, J=6.6 Hz), 3.23 (4H, m), 3.49 (2H, t, J=6.6 Hz), 4.01 (1H, t, J=7.2 Hz), 4.20 (2H, d, J=6.0 Hz), 5.23 (2H, m), 5.55 (1H, m), 6.99 (1H, dd, J=2.6, 8.5 Hz), 7.06 (1H, d, J=8.5 Hz), 7.24 (10H, m), 7.65 (1H, d, J=2.6 Hz)

TSIMS(M/Z): 466(M+H)⁺

Example 111

2-Cinnamyl-7-[4-(3,3-diphenyl-1-propyl)piperazin-1-yl]-3,4-dihydro-2H-isoquinolin-1-one In the same manner as in Example 66, the title compound (27 mg) was prepared from the compound (50 mg) obtained in Example 82 and cinnamyl bromide (22 mg).

¹H-NMR(CDCl₃) δ: 2.33 (4H, m), 2.90 (2H, t, J=6.6 Hz), 3.23 (4H, m), 3.54 (2H, t, J=6.6 Hz), 4.02 (2H, t, J=7.3 Hz), 4.36 (2H, d, J=6.4 Hz), 6.25 (1H, dt, J=6.4, 15.0 Hz), 6.58 (1H, d, J=15.0 Hz), 7.00 (1H, dd, J=2.3, 8.2 Hz), 7.07 (1H, d, J=8.2 Hz), 7.27 (15H, m), 7.68 (1H, d, J=2,3 Hz)

TSIMS(M/Z): 542(M+H)⁺

Example 112

7-[4-(3,3-Diphenyl-1-propyl)piperazin-1-yl]-2-(3-phenyl-1-propyl)-3,4-dihydro-2H-isoquinolin-1-one In the same manner as in Example 51, the title compound (11 mg) was prepared from the compound (30 mg) obtained in Example 82 and 3-phenyl-propyl bromide (21 mg).

¹H-NMR(CDCl₃) δ: 1.95 (2H, tt, J=6.6, 7.9 Hz), 2.30 (4H, m), 2.57 (4H, t, J=4.8 Hz), 2.85 (2H, t, J=7.9 Hz), 2.88 (2H, t, J=6. 6 Hz), 3.23 (4H, t, J=4.8 Hz), 3.48 (2H, t, J=6.6 Hz), 3.61 (2H, t, J=6.6 Hz), 4.01 (1H, t, J=7.1 Hz), 6.96 (1H, dd, J=2.8, 8.3 Hz), 7.04 (1H, d, J=8.3 Hz), 7.17 (6H, m), 7.27 (10H, m), 7.64 (1H, d, J=7.5 Hz)

TSIMS(m/z): 544(M+H)⁺

Example 113

7-[4-(3,3-Diphenyl-1-propyl)piperazin-1-yl]-2-phenetyl-3,4-dihydro-2H-isoquinolin-1-one In the same manner as in Example 51, the title compound (76 mg) was prepared from the compound (30 mg) obtained in Example 82 and 2-bromoethylbenzene (39 mg).

¹H-NMR(CDCl₃) δ: 2.30 (4H, m), 2.57 (4H, t, J=4.8 Hz), 2.75 (2H, t, J=6.5 Hz), 2.88 (2H, t, J=6.6 Hz), 3.23 (4H, t, J=4.8 Hz), 3.34 (2H, t, J=6.5 Hz), 3.48 (2H, t, J=6.6 Hz), 4.01 (1H, t, J=7.1 Hz), 6.96 (1H, dd, J=2.8, 8.3 Hz), 7.04 (1H, d, J=8.3 Hz), 7.17 (6H, m), 7.27 (10H, m), 7.64 (1H, d, J=7.5 Hz)

FABMS(m/z): 530(M+H)⁺

Example 114

2-(3,3-Diphenyl-1-propyl)-7-[4-(3,3-diphenyl-1-propyl)piperazin-1-yl]-3,4-dihydro-2H-isoquinolin-1-one In the same manner as in Example 51, the title compound (35 mg) was prepared from the compound (30 mg) obtained in Example 82 and 3,3-diphenyl-1-propyl bromide (29 mg).

1H-NMR(CDCl₃) δ: 2.28–2.42 (6H, m), 2.57 (4H, t, J=4.8 Hz), 2.88 (2H, t, J=7.8 Hz), 3.23 (4H, t, J=4.8 Hz), 3.42 (2H, t, J=6.4 Hz), 3.49 (2H, t, J=7.8 Hz), 4.00 (2H, t, J=7.5 Hz), 6.95 (1H, dd, J=2.8, 8.3 Hz), 7.00 (1H, d, J=8.3 Hz), 7.17 (5H, m), 7.27 (12H, m), 7.63 (1H, d, J=7.5 Hz)

TSIMS(m/z): 620(M+H)⁺

Example 115

7-[4-(3,3-Diphenyl-1-propyl)piperazin-1-yl]-2-(2-methylbenzyl)-3,4-dihydro-2H-isoquinolin-1-one In the same manner as in Example 66, the title compound (48 mg) was prepared from the compound (50 mg) obtained in Example 82 and 2-methyl benzyl bromide (26 mg).

¹H-NMR(CDCl₃) δ: 2.33 (3H, s), 2.35 (4H, m), 2.59 (4H, m), 2.83 (2H, t, J=6.4 Hz), 3.27 (4H, m), 3.40 (2H, t, J=6.4 Hz), 3.42 (1H, t, J=7.1 Hz), 4.81 (2H, s), 7.00 (1H, dd, J=2.5, 8.5 Hz), 7.06 (1H, d, J=8.5 Hz), 7.24 (14H, m), 7.71 (1H, d, J=2.5 Hz)

TSIMS(M/Z): 530(M+H)⁺

Example 116

7-[4-(3,3-Diphenyl-1-propyl)piperazin-1-yl]-2-(3-methylbenzyl)-3,4-dihydro-2H-isoquinolin-1-one In the same manner as in Example 66, the title compound (25 mg) was prepared from the compound (50 mg) obtained in Example 82 and 3-methyl benzyl bromide (26 mg).

¹H-NMR(CDCl₃) δ: 2.33 (7H, bs), 2.60 (4H, m), 2.84 (2H, t, J=6.7 Hz), 3.26 (4H, m), 3.45 (2H, t, J=6.7 Hz), 4.02 (1H, t, J=7.3 Hz), 4.76 (2H, s), 7.00 (1H, dd, J=2.8, 8.5 Hz), 7.05 (1H, d, J=8.5 Hz), 7.21 (14H, m), 7.71 (1H, d, J=2.8 Hz)

TSIMS(M/Z): 530(M+H)⁺

Example 117

7-[4-(3,3-Diphenyl-1-propyl)piperazin-1-yl]-2-(4-methylbenzyl)-3,4-dihydro-2H-isoquinolin-1-one In the same manner as in Example 66, the title compound (24 mg) was prepared from the compound (50 mg) obtained in Example 82 and 4-methyl benzyl bromide (26 mg).

¹H-NMR(CDCl₃) δ: 2.34 (7H, bs), 2.60 (4H, m), 2.83 (2H, t, J=6.5 Hz), 3.25 (4H, m), 3.44 (2H, t, J=6.5 Hz), 4.02 (1H, t, J=7.70 Hz), 4.74 (2H, s), 6.98 (1H, dd, J=2.8, 8.3 Hz), 7.04 (1H, d, J=8.3 Hz), 7.22 (14H, m), 7.71 (1H, d, J=2.8 Hz)

TSIMS(M/Z): 530(M+H)⁺

Example 118

2-(3,4-Dimethylbenzyl)-7-[4-(3,3-diphenyl-1-propyl)piperazin-1-yl]-3,4-dihydro-2H-isoquinolin-1-one In the same manner as in Example 51, the title compound (30 mg) was prepared from the compound (50 mg) obtained in Example 82 and 3,4-dimethylbenzyl chloride (20 mg).

¹H-NMR(CDCl₃) δ: 2.24 (6H, s), 2.34 (4H, bs), 2.58 (4H, m), 2.83 (2H, m), 3.25 (4H, m), 3.44 (2H, m), 4.01 (1H, m), 4.72 (2H, s), 7.17 (15H, m), 7.71 (1H, d, J=2.5 Hz)

TSIMS(M/Z): 544(M+H)⁺

Example 119

2-(2,5-Dimethylbenzyl)-7-[4-(3,3-diphenyl-1-propyl)piperazin-1-yl]-3,4-dihydro-2H-isoquinolin-1-one In the same manner as in Example 51, the title compound (28 mg) was prepared from the compound (52 mg) obtained in Example 82 and 2,5-dimethylbenzyl chloride (28 mg).

¹H-NMR(CDCl₃) δ: 2.28 (3H, s), 2.29 (3H, s), 2.30 (4H, m), 2.57 (4H, t, J=4.8 Hz), 2.88 (2H, t, J=6.6 Hz), 3.23 (4H, t, J=4.8 Hz), 3.48 (2H, t, J=6.6 Hz), 4.01 (1H, t, J=7.1 Hz), 4.84 (2H, s), 6.96 (1H, dd, J=2.8, 8.3 Hz), 7.04 (1H, d, J=8.3 Hz), 7.17 (3H, m), 7.27 (11H, m)

TSIMS(m/z): 544(M+H)⁺

Example 120

7-[4-(3,3-Diphenyl-1-propyl)piperazin-1-yl]-2-(2,4,6-trimethylbenzyl)-3,4-dihydro-2H-isoquinolin-1-one In the same manner as in Example 51, the title compound (22 mg) was prepared from the compound (52 mg) obtained in Example 82 and 2,4,6-trimethylbenzyl chloride (31 mg).

¹H-NMR(CDCl₃) δ: 2.28 (3H, s), 2.29 (3H, s), 2.30 (7H, m), 2.57 (4H, t, J=4.8 Hz), 2.88 (2H, t, J=6.6 Hz), 3.23 (4H, t, J=4.8 Hz), 3.48 (2H, t, J=6.6 Hz), 4.01 (1H, t, J=7.1 Hz), 4.85 (2H, s), 6.96 (1H, dd, J=2.8, 8.3 Hz), 7.04 (1H, d, J=8.3 Hz), 7.17 (3H, m), 7.27 (10H, m)

TSIMS(m/z): 558(M+H)⁺

Example 121

7-[4-(3,3-Diphenyl-1-propyl)piperazin-1-yl]-2-(1-phenylethyl)-3,4-dihydro-2H-isoquinolin-1-one In the same manner as in Example 51, the title compound (29 mg) was prepared from the compound (50 mg) obtained in Example 82 and 1-phenylethyl bromide (27 mg).

¹-NMR(CDCl₃) δ: 1.59 (3H, d, J=7.1 Hz), 2.34 (4H, bs), 2.59 (4H, m), 2.73 (2H, t, J=6.9 Hz), 3.08 (1H, m), 3.25 (4H, m), 3.35 (1H, m), 4.02 (1H, t, J=7.0 Hz), 6.25 (1H, q, J=7.1 Hz), 6.98 (1H, dd, J=2.4, 8.4 Hz), 7.03 (1H, d, J=8.4 Hz), 7.31 (15H, m), 7.72 (1H, d, J=2.4 Hz)

TSIMS(M/Z): 530(M+H)⁺

Example 122

7-[4-(3,3-Diphenyl-1-propyl)piperazin-1-yl]-2-(4-trifluoromethylbenzyl)-3,4-dihydro-2H-isoquinolin-1-one In the same manner as in Example 51, the title compound (44 mg) was prepared from the compound (50 mg) obtained in Example 82 and 4 trifluoromethylbenzyl chloride (35 mg).

¹H-NMR(CDCl₃) δ: 2.33 (4H, bs), 2.58 (4H, m), 2.88 (2H, t, J=6.6 Hz), 3.25 (4H, m), 3.47 (2H, t, J=6.6 Hz), 4.02 (1H, t, J=7.2 Hz), 4.83 (2H, s), 7.00 (1H, dd, J=2.5, 8.5 Hz), 7.07 (1H, d, J=8.5 Hz), 7.28 (10H, m), 7.45 (2H, d, J=8.0 Hz), 7.59 (2H, d, J=8.0 Hz), 7.70 (1H, d, J=2.5 Hz)

TSIMS(M/Z): 584(M+H)⁺

Example 123

7-[4-(3,3-Diphenyl-1-propyl)piperazin-1-yl]-2-(3-trifluoromethylbenzyl)-3,4-dihydro-2H-isoquinolin-1-one In the same manner as in Example 51, the title compound (41 mg) was prepared from the compound (50 mg) obtained in Example 82 and 3-trifluoromethylbenzyl chloride (35 mg).

¹H-NMR(CDCl₃) δ: 2.34 (4H, bs), 2.59 (4H, m), 2.88 (2H, t, J=6.6 Hz), 3.26 (4H, m), 3.48 (2H, t, J=6.6 Hz), 4.04 (1H, t, J=7.2 Hz), 4.85 (2H, s), 7.01 (1H, dd, J=2.5, 8.5 Hz), 7.08 (1H, d, J=8.5 Hz), 7.37 (14H, m), 7.72 (1H, d, J=2.5 Hz)

TSIMS(M/Z): 584(M+H)⁺

Example 124

7-[4-(3,3-Diphenyl-1-propyl)piperazin-1-yl]-2-(3-fluorobenzyl)-3,4-dihydro-2H-isoquinolin-1-one In the same manner as in Example 51, the title compound (11 mg) was prepared from the compound (50 mg) obtained in Example 82 and 3-fluoro benzyl bromide (24 mg).

¹H-NMR(CDCl₃) δ: 2.29–2.33 (4H, m), 2.58 (4H, t, J=5.0 Hz), 2.87 (2H, t, J=6.6 Hz), 3.24 (4H, t, J=5.0 Hz), 3.46 (2H, t, J=6.6 Hz), 4.02 (1H, t, J=7.4 Hz), 4.77 (2H, s), 6.94–7.11 (6H, m), 7.15–7.20 (2H, m), 7.25–7.31 (8H, m), 7.69 (1H, d, J=2.5 Hz)

TSIMS(M/Z): 534(M+H)⁺

Example 125

2-(3-Bromobenzyl)-7-[4-(3,3-diphenyl-1-propyl)-piperazin-1-yl]-3,4-dihydro-2H-isoquinolin-1-one In the same manner as in Example 51, the title compound (38 mg) was prepared from the compound (50 mg) obtained in Example 82 and 3-bromo benzyl bromide (32 mg).

¹H-NMR(CDCl₃) δ: 2.30–2.33 (4H, m), 2.57 (4H, t, J=4.6 Hz), 2.86 (2H, t, J=6.7 Hz), 3.24 (4H, t, J=4.6 Hz), 3.46 (2H, t, J=6.7 Hz), 4.02 (1H, t, J=7.5 Hz), 4.75 (2H, s), 6.99 (1H, dd, J=2.7, 8.4 Hz), 7.05 (1H, d, J=8.4 Hz), 7.16–7.21 (4H, m), 7.26–7.33 (8H, m), 7.40 (1H, d, J=7.8 Hz), 7.47 (1H, s), 7.69 (1H, d, J=2.4 Hz)

TSIMS(M/Z): 596(M+H)⁺

Example 126

2-(3,4-Dichlorobenzyl)-7-[4-(3,3-diphenyl-1-propyl)piperazin-1-yl]-3,4-dihydro-2H-isoquinolin-1-one In the same manner as in Example 51, the title compound (44 mg) was prepared from the compound (50 mg) obtained in Example 82 and 3,4-dichlorobenzyl chloride (26 mg).

¹H-NMR(CDCl₃) δ: 2.33 (4H, bs), 2.57 (4H, m), 2.89 (2H, m), 3.25 (4H, m), 3.44 (2H, m), 4.02 (1H, t, J=7.0 Hz), 4.73 (2H, s), 7.03 (1H, dd, J=2.5, 8.5 Hz), 7.07 (1H, d, J=8.5 Hz), 7.27 (13H, m), 7.69 (1H, d, J=2.5 Hz)

TSIMS(M/Z): 586(M+H)⁺

Example 127

2-(2,4-Diochlorobenzyl)-7-[4-(3,3-diphenyl-1-propyl)piperazin-1-yl]-3,4-dihydro-2H-isoquinolin-1-one In the same manner as in Example 51, the title compound (38 mg) was prepared from the compound (50 mg) obtained in Example 82 and 2, 4-dichlorobenzyl chloride (26 mg).

¹H-NMR(CDCl₃) δ: 2.33 (4H, bs), 2.57 (4H, m), 2.91 (2H, m), 3.24 (4H, m), 3.52 (2H, m), 4.02 (1H, t, J=6.9 Hz), 4.86 (2H, s), 7.05 (1H, dd, J=2.5, 8.5 Hz), 7.07 (1H, d, J=8.3 Hz), 7.24 (13H, m), 7.68 (1H, d, J=2.5 Hz)

TSIMS(M/Z): 586(M+H)⁺

Example 128

Methyl 4-{7-[4-(3,3-diphenyl-1-propyl)piperazin-1-yl]-1-oxo-3,4-dihydro-2H-isoquinolin-2-ylmethyl}-benzoate In the same manner as in Example 51, the title compound (80 mg) was prepared from the compound (100 mg) obtained in Example 82 and methyl 4-(bromomethyl) benzoate (109 mg).

¹H-NMR(CDCl₃) δ: 1.25 (3H, s), 2.30 (4H, m), 2.57 (4H, t, J=4.8 Hz), 2.88 (2H, t, J=6.6 Hz), 3.23 (4H, t, J=4.8 Hz), 3.48 (2H, t, J=6.6 Hz), 4.01 (1H, t, J=7.1 Hz), 6.96 (1H, dd, J=2.8, 8.3 Hz), 7.04 (1H, d, J=8.3 Hz), 7.17 (3H, m), 7.27 (12H, m)

TSIMS(m/z): 574(M+H)⁺

Example 129

7-[4-(3,3-Diphenyl-1-propyl)piperazin-1-yl]-2-(3-methoxybenzyl)-3,4-dihydro-2H-isoquinolin-1-one In the same manner as in Example 51, the title compound (35 mg) was prepared from the compound (50 mg) obtained in Example 82 and 3-methoxybenzyl chloride (28 mg).

¹H-NMR(CDCl₃) δ: 2.34 (4H, bs), 2.59 (4H, m), 2.85 (2H, t, J=6.7 Hz), 3.25 (4H, m), 3.46 (2H, t, J=6.7 Hz), 3.79 (3H, s), 4.02 (1H, t, J=6.9 Hz), 4.77 (2H, s), 6.87 (4H, m), 6.99 (1H, dd, J=2.5, 8.4 Hz), 7.06 (1H, d, J=8.4 Hz), 7.27 (10H, m), 7.70 (1H, d, J=2.5 Hz)

TSIMS(M/Z): 546(M+H)⁺

Example 130

2-(3,5-Dimethoxybenzyl)-7-[4-(3,3-diphenyl-1-propyl)piperazin-1-yl]-3,4-dihydro-2H-isoquinolin-1-one In the same manner as in Example 51, the title compound (40 mg) was prepared from the compound (50 mg) obtained in Example 82 and 3,5-dimethoxybenzyl chloride (34 mg).

¹H-NMR(CDCl₃) δ: 2.33 (4H, bs), 2.58 (4H, m), 2.85 (2H, t, J=6.4 Hz), 3.25 (4H, m), 3.46 (2H, t, J=6.4 Hz), 3.77 (6H, s), 4.03 (1H, t, J=7.1 Hz), 4.72 (2H, s), 6.37 (1H, d, J=2.2 Hz), 6.48 (2H, d, J=2.2 Hz), 6.99 (1H, dd, J=2.4, 8.5 Hz), 7.05 (1H, d, J=8.5 Hz), 7.27 (10H, m), 7.70 (1H, d, J=2.4 Hz)

FABMS(M/Z): 576(M+H)⁺

Example 131

7-[4-(3,3-Diphenyl-1-propyl)piperazin-1-yl]-2-(3-hydroxybenzyl)-3,4-dihydro-2H-isoquinolin-1-one The compound (44 mg) obtained in Example 127 was dissolved in dichloromethane (5 ml). The solution was cooled to 0° C. A 1.0 M dichloromethane solution (0.24 ml) of boron tribromide was then added to the solution. The mixture was stirred at room temperature for 2 hr. A saturated aqueous sodium hydrogencarbonate solution was added to the reaction solution. The mixture was then extracted with dichloromethane. The organic layer was dried over anhydrous magnesium sulfate. The solvent was then removed by distillation. The residue was developed in preparative TLC (chloroform:methanol=9:1) to give the title compound (24 mg).

¹H-NMR(CDCl₃) δ: 2.31 (4H, bs), 2.53 (4H, m), 2.67 (2H, t, J=6.6 Hz), 3.15 (4H, m), 3.38 (2H, t, J=6.6 Hz), 4.00 (1H, t, J=7.1 Hz), 4.71 (2H, s), 6.85 (4H, m), 7.22 (12H, m), 7.63 (1H, bs)

TSIMS(M/Z): 532(M+H)⁺

Example 132

2-(3,5-Dihydroxybenzyl)-7-[4-(3,3-diphenyl-1-propyl)piperazin-1-yl]-3,4-dihydro-2H-isoquinolin-1-one In the same manner as in Example 131, the title compound (28 mg) was prepared from the compound (60 mg) obtained in Example 130 and a 1.0 M aqueous dichloromethane solution (0.6 ml) of boron tribromide.

¹H-NMR(DMSO-d₆) δ: 2.22 (4H, bs), 2.82 (2H, t, J=6.4 Hz), 3.11 (4H, bs), 3.39 (2H, t, J=6.4 Hz), 3.41 (1H, bs), 4.51 (2H, s), 6.07 (1H, s), 6.14 (2H, s), 7.25 (13H, m)

TSIMS(M/Z): 548(M+H)⁺

Example 133

2+(2-Hydroxy-2-phenylethyl)-7-[4-(3,3-diphenyl-1-propyl)piperazin-1-yl]-3,4-dihydro-2H-isoquinolin-1-one In the same manner as in Example 51, the title compound (17 mg) was prepared from the compound (45 mg) obtained in Example 50 and styrene oxide.

¹H-NMR(CDCl₃) δ: 2.29–2.33 (4H, m), 2.57 (4H, br.t), 2.65–2.74 (2H, m), 3.23 (4H, br.t), 3.39–3.45 (1H, m), 3.39 (1H, dd, J=6.8, 14.1 Hz), 3.96–4.03 (2H, m), 4.59 (1H, br.s), 5.11 (1H, dd, J=2.9, 7.1), 6.97–7.62 (18H, m)

EIMS(M/Z): 545 (M⁺)

Example 134

2-(2-Biphenylmethyl)-7-[4-(3,3-diphenyl-1-propyl)-piperazin-1-yl]-3,4-dihydro-2H-isoquinolin-1-one In the same manner as in Example 51, the title compound (28 mg) was prepared from the compound (50 mg) obtained in Example 82 and 2-(bromomethyl)biphenyl (32 mg).

¹H-NMR(CDCl₃) δ: 2.33 (4H, bs), 2.58 (4H, m), 2.82 (4H, m), 3.24 (4H, m), 4.02 (1H, t, J=7.0 Hz), 4.80 (2H, s), 6.98 (1H, dd J=2.4, 8.0 Hz), 7.31 (19H, m), 7.68 (1H, d, J=2.4 Hz)

TSIMS(M/Z): 592(M+H)⁺

Example 135

7-[4-(3,3-Diphenyl-1-propyl)piperazin-1-yl]-2-(tetrahydro-pyran-2-ylmethyl)-3,4-dihydro-2H-isoquinolin-1-one In the same manner as in Example 51, the title compound (32 mg) was prepared from the compound (30 mg) obtained in Example 82 and 2-(bromomethyl)tetrahydro-2H-pyran (19 mg).

¹H-NMR(CDCl₃) δ: 1.31 (1H, m), 1.49 (2H, m), 1.67 (1H, d, J=12.7 Hz), 1.84 (1H, m), 2.30 (4H, m), 2.57 (4H, t, J=4.8 Hz), 2.88 (2H, t, J=6.6 Hz), 3.23 (4H, t, J=4.8 Hz), 3.37 (1H, m), 3.62 (3H, m), 3.85 (1H, dd, J=3.4, 13.7 Hz), 3.93 (1H, td, J=1.7, 11.2 Hz), 4.01 (1H, t, J=7.6 Hz), 6.96 (1H, dd, J=2.8, 8.3 Hz), 7.04 (1H, d, J=8.3 Hz), 7.17 (3H, m), 7.27 (4H, m), 7.64 (1H, d, J=7.5 Hz)

TSIMS(m/z): 524(M+H)⁺

Example 136

7-[4-(3,3-Diphenyl-1-propyl)piperazin-1-yl]-2-(thiazol-4-yl)methyl-3,4-dihydro-2H-isoquinolin-1-one In the same manner as in Example 51, the title compound (20 mg) was prepared from the compound (50 mg) obtained in Example 82 and 4-chloromethylthiazole (19 mg).

¹H-NMR(CDCl₃) δ: 2.32 (4H, bs), 2.56 (4H, m), 2.90 (2H, t, J=6.6 Hz), 3.22 (4H, m), 3.68 (2H, t, J=6.6 Hz), 4.02 (1H, t, J=7.1 Hz), 4.94 (2H, s), 6.99 (1H, dd, J=2.6, 8.3 Hz), 7.06 (1H, d, J=8.3 Hz), 7.27 (11H, m), 7.66 (1H, d, J=2.6 Hz), 8.76 (1H, d, J=2.0 Hz)

TSIMS(M/Z): 523(M+H)⁺

Example 137

7-[4-(3,3-Diphenyl-1-propyl)piperazin-1-yl]-2-[(4-methylthiazol)-5-yl]methyl-3,4-dihydro-2H-isoquinolin-1-one In the same manner as in Example 51, the title compound (33 mg) was prepared from the compound (50 mg) obtained in Example 82 step and 5-chloromethyl-4-methylthiazole (20 mg).

¹H-NMR(CDCl₃) δ: 2.33 (4H, bs), 2.52 (3H, s), 2.58 (4H, m), 2.88 (2H, t, J=6.5 Hz), 3.24 (4H, m), 3.51 (2H, t, J=6.5

Hz), 4.01 (1H, t, J=7.1 Hz), 4.90 (2H, s), 6.99 (1H, dd, J=2.5, 8.3 Hz), 7.27 (10H, m), 7.67 (1H, d, J=2.5 Hz), 8.64 (1H, s)

TSIMS(M/Z): 537(M+H)$^+$

Example 138

7-[4-(3,3-Diphenyl-1-propyl)piperazin-1-yl]-2-(pyridine4-yl)methyl-3,4-dihydro-2H-isoquinolin-1-one In the same manner as in Example 51, the title compound (8 mg) was prepared from the compound (30 mg) obtained in Example 82 and 4-picolyl chloride hydrochloride (14 mg).

$^1$H-NMR(CDCl$_3$) δ: 2.30 (4H, m), 2.57 (4H, t, J=4.8 Hz), 2.88 (2H, bt, J=6.2 Hz), 3.23 (4H, t, J=4.8 Hz), 3.61 (2H, bt, J=6.2 Hz), 4.01 (1H, t, J=7.1 Hz), 4.93 (2H, s), 6.98 (1H, dd, J=2.4, 8.3 Hz), 7.05 (1H, d, J=8.3 Hz), 7.17 (3H, m), 7.26, (8H, m), 7.38 (1H, d, J=7.8 Hz), 7.61 (2H, m), 8.53 (1H, m)

TSIMS(m/z): 517(M+H)$^+$

Example 139

7-[4-(3,3-Diphenyl-1-propyl)piperazin-1-yl]-2-(pyridine-2-yl)methyl-3,4-dihydro-2H-isoquinolin-1-one In the same manner as in Example 51, the title compound (33 mg) was prepared from the compound (30 mg) obtained in Example 82 and 2-(chloromethyl)-pyridine hydrochloride (17 mg).

$^1$H-NMR(CDCl$_3$) δ: 2.30 (4H, m), 2.57 (4H, t, J=4.8 Hz), 2.88 (2H, t, J=6.6 Hz), 3.23 (4H, t, J=4.8 Hz), 3.61 (2H, t, J=6.6 Hz), 4.01 (1H, t, J=7.1 Hz), 4.90 (2H, s), 6.98 (1H, dd, J=2.4, 8.3 Hz), 7.05 (1H, d, J=8.3 Hz), 7.17 (3H, m), 7.26 (8H, m), 7.38 (1H, d, J=7.8 Hz), 7.63 (1H, dt, J=1.7, 7.8 Hz), 7.68 (1H, d, J=2.5 Hz), 8.53 (1H, d, J=4.4 Hz)

TSIMS(m/z): 517(M+H)$^+$

Example 140

6-[4-(3,3-Diphenyl-1-propyl)piperazin-1-yl]-2-phenyl-2,3-dihydro-1H-isoindol-1-one (a) Concentrated sulfuric acid (12 ml) was added to a solution of 2-methyl-5-nitrobenzoic acid (10.87 g) in ethanol (60 ml). The mixture was heated under reflux overnight. The reaction solution was concentrated under the reduced pressure. Water was then added to the residue. The mixture was extracted with diethyl ether. The extract was washed with water and saturated saline, and then dried over anhydrous magnesium sulfate. The solvent was then removed by distillation under the reduced pressure. The residue was purified by column chromatography on silica gel (hexane:ethyl acetate=4:1) to give ethyl 2-ethyl-5-nitrobenzoate (11.86 g).

$^1$H-NMR(CDCl$_3$) δ: 1.44 (3H, t, J=7.1 Hz), 2.72 (3H, s), 4.42 (2H, q, J=7.1 Hz), 7.43 (1H, d, J=8.4 Hz), 8.24 (1H, dd, J=2.5, 8.4 Hz), 8.76 (1H, d, J=2.5 Hz)

EIMS(M/Z): 209 (M$^+$)

(b) N-bromosuccinimide (4.63 g) and azobisisobutyronitrile (0.49 g) were added to a solution of the compound (4.18 g), obtained in step (a) just above, in a carbon tetrachloride (200 ml). The mixture was heated under reflux overnight at 90° C. The temperature of the reaction solution was returned to room temperature. Chloroform was added thereto. The mixture was washed with water, and then dried over anhydrous magnesium sulfate. The solvent was removed by distillation under the reduced pressure. The residue was purified by column chromatography on silica gel (hexane:ethyl acetate=10:1) to give ethyl 2-bromomethyl-5-nitrobenzoate (3.34 g).

$^1$H-NMR(CDCl$_3$) δ: 1.47 (3H, t, J=7.1 Hz), 4.47 (2H, q, J=7.1 Hz), 5.00 (2H, s), 7.68 (1H, d, J=8.5 Hz), 8.33 (1H, dd, J=2.5, 8.5 Hz), 8.81 (1H, d, J=2.5 Hz)

FABMS(M/Z): 288(M+H)$^+$ (c) Aniline (1.00 g) and diisopropylethylamine (1.52 g) were added to a solution of the compound (2.82 g), obtained in step (b) just above, in ethanol (45 ml). The mixture was stirred at room temperature for 4 hr. The reaction solution was concentrated under the reduced pressure. A 0.1 N aqueous citric acid solution was then added to the residue. The mixture was extracted with chloroform. The extract was washed with saturated saline, and then dried over anhydrous magnesium sulfate. The solvent was removed by distillation under the reduced pressure. The residue was purified by column chromatography on silica gel (hexane:ethyl acetate= 10:1) to give ethyl 5-nitro-2-phenylaminomethylbenzoate (2.52 g).

$^1$H-NMR(CDCl$_3$) δ: 1.45 (3H, t, J=7.1 Hz), 4.41–4.48 (3H, m), 4.81–4.82 (2H, m), 6.55 (2H, d, J=8.2 Hz), 6.73 (1H, t, J=7.3 Hz), 7.16 (2H, t, J=8.0 Hz), 7.78 (1H, d, J=8.6 Hz), 8.28 (1H, dd, J=2.5, 8.6 Hz), 8.82 (1H, d, J=2.5 Hz)

TSIMS(M/Z): 300 (M–H)$^+$ (d) 5% palladium-carbon (50 mg) was added to a suspension of the compound (1.5 g), obtained in step (c) just above, in ethanol (12.5 ml), followed by catalytic reduction. The mixture was stirred at room temperature overnight. The reaction solution was filtered through Celite. The solvent was then removed from the filtrate by distillation under the reduced pressure. The residue was purified by column chromatography on silica gel (hexane:ethyl acetate=4:1) to give ethyl 5-amino-2-phenylaminomethylbenzoate (1.22 g).

$^1$H-NMR(CDCl$_3$) δ: 1.35 (3H, t, J=7.1 Hz), 3.72 (2H, brs), 4.29–4.40 (3H, m), 4.49 (2H, s), 6.61–6.69 (3H, m), 6.76 (1H, dd, J=2.6, 8.2 Hz), 7.14 (2H, t, J=7.9 Hz), 7.26–7.28 (2H, m)

TSIMS(M/Z): 271(M+H)$^+$ (e) Sodium ethoxide (0.32 g) was added to a solution of the compound (1.14 g), obtained in step (d) just above, in ethanol (210 ml). The mixture was stirred at 60° C. for 1.5 hr. The reaction solution was concentrated under the reduced pressure. A saturated aqueous sodium hydrogencarbonate solution was then added to the residue. The mixture was extracted with chloroform. The organic layer was then washed with saturated saline, and then was dried over anhydrous magnesium sulfate. The solvent was then removed by distillation under the reduced pressure. The precipitated crystals were collected by suction filtration, washed with hexane, and then dried to give 6-amino-2-phenyl-2,3-dihydro-1H-isoindol-1-one (0.88 g).

$^1$H-NMR(CDCl$_3$) δ: 3.87 (2H, brs), 4.77 (2H, s), 6.91 (1H, dd, J=2.3, 8.3 Hz), 7.14–7.22 (2H, m), 7.28 (1H, d, J=8.0 Hz), 7.42 (2H, t, J=8.0 Hz), 7.86 (2H, d, J=8.0 Hz)

EIMS(M/Z): 224 (M$^+$)

(f) Bis(2-chloroethyl)amine hydrochloride (57 mg) was added to a solution of the compound (45 mg), obtained in step (e) just above, in n-butanol (2 ml). The mixture was stirred at 110° C. for 139 hr. The reaction solution was concentrated under the reduced pressure. The residue was then purified by column chromatography on silica gel (chloroform:methanol=5:1) to give 2-phenyl-6-(piperazin-1-yl)-2,3-dihydro-1H-isoindol-1- one hydrochloride (26 mg).

¹H-NMR(CD₃OD) δ: 3.36–3.38 (4H, m), 3.45–3.48 (4H, m), 4.92 (2H, S), 7.22 (1H, t, J=7.4 Hz), 7.37–7.46 (4H, m), 7.56 (1H, d, J=8.3 Hz), 7.84 (2H, dd, J=1.1, 8.9 Hz)

TSIMS(M/Z): 294(M+H)⁺

(g) Potassium carbonate (42 mg) and 3,3-diphenyl-1-propyl bromide (29 mg) were added to a solution of the compound (18 mg), obtained instep (f) just above, in N,N-dimethylformamide (1 ml). The mixture was stirred at 50° C. for 6 hr. The temperature of the system was returned to room temperature. A 0.1 N aqueous citric acid solution was then added thereto. The mixture was extracted with chloroform. The organic layer was washed with saturated saline, and then dried over anhydrous magnesium sulfate. The solvent was then removed by distillation under the reduced pressure. The residue was purified by column chromatography on silica gel (hexane:ethyl acetate=1:1) to give the title compound: (11 mg).

¹H-NMR(CDCl₃) δ: 2.27–2.39 (4H, m), 2.60 (4H, t, J=4.9 Hz), 3.28 (4H, t, J=4.9 Hz), 4.03 (1H, t, J=7.3 Hz), 4.78 (2H, s), 7.15–7.20 (4H, m), 7.21–7.32 (8H, m), 7.35–7.46 (4H, m), 7.86 (2H, dd, J=1.1, 8.8 Hz)

TSIMS(M/Z): 488(M+H)⁺

Example 141

2-Benzyl-7-[4-(3,3-diphenyl-1-propyl)piperazin-1-yl]-4,4-dimethyl-3,4-dihydro-2H-isoquinolin-1-one (a) 4-Methoxybenzylamine (8.3 g) was added to homophthalic anhydride (8.1 g). The mixture was stirred at 180° C. overnight. Water was added to the reaction solution. The mixture was then extracted with ethyl acetate. The organic layer was then dried over anhydrous magnesium sulfate. The solvent was removed by distillation under the reduced pressure. The residue was purified by column chromatography on silica gel (hexane:ethyl acetate=8:2) to give 2-(4-methoxybenzyl)-4H-isoquinoline-1,3-dione (11.8 g).

¹H-NMR(CDCl₃) δ: 3.78 (3H, s), 4.05 (2H, s), 5.13 (2H, s), 6.83 (2H, s), 7.41 (5H, m), 8.22 (1H, m)

EIMS(M/Z): 281 (M⁺)

(b) The compound (10.0 g) obtained in step (a) just above was dissolved in N,N-dimethylformamide (40 ml). Sodium hydride (4.2 g) was added under cooling at 0° C. to the solution. The mixture was stirred for 20 min. Thereafter, methyl iodide (14.9 g) was added, and the mixture was stirred at room temperature for 4 hr. Ethyl acetate and water were added to the reaction solution, followed by stirring for 5 min. The mixture was extracted with ethyl acetate. The organic layer was then dried over anhydrous magnesium sulfate. The solvent was then removed by distillation under the reduced pressure. The residue was purified by column chromatography on silica gel (hexane:ethyl acetate=1:1) to give 2-(4-methoxybenzyl)-4,4-dimethyl-4H-isoquinoline-1,3-dione (10.9 g).

¹H NMR(CDCl₃) δ: 1.61 (6H, s), 3.77 (3H, s), 5.13 (2H, s), 6.83 (2H, m), 7.43 (4H, m), 7.62 (1H, m), 8.23 (1H, m)

EIMS(M/Z): 309 (M⁺)

(c) The compound (6.0 g) obtained in step (b) just above was dissolved in a mixed solvent (acetonitrile:water=4:1) (40 ml). Diammonium cerium nitrate (26.6 g) was added to the solution. The mixture was stirred at room temperature for 3 hr. The reaction solution was extracted with ethyl acetate. The organic layer was then dried over anhydrous magnesium sulfate. The solvent was then removed by distillation under the reduced pressure. The residue was purified by column chromatography on silica gel (hexane:ethyl acetate=8:2) to give 4,4-dimethyl-4H-isoquinoline-1,3-dione (10.9 g).

¹H-NMR(CDCl₃) δ: 1.67 (6H, s), 7.47 (2H, m), 7.68 (1H, m), 8.23 (1H, m), 8.43 (1H, bs)

FABMS(M/Z): 190(M+H)⁺

(d): The compound (2.0 g) obtained in step (c) just above was dissolved in methanol (100 ml). Sodium boron hydride (1.7 g) was added to the solution. The mixture was stirred at room temperature for 3 hr. Hydrochloric acid-methanol (50 ml) was added to the reaction solution, and the mixture was stirred at room temperature for one hr. The reaction solution was then extracted with ethyl acetate. The organic layer was dried over anhydrous magnesium sulfate. The solvent was then removed by distillation under the reduced pressure. The residue was purified by column chromatography on silica gel (hexane:ethyl acetate=1:1) to give 3-methoxy-4,4-dimethyl-3,4-dihydro-2H-isoquinolin-1-one (1.8 g).

¹H-NMR(CDCl₃) δ: 1.32 (3H, s), 1.50 (3H, s), 3.36 (3H, s), 4.27 (1H, d, J=4.6 Hz), 7.34 (2H, m), 7.53 (1H, m), 7.73 (1H, bs), 8.09 (1H, m)

EIMS(M/Z): 205 (M⁺)

(e) The compound (1.3 g) obtained in step (d) just above was dissolved in diethyl ether (15 ml). Phosphorus pentachloride (1.1 g) was added to the solution. The mixture was stirred at room temperature for 30 min. The solvent was then removed by distillation under the reduced pressure. Glyme (20 ml) and sodium boron hydride (1.1 g) were added to the residue. The mixture was stirred at room temperature for one hr. Water was added to the reaction solution, followed by stirring. The mixture was then extracted with ethyl acetate. The organic layer was then dried over anhydrous magnesium sulfate. The solvent was then removed by distillation under the reduced pressure. The residue was purified by column chromatography on silica gel (chloroform:methanol=30:1) to give 4,4-dimethyl-3,4-dihydro-2H-isoquinolin-1-one (1.8 g).

¹H-NMR(CDCl₃) δ: 1.36 (6H, s), 3.33 (2H, d, J=3.0 Hz), 6.51 (1H, bs), 7.35 (2H, m), 7.50 (1H, m), 8.09 (1H, m)

TSIMS(M/Z): 176(M+H)⁺

(f) In the same manner as in step (c) of Example 1, 4,4-dimethyl-7-nitro-3,4-dihydro-2H-isoquinolin-1-one (450 mg) was prepared from the compound (600 mg) obtained in step (e) just above.

¹H-NMR(CDCl₃) δ: 1.43 (6H, s), 3.40 (2H, d, J=3.1 Hz), 7.54 (1H, d, J=8.6 Hz), 8.35 (1H, dd, J=2.5, 8.6 Hz), 8.93 (1H, d, J=2.5 Hz)

EIMS(M/Z): 220 (M⁺)

(g) In the same manner as in step (d) of Example 1,7-amino-4,4-dimethyl-3,4-dihydro-2H-isoquinolin-1-one (340 mg) was prepared from the compound (450 mg) obtained in step (f) just above.

¹H-NMR(CDCl₃) δ: 1.31 (6H, s), 3.27 (2H, d, J=2.9 Hz), 6.26 (1H, bs), 6.83 (1H, dd, J=2.2, 8.0 Hz), 7.12 (1H, d, J=8.0 Hz), 7.39 (1H, d, J=2.2 Hz)

FABMS(M/Z): 191(M+H)⁺

(h) In the same manner as in step (e) of Example 1, 4,4-dimethyl-7-piperazin-1-yl-3,4-dihydro-2H-isoquinolin-1-one (340 mg) was prepared from the compound (480 mg) obtained in step (g) just above.

¹H NMR(CDCl₃) δ: 1.32 (6H, s), 3.03 (4H, m), 3.19 (4H, m), 3.28 (2H, d, J=3.0 Hz), 6.36 (1H, dd, J=2.9, 8.6 Hz), 7.22 (1H, d, J=8.6 Hz), 7.62 (1H, d, J=2.9 Hz)

EIMS(M/Z): 259 (M⁺)

(i) In the same manner as in step (f) of Example 1,7-[4-(3,3-diphenyl-1-propyl)piperazin-1-yl]-4,4-dimethyl-3,4- dihydro-2H-isoquinolin-1-one (250 mg) was prepared from the compound (400 mg) obtained in step (h) just above and 3,3-diphenyl 1-propyl bromide (500 mg).

$^1$H-NMR(CDCl$_3$) δ: 1.32 (6H, s), 2.20 (4H, bs), 2.57 (4H, m), 3.25 (4H, m), 3.28 (2H, d, J=3.1 Hz), 4.02 (1H, t, J=7.1 Hz), 6.20 (1H, bs), 7.05 (1H, dd, J=2.8, 8.5 Hz), 7.24 (11H, m), 7.62 (1H, d, J=2.8 Hz)

EIMS(M/Z): 453 (M$^+$)

(j) In the same manner as in Example 51, the title compound (20 mg) was prepared from the compound (50 mg) obtained in step (i) and benzyl bromide (20 mg).

$^1$H-NMR(CDCl$_3$) δ: 1.18 (6H, s), 2.34 (4H, bs), 2.58 (4H, m), 3.19 (2H, s), 3.26 (4H, m), 4.02 (1H, t, J=7.4 Hz), 4.79 (2H, s), 7.00 (1H, dd, J=2.8, 8.7 Hz), 7.16 (1H, d, J=8.7 Hz), 7.27 (14H, m), 7.73 (1H, d, J=2.8 Hz)

FABMS(M/Z): 544 (M+H)$^+$

The compounds prepared in the above examples had the following respective structures.

Example 1

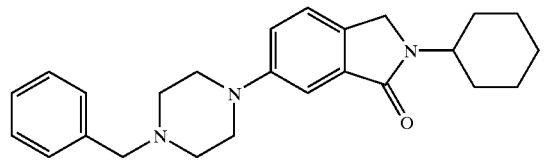

Example 2

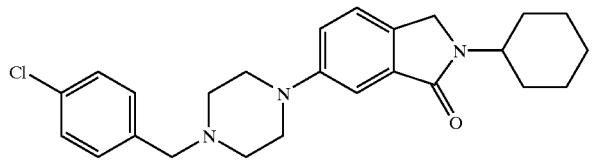

Example 3

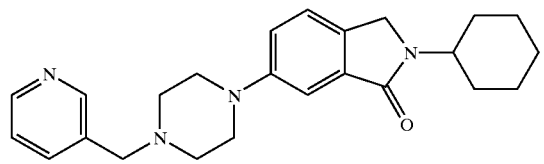

Example 4

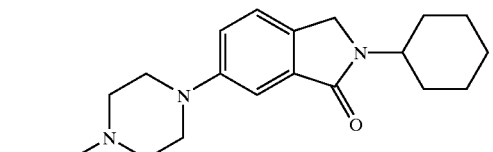

Example 5

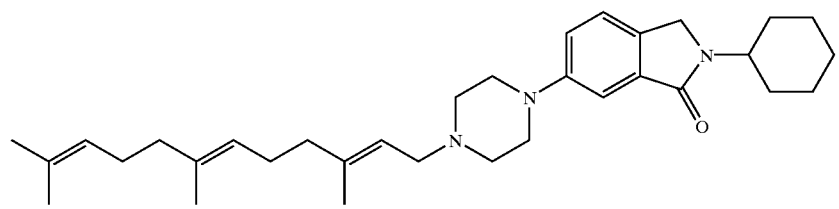

Example 6

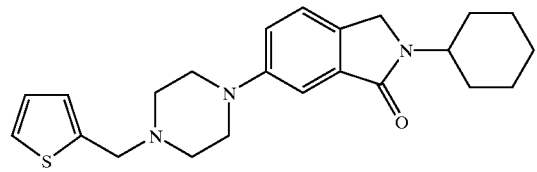

Example 7

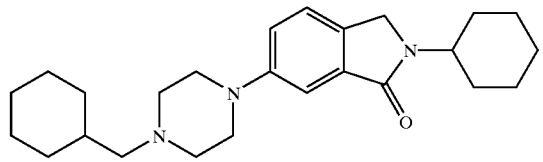

Example 8

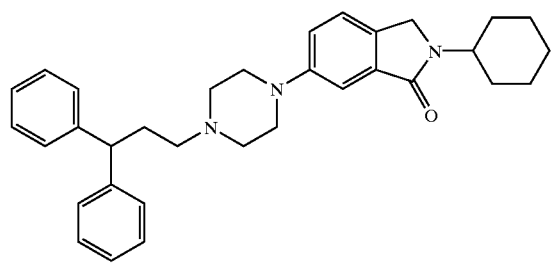

Example 9

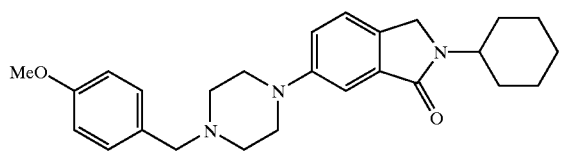

Example 10

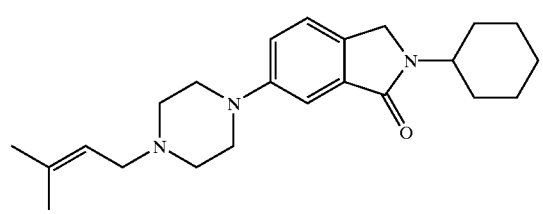

Example 11

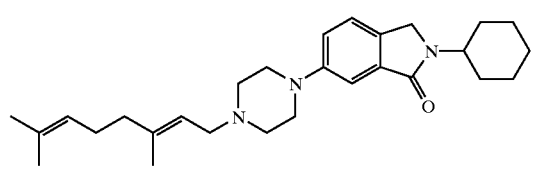

-continued
Example 12
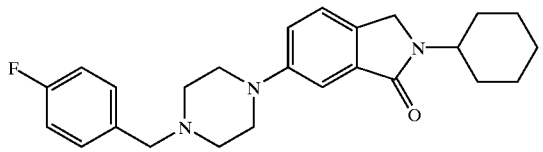
Example 13
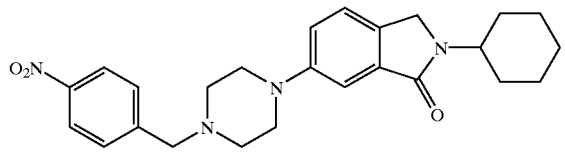
Example 14
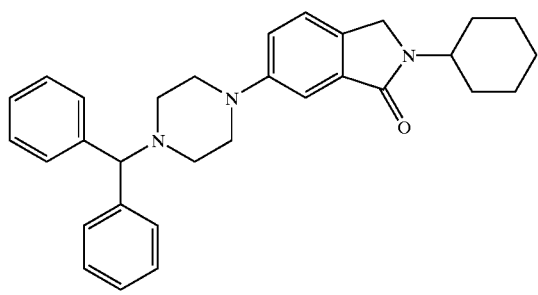
Example 15
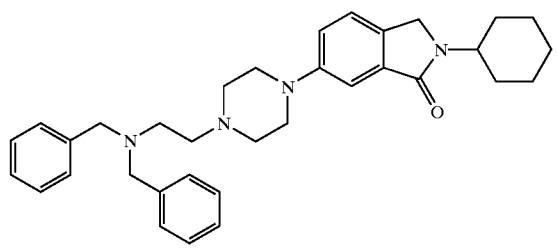
Example 16
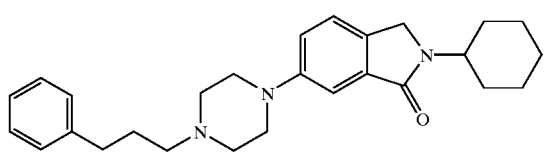
Example 17
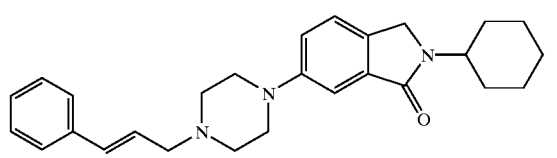
Example 18
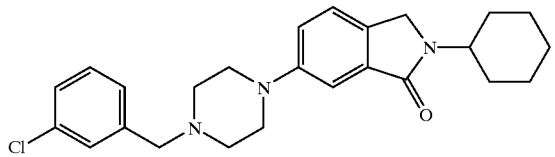
Example 19
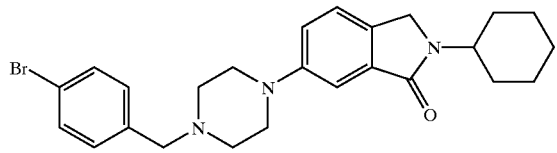
Example 20
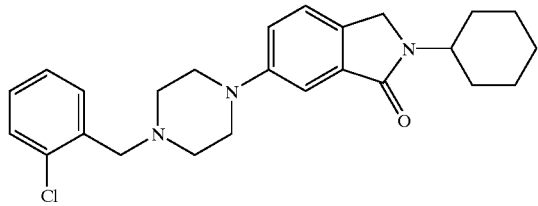
Example 21
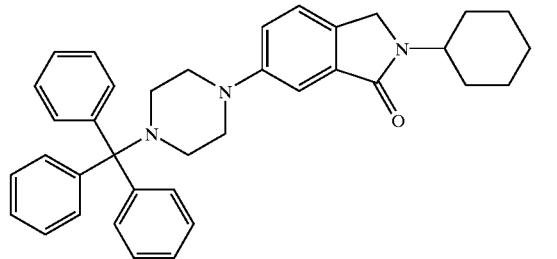
Example 22
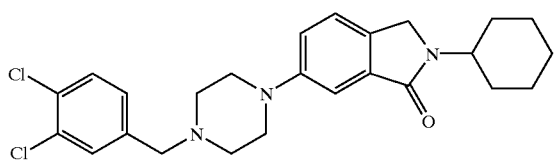
Example 23
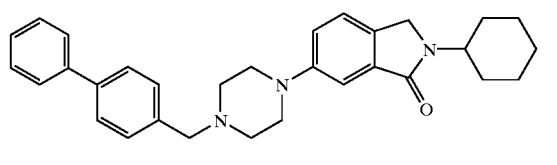
Example 24
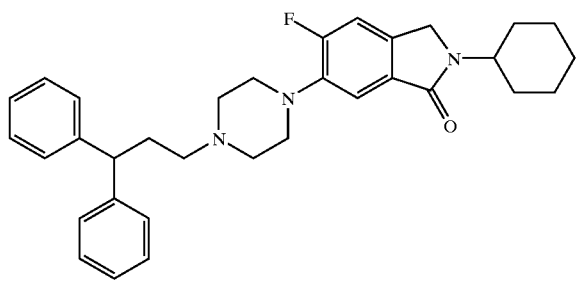
Example 25
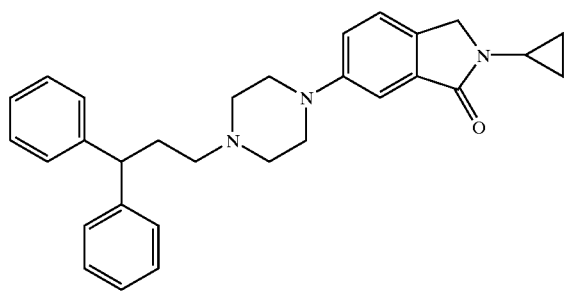

-continued
Example 26
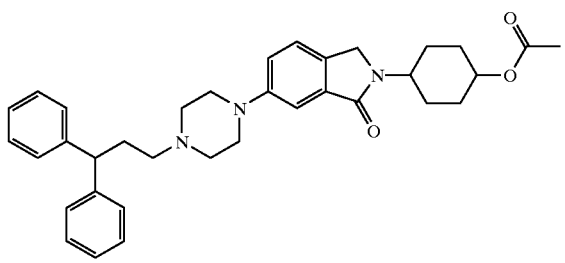
Example 27
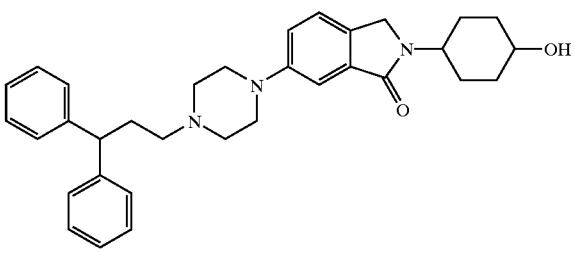
Example 28
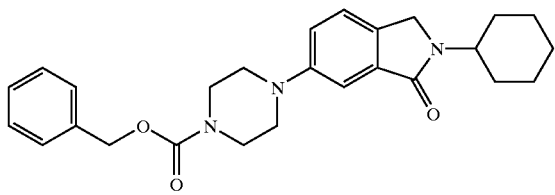
Example 29
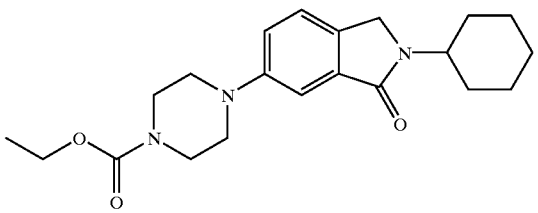
Example 30
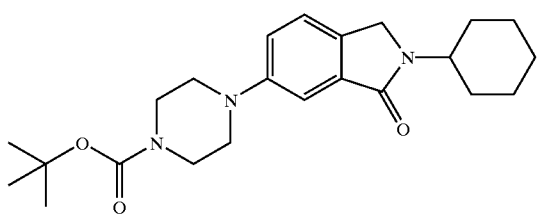
Example 31
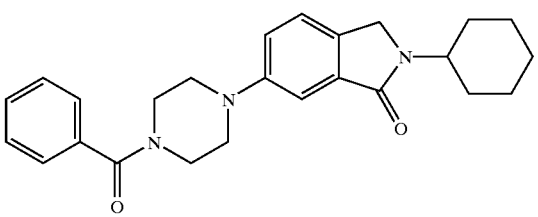
Example 32
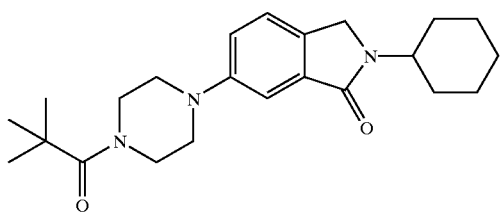
Example 33
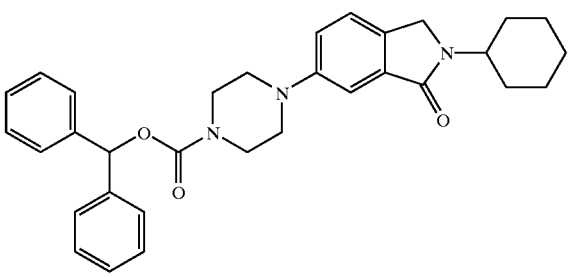
Example 34
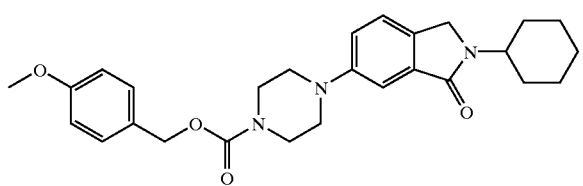
Example 35
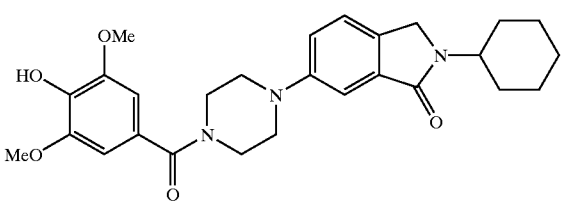
Example 36
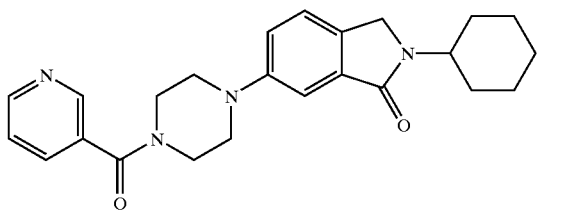
Example 37
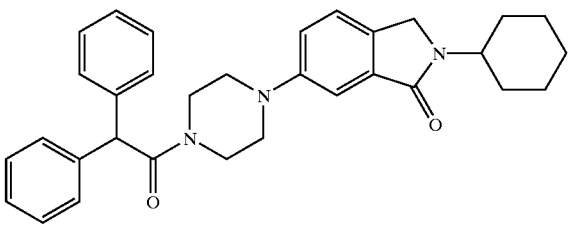

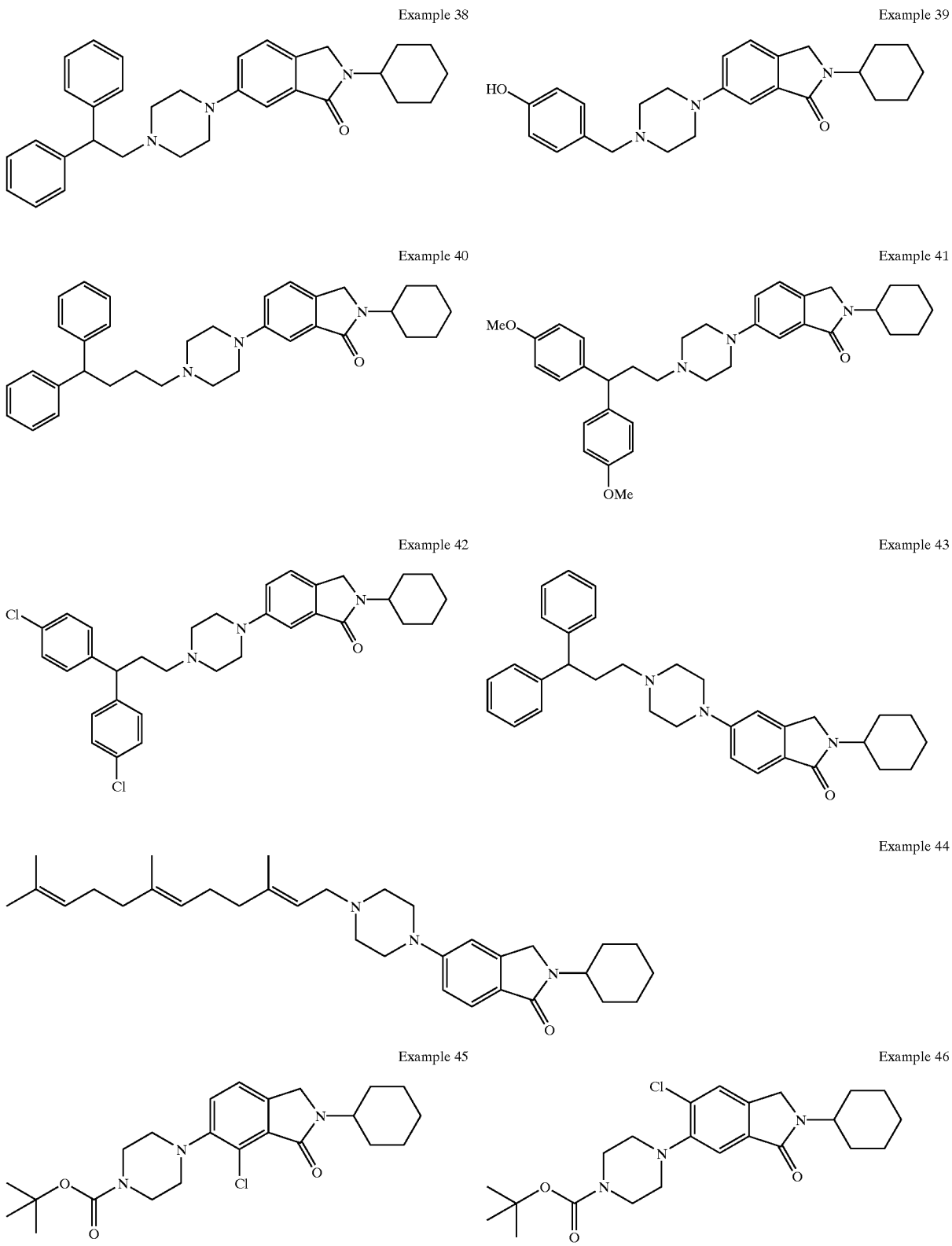

-continued
Example 47
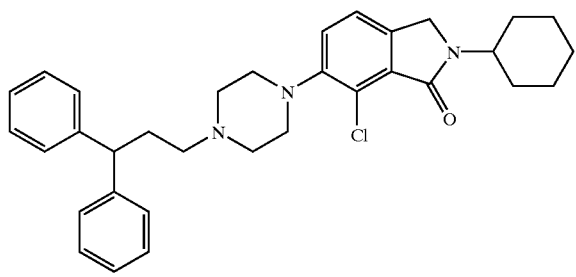
Example 48
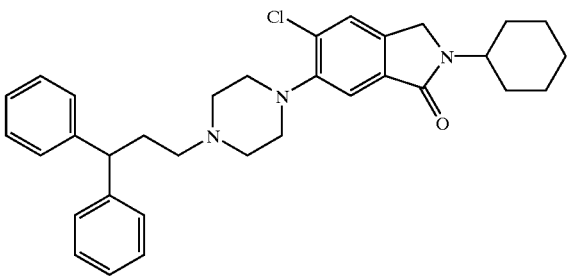
Example 49
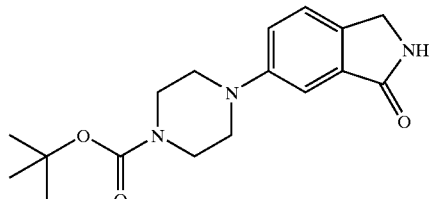
Example 50
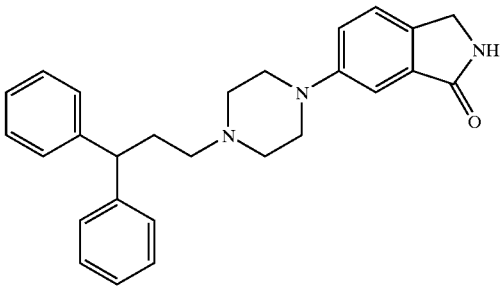
Example 51
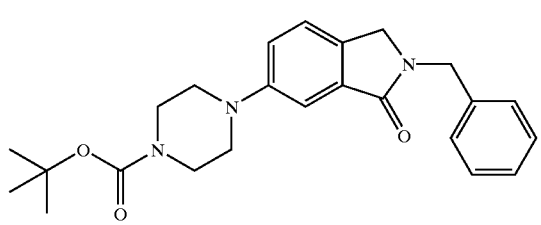
Example 52
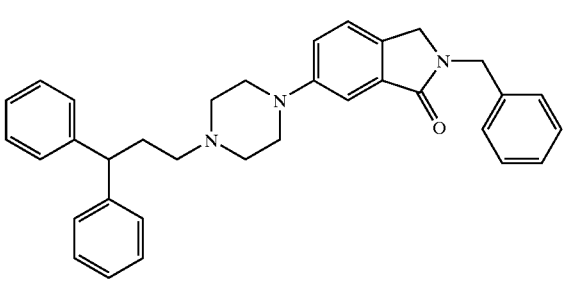
Example 53
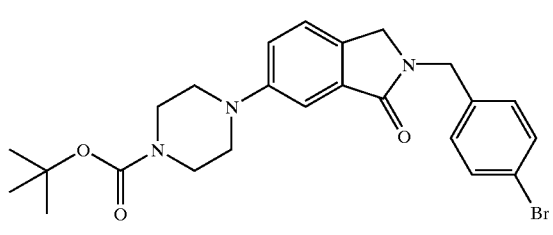
Example 54
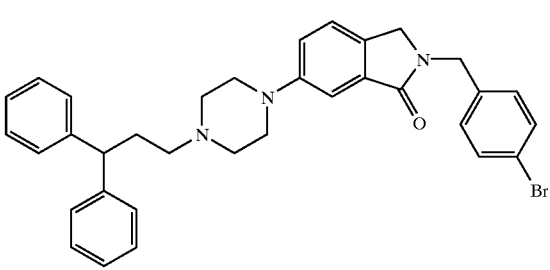
Example 55
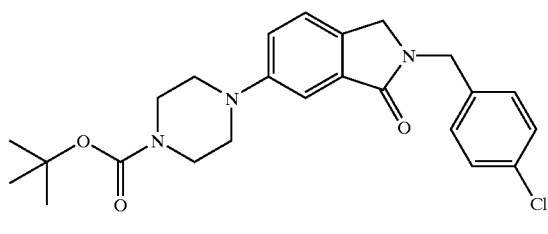
Example 56
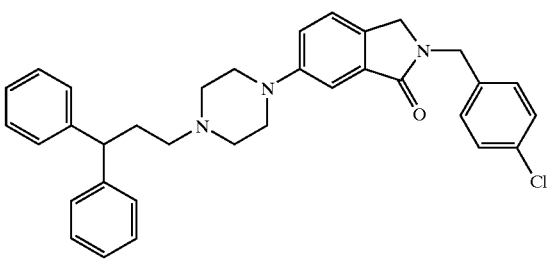

Example 57
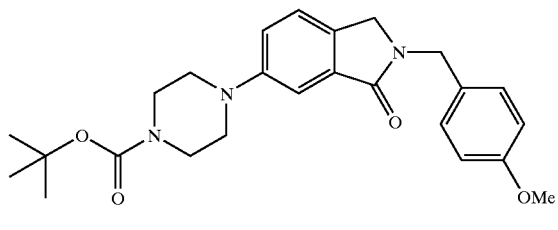
Example 58
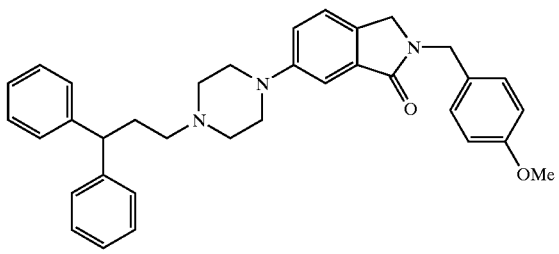
Example 59
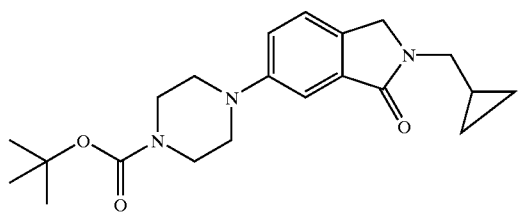
Example 60
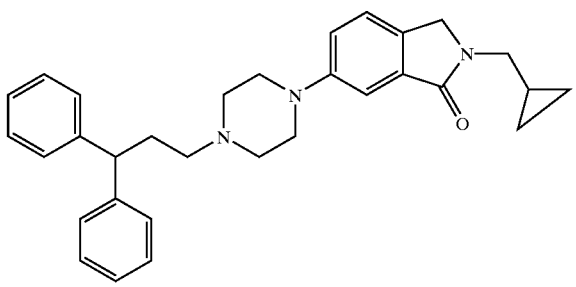
Example 61
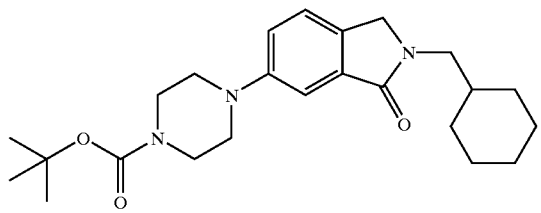
Example 62
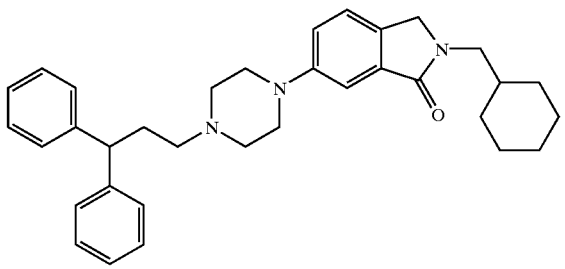
Example 63
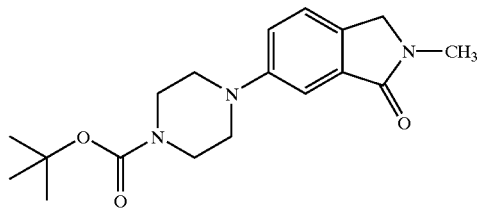
Example 64
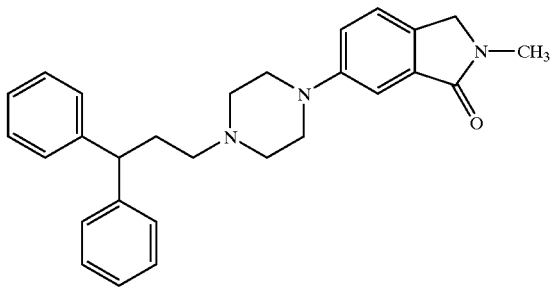
Example 65
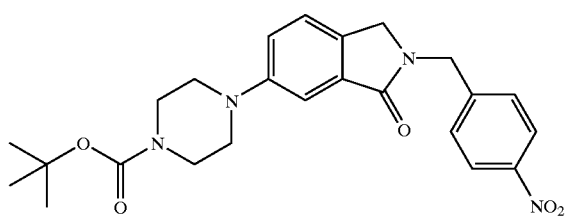
Example 66
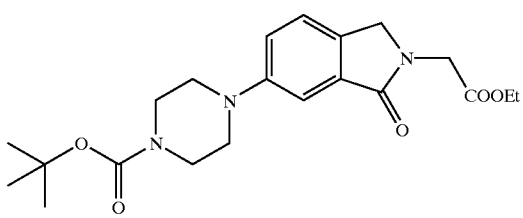

Example 67
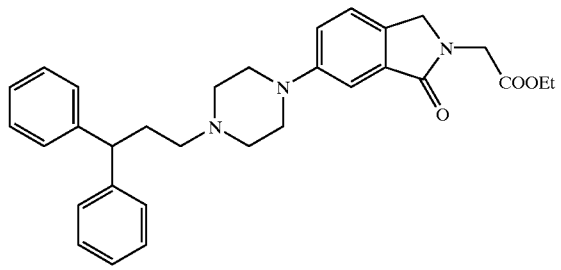
Example 68
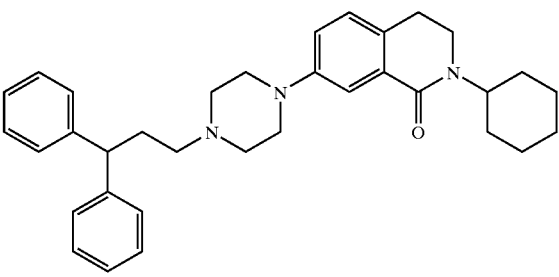
Example 69
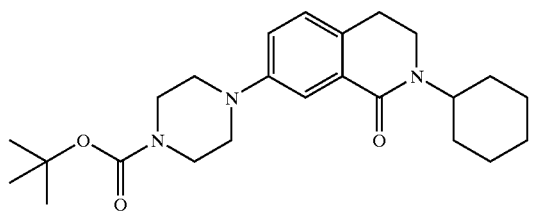
Example 70
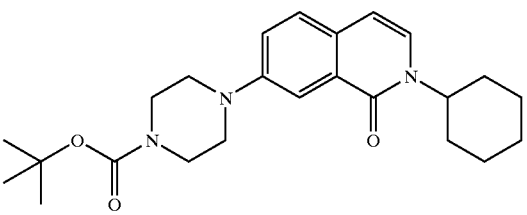
Example 71
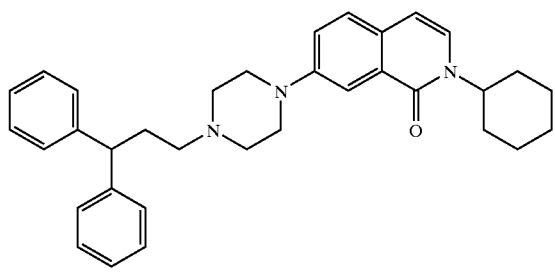
Example 72
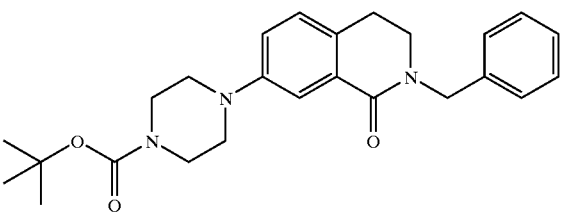
Example 73
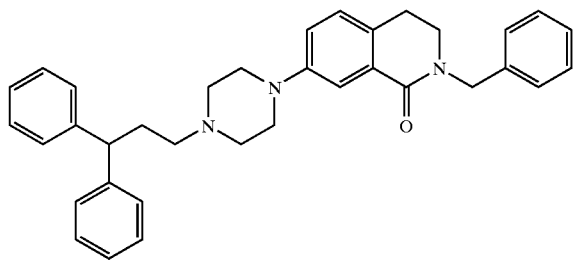
Example 74
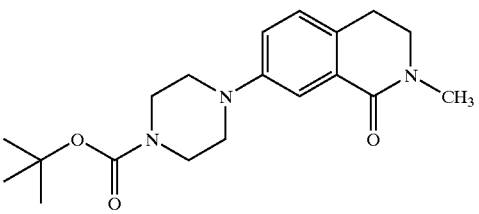
Example 75
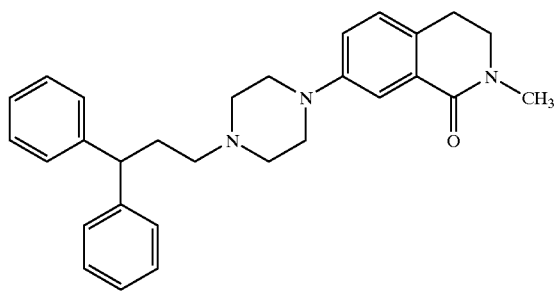
Example 76
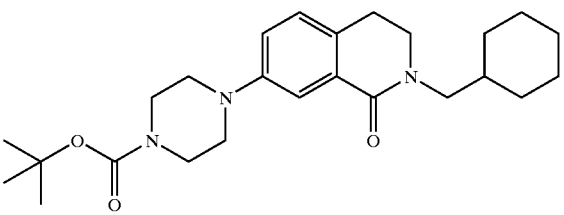

-continued
Example 77
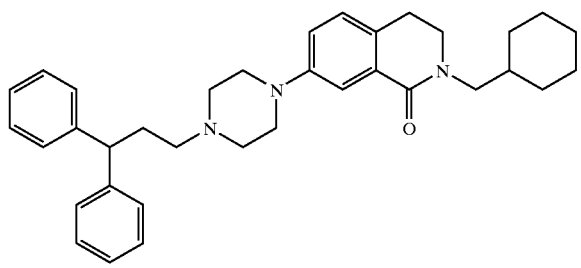
Example 78
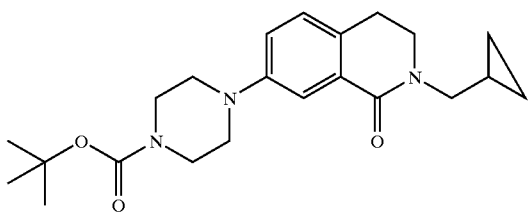
Example 79
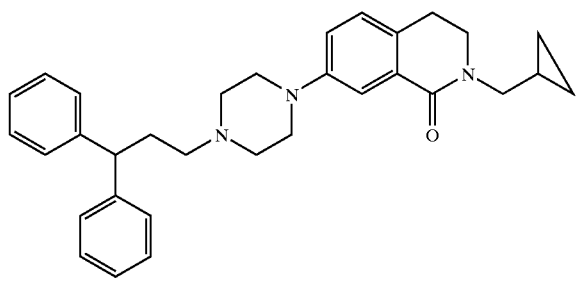
Example 80
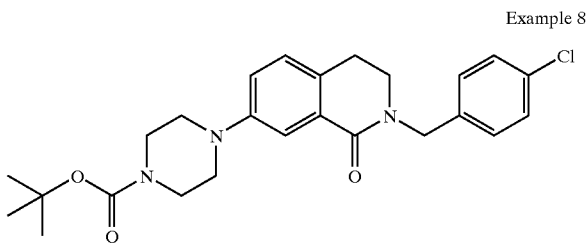
Example 81
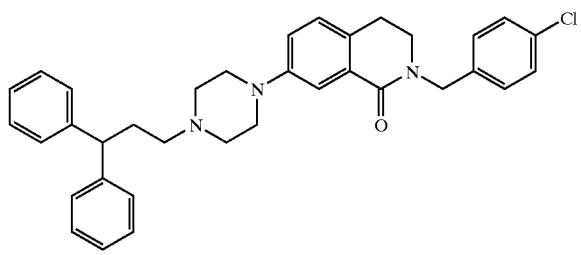
Example 82
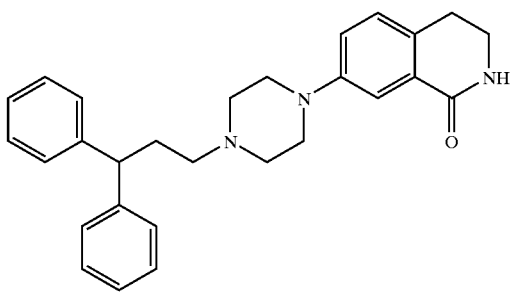
Example 83
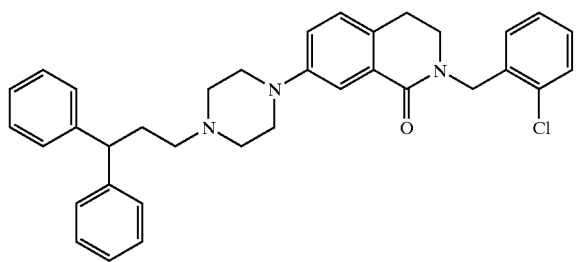
Example 84
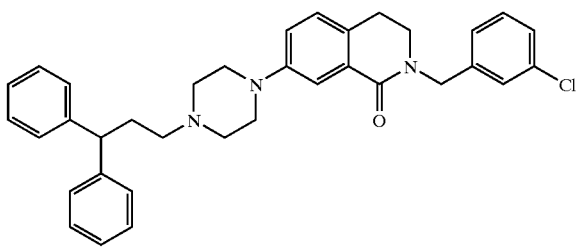
Example 85
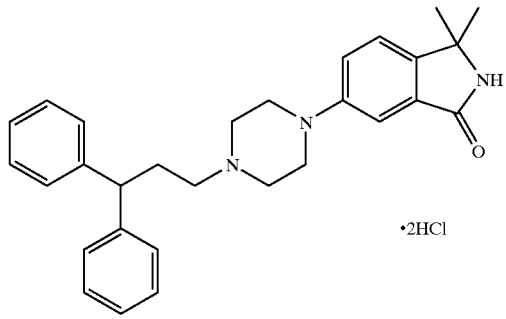
·2HCl
Example 86
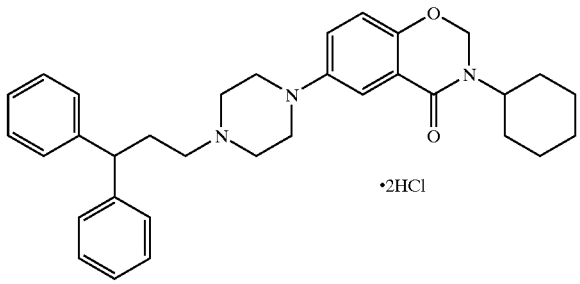
·2HCl Example 87
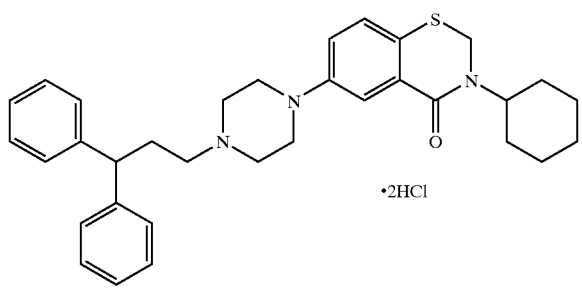
Example 88
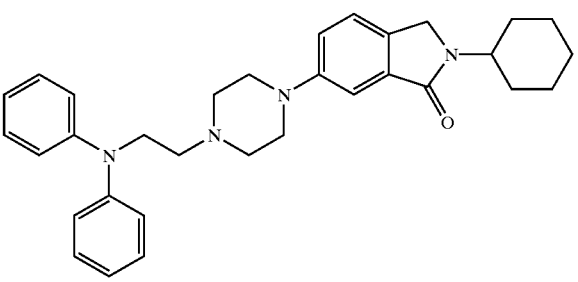
Example 89
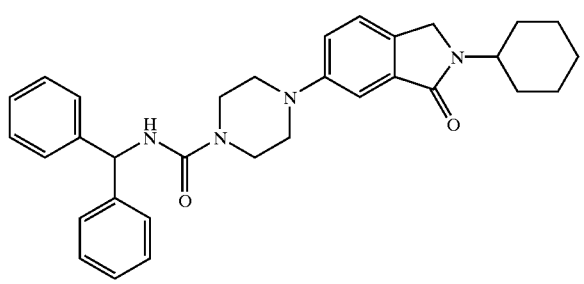
Example 90
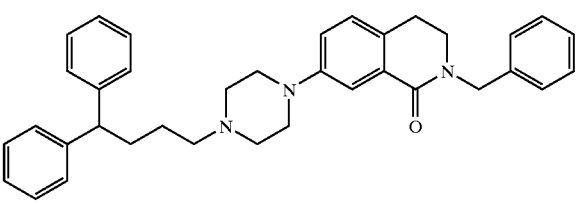
Example 91
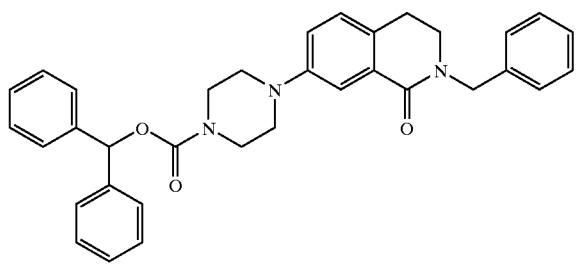
Example 92
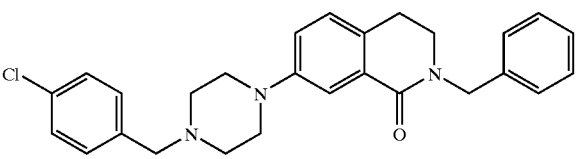
Example 93
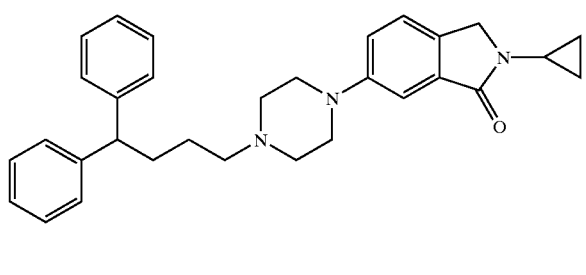
Example 94
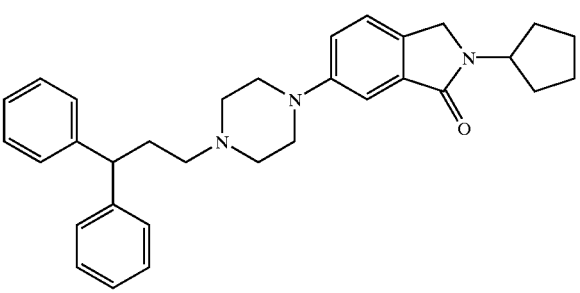
Example 95
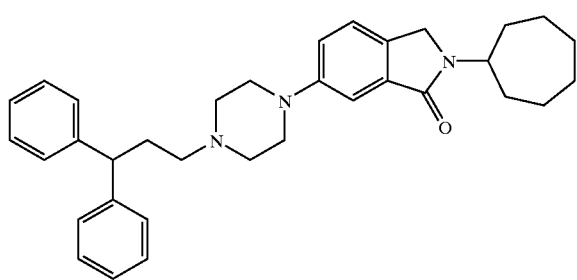
Example 96
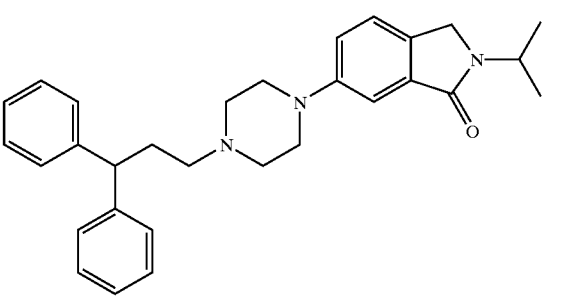

Example 97
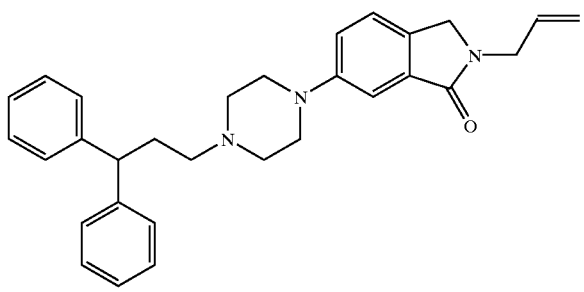
Example 98
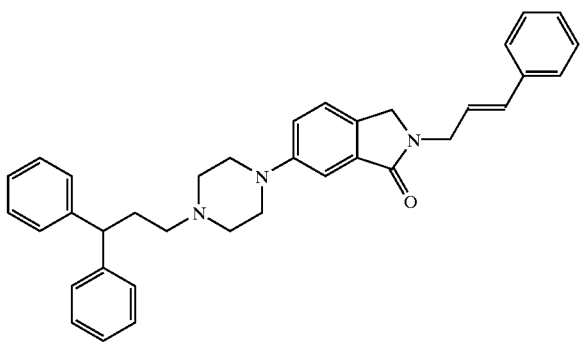
Example 99
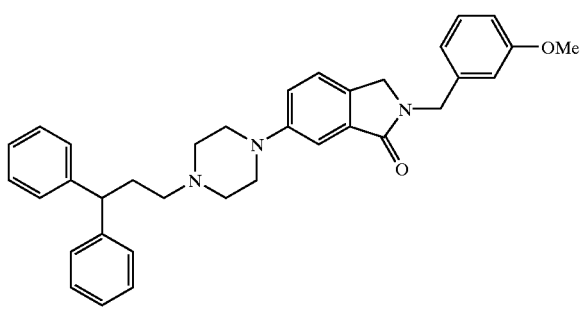
Example 100
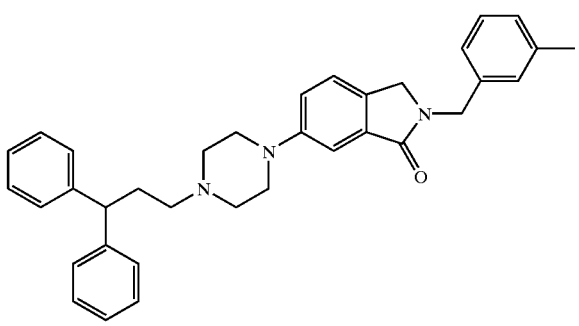
Example 101
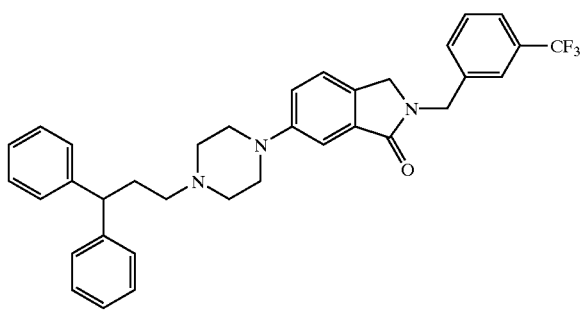
Example 102
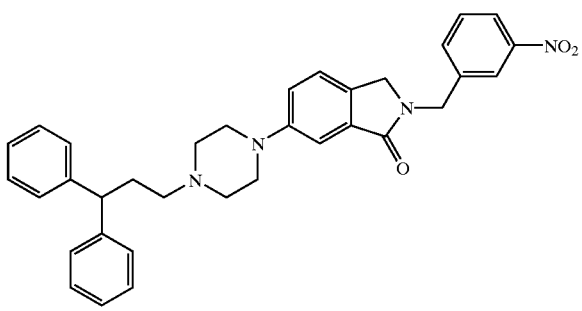
Example 103
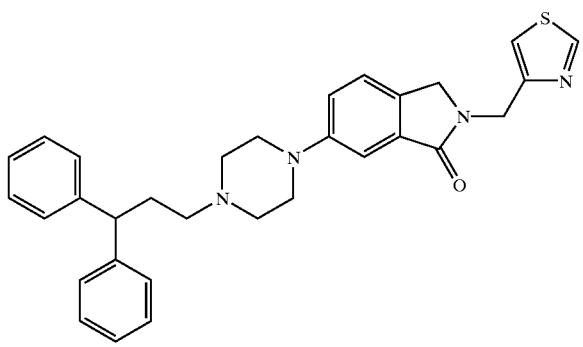
Example 104
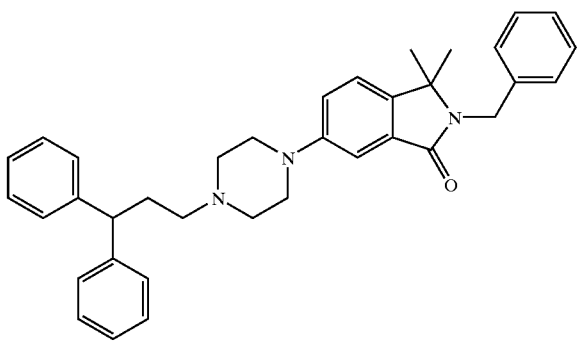

-continued
Example 105
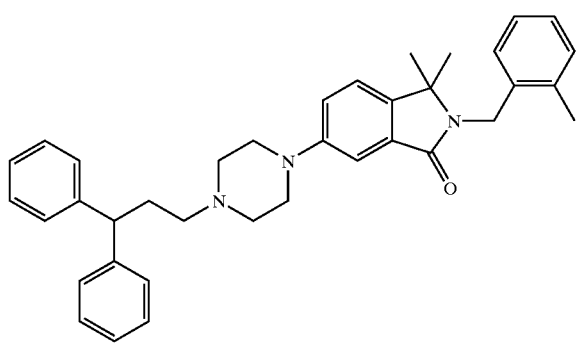
Example 106
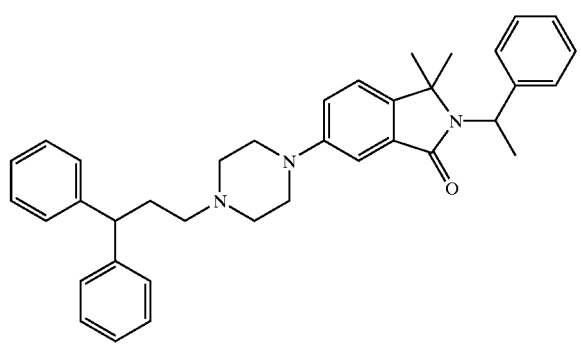
Example 107
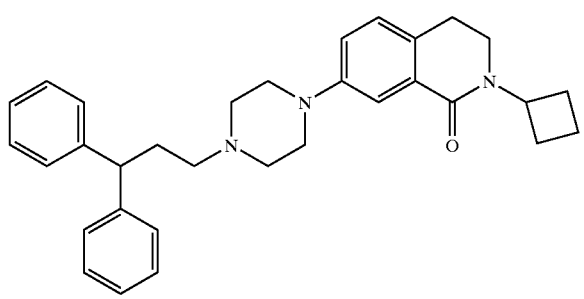
Example 108
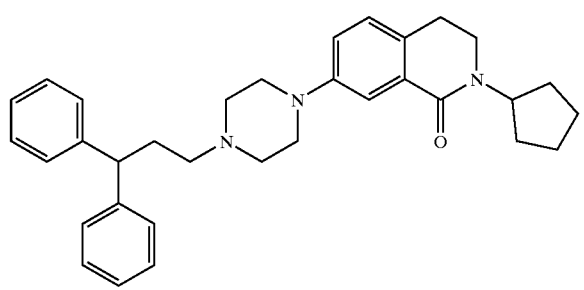
Example 109
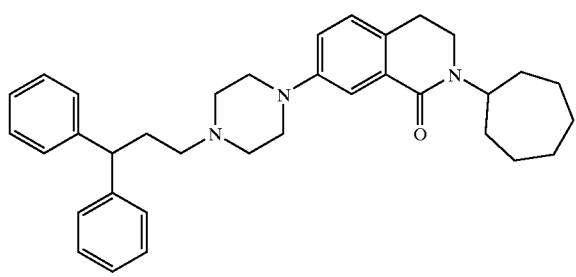
Example 110
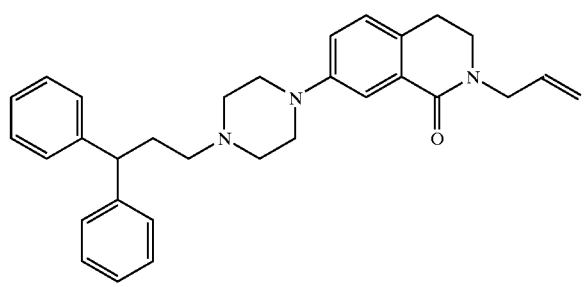
Example 111
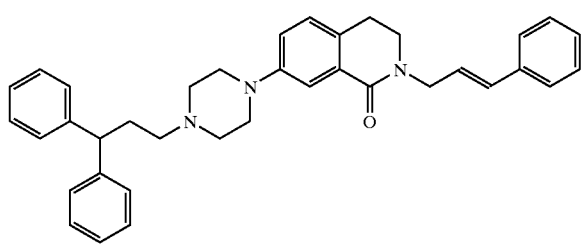
Example 112
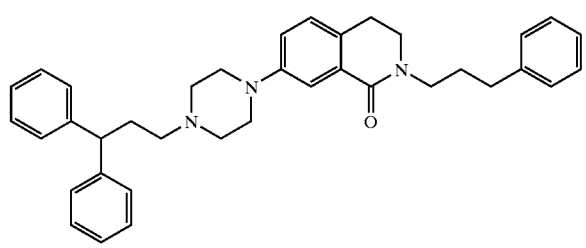
Example 113
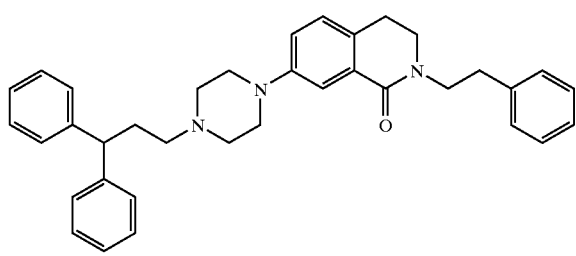
Example 114
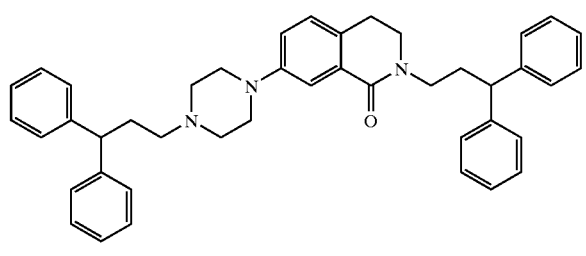

-continued
Example 115
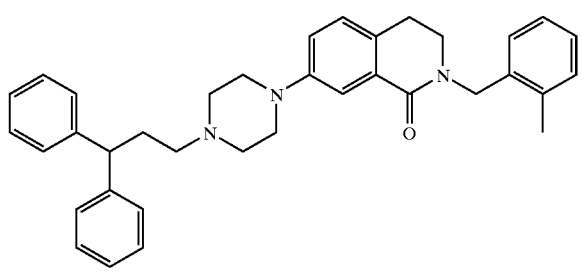
Example 116
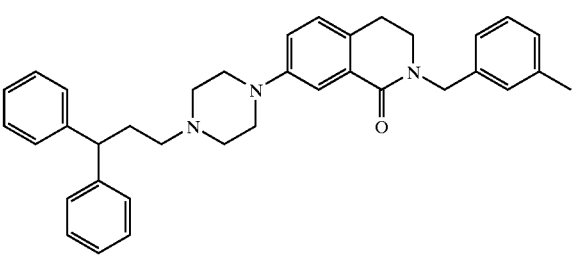
Example 117
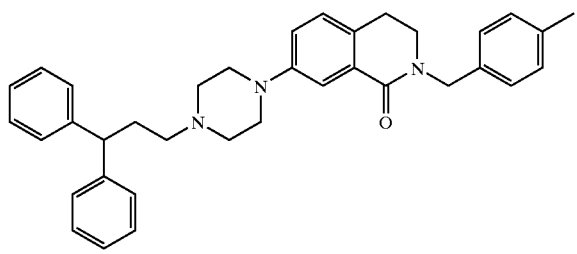
Example 118
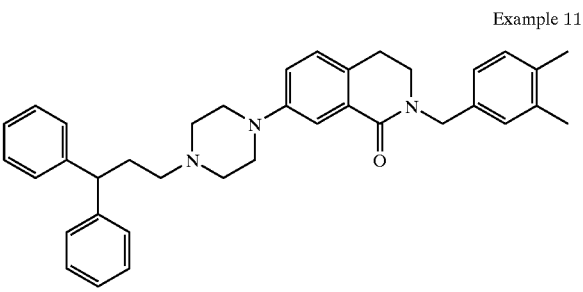
Example 119
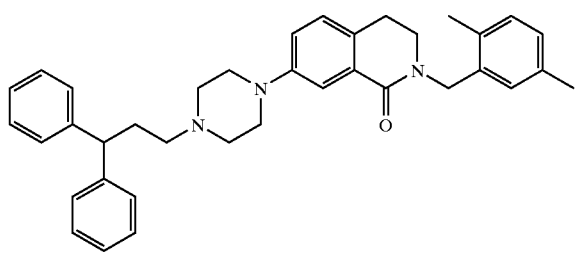
Example 120
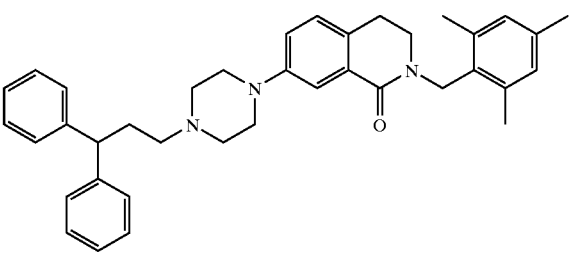
Example 121
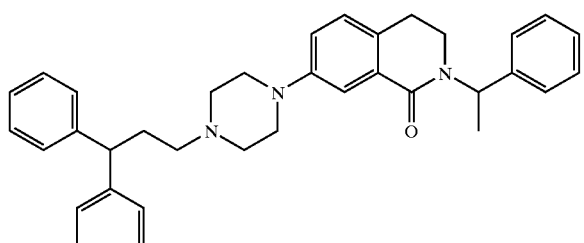
Example 122
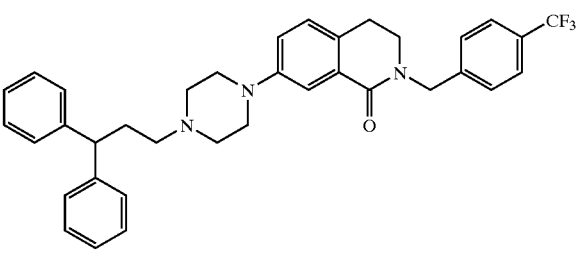
Example 123
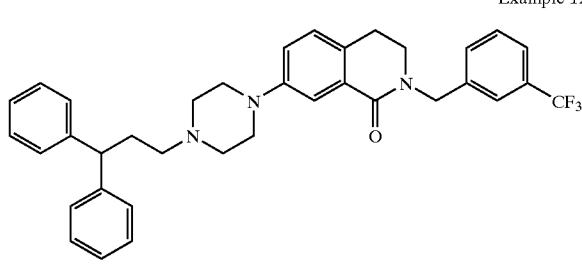
Example 124
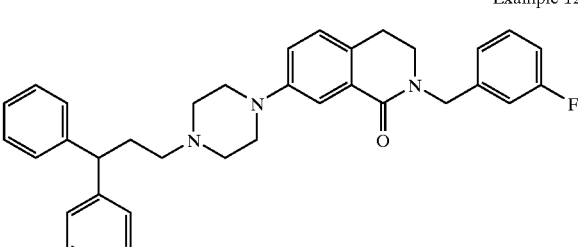

Example 125
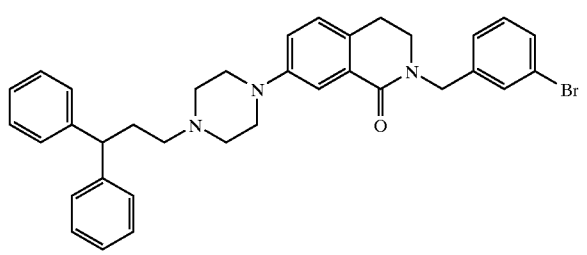
Example 126
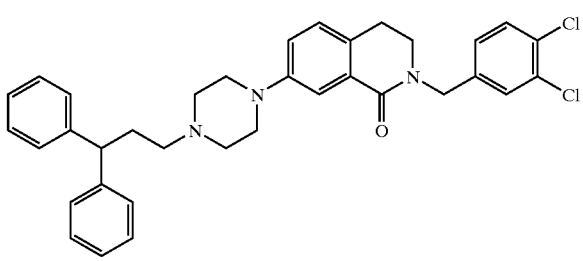
Example 127
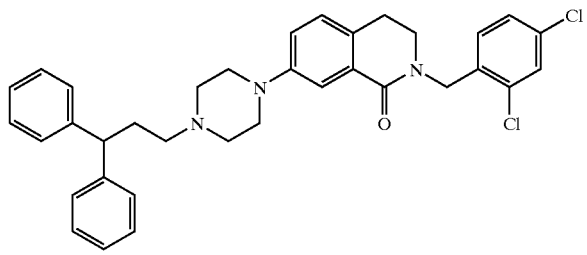
Example 128
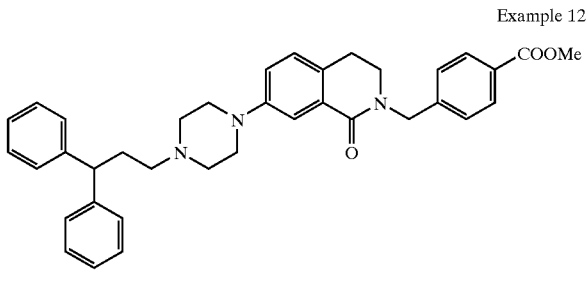
Example 129
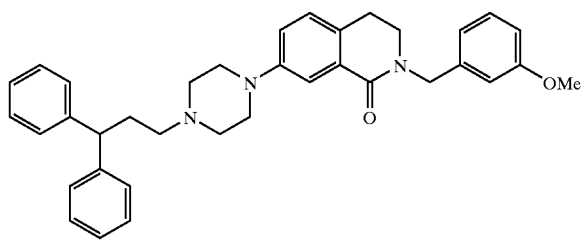
Example 130
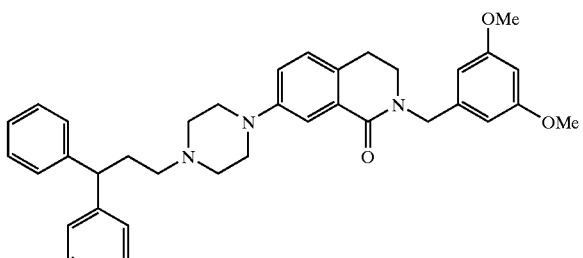
Example 131
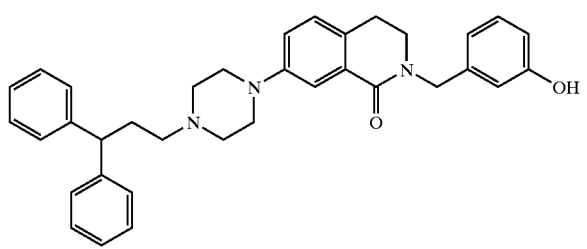
Example 132
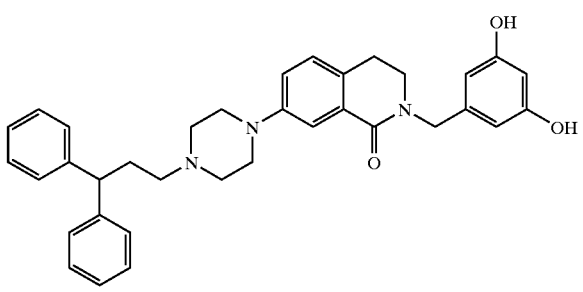
Example 133
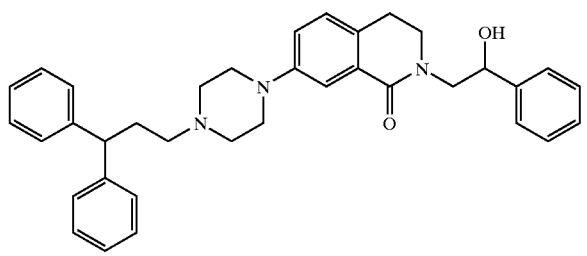
Example 134
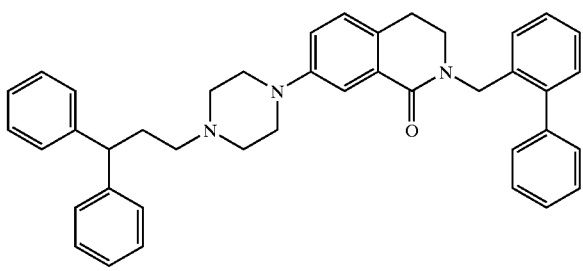

-continued

Example 135

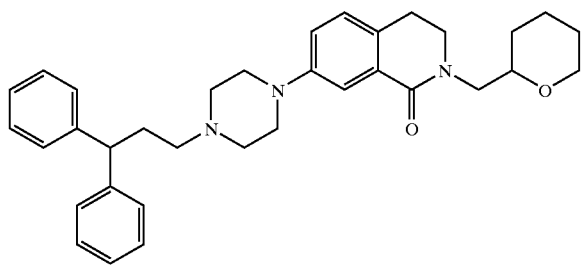

Example 136

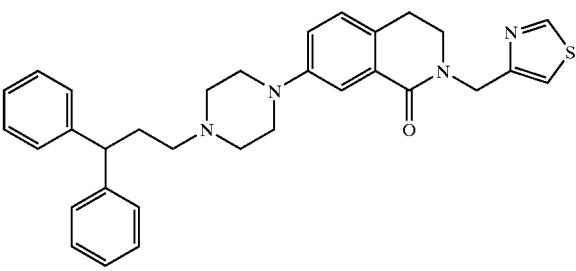

Example 137

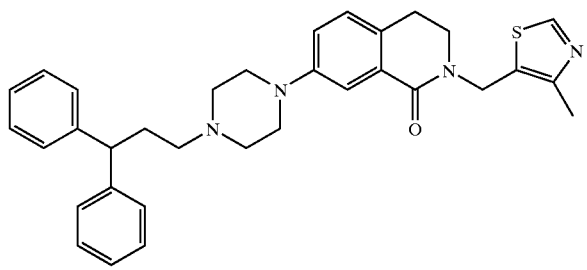

Example 138

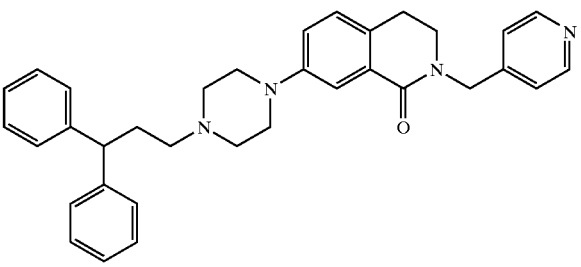

Example 139

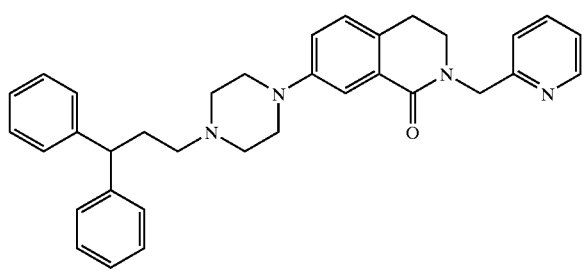

Example 140

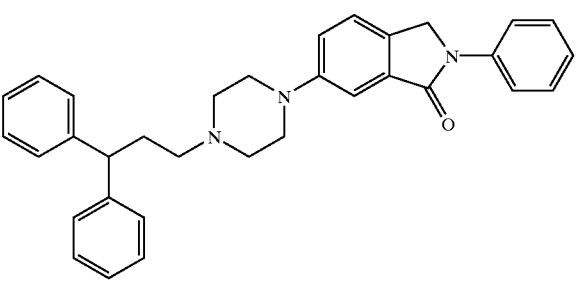

Example 141

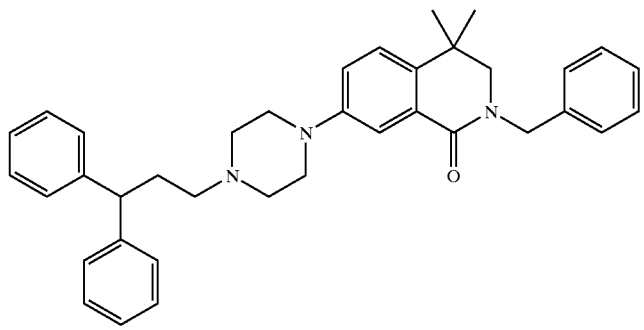

Preparation Example 1

| Tablet | |
|---|---|
| Compound of Example 8 | 2.5 g |
| Lactose | 12 g |
| 6% HPC lactose | 8 g |
| Potato starch | 2 g |
| Magnesium stearate | 0.5 g |
| Total | 25 g |

All the above ingredients were intimately mixed together, and the mixture was compressed into 1000 tablets.

Preparation Example 2

| Capsule | |
|---|---|
| Compound of Example 127 | 2.5 g |
| Lactose | 18 g |
| Potato starch | 4 g |
| Magnesium stearate | 0.5 g |
| Total | 25 g |

All the above ingredients were intimately mixed together, and the mixture was filled into 1000 hard capsules.

Test Example 1

Inhibitory activity against biosynthesis of triglycerides

The inhibitory activity of the compounds according to the present invention against the biosynthesis of triglycerides were studied using cell strain HepG2 derived from human hepatoma.

The test was carried out by the method of Nagata et al. (Biochem. Pharmacol., 40, 843 (1990)) and the method of Furukawa et al. (J. Biol. Chem., 267, 22630 (1992)) which had been partly modified. Specifically, HepG2 cells were cultivated in a Dulbecco's modified Eagle's medium (DMEM), containing 10% fetal calf serum (FCS), 100 units/ml penicillin, and 100 μg/ml streptomycin, placed in 96-well plates. Thereafter, the medium was replaced with DMEM containing 1% bovine serum albumin, and the test compound was simultaneously added to a final concentration of 3 μM or was not added, followed by cultivation. Three hr after the replacement of the medium, $^{14}$C-acetic acid was added to a final concentration of 1 mM, followed by cultivation for additional 4 hr. The cells were washed with a phosphate buffer (pH 7.5) containing 150 mM sodium chloride. Thereafter, lipid within the cells was extracted with n-butanol. After the extraction, the extract was evaporated to dryness under a nitrogen gas stream. The residue was dissolved in a small amount of chloroform. The solution was developed in thin-layer chromatography (developing solvent petroleum ether:diethyl ether:acetic acid=90:15:3), and a $^{14}$C-triglyceride fraction was isolated. The amount of $^4$C-triglycerides produced was then quantitatively determined with a liquid scintillation counter (Beckman, LS-6500).

The inhibition (%) of the biosynthesis of triglycerides was calculated by the following equation:

Inhibition (%) of biosynthesis of triglycerides={1-(amount of $^{14}$C-triglycerides produced in the presence of drug)/(amount of $^{14}$C-triglycerides produced in the absence of drug)}×100.

Test Example 2

Inhibitory activity against secretion of apolipoprotein B

The inhibitory activity of the compounds according to the present invention against the secretion of apolipoprotein B was studied using cell strain HepG2 derived from hepatoma.

The test was carried out by the method of Nagata et al. (Biochem. Pharmacol., 40, 843 (1990)) and the method of Furukawa et al. (J. Biol. Chem., 267, 22630 (1992)) which had been partly modified. Specifically, HepG2 cells were cultivated in a Dulbecco's modified Eagle's medium (DMEM), containing 10% fetal calf serum (FCS), 100 units/ml penicillin, and 100 μg/ml streptomycin, placed in 96-well plates. Thereafter, the medium was replaced with DMEM containing 1% bovine serum albumin, and the test compound was simultaneously added to a final concentration of 3 μM or not added, followed by cultivation. Three hr after the replacement of the medium, acetic acid was added to a final concentration of 1 mM, followed by cultivation for additional 4 hr. The amount of apolipoprotein B secreted in the supernatant of the culture thus obtained was quantitatively determined by the sandwich ELISA method. In this case, goat anti-human apolipoprotein B polyclonal antibody (CHEMICON) was used as a primary antibody, and mouse anti-human apolipoprotein B monoclonal antibody peroxidase conjugate (BIOSYS) was used as a secondary antibody.

The inhibition (%) against the secretion of apolipoprotein B was calculated by the following equation:

Inhibition (%) of secretion of apolipoprotein B={1-(amount of apolipoprotein B secreted in the presence of drug)/(amount of apolipoprotein B secreted in the absence of drug)}×100

For the compounds obtained in Examples 5, 8, 30, and 68, the inhibition against the secretion of apolipoprotein B and the inhibition against the biosynthesis of triglycerides were determined by Test Examples 1 and 2. The results are shown in Table 1.

| Compounds of examples | Inhibition (%) | |
| --- | --- | --- |
| | Apolipoprotein B | Triglycerides |
| 5 | 56 | 90 |
| 8 | 70 | 79 |
| 30 | 68 | 89 |
| 68 | 61 | 64 |

It was demonstrated that the novel nitrogen-containing heterocyclic ring compounds according to the present invention had the inhibitory activity against the biosynthesis of triglycerides and the inhibitory activity against the secretion of apolipoprotein B in the liver.

Test Example 3

Acute Toxicity Test

An acute toxicity test was carried out using mice and rats by a conventional method. Specifically, the compound of Example 8 was orally administered at a dose of 200 mg/kg to ddY mice (male) or wistar rats (male), and the mice and the rats were observed for 8 days. As a result, in all the cases, the mice and the rats survived, and any change in general states, such as a reduction in body weight, did not occur.

What is claimed is:

1. A compound represented by formula (I) and pharmaceutically acceptable salt and solvate thereof:

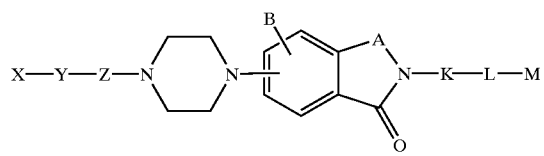

(I)

wherein

A represents group —CR$^1$R$^2$—(CH$_2$)$_i$— wherein R$^1$ and R$^2$, which may be the same or different, represent a hydrogen atom or alkyl having 1 to 6 carbon atoms and i is an integer of 1,

—CH═CH—,

—O—CH$_2$—, or

—S(O)$_j$—CH$_2$— wherein j is an integer of 0 to 2;

B represents a hydrogen or halogen atom;

X represents

—CR$^3$R$^4$R$^5$ wherein R$^3$, R$^4$, and R$^5$, which may be the same or different, each represent a hydrogen atom or phenyl, provided that any one of R$^3$, R$^4$, and R$^5$ represents phenyl and one or more hydrogen atoms on phenyl may be substituted by a halogen atom, hydroxyl, nitro, phenyl, or alkoxy having 1 to 6 carbon atoms, —(CH$_2$—CH═C(CH$_3$)—CH$_2$)$_p$—CH$_2$CH═C(CH$_3$)$_2$ wherein p is an integer of 0 to 2, alkyl having 1 to 18 carbon atoms, cycloalkyl having 3 to 8 carbon atoms, phenyl optionally substituted by hydroxy, a halogen atom, nitro, alkoxy having 1 to 6 carbon atoms, or phenyl, or cinnamyl optionally substituted by hydroxy, a halogen atom, nitro, phenyl, or alkoxy having 1 to 6 carbon atoms;

Y represents —(CH$_2$)$_q$— wherein q is an integer of 1 to 6,

—CH=CH—, or a bond;

Z represents a bond;

K represents alkylene having 1 to 6 carbon atoms optionally substituted by hydroxy, a halogen atom, alkyl having 1 to 6 carbon atoms, or alkoxy having 1 to 6 carbon atoms, or represents a bond;

L represents —CH=CH— or a bond; and

M represents a hydrogen atom, alkyl having 1 to 6 carbon atoms optionally substituted by hydroxy, a halogen atom, amino, alkoxy having 1 to 6 carbon atoms, or alkoxycarbonyl having 1 to 4 carbon atoms, cycloalkyl having 3 to 8 carbon atoms optionally substituted by hydroxy, a halogen atom, amino, alkoxy having 1 to 6 carbon atoms, alkylcarbonyloxy having 1 to 4 carbon atoms, or alkoxycarbonyl having 1 to 4 carbon atoms, phenyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms, a five- or six-membered, saturated or unsaturated heterocyclic ring containing up to two hetero atoms optionally substituted by alkyl having 1 to 4 carbon atoms, biphenyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms, or diphenylmethyl optionally substituted by alkyl, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms.

2. The compound according to claim 1, wherein

A represents group —CR$^1$R$^2$—(CH$_2$)$_i$— wherein R$^1$ and R$^2$ each represent a hydrogen atom and i is an integer of 1;

B represents a hydrogen or halogen atom;

X represents —CR$^3$R$^4$R$^5$ wherein R$^3$, R$^4$, and R$^5$ each are as defined in claim 1, —(CH$_2$—CH=C(CH$_3$)—CH$_2$)$_p$—CH$_2$CH=C(CH$_3$)$_2$ wherein p is as defined in claim 1, alkyl having 1 to 18 carbon atoms, cycloalkyl having 3 to 8 carbon atoms, phenyl optionally substituted by hydroxy, a halogen atom, nitro, alkoxy having 1 to 6 carbon atoms, or phenyl, or cinnamyl optionally substituted by hydroxy, a halogen atom, nitro, phenyl, or alkoxy having 1 to 6 carbon atoms;

Y represents —(CH$_2$)$_q$— wherein q is an integer of 1 to 6, or a bond;

Z represents a bond;

K represents alkylene having 1 to 6 carbon atoms optionally substituted by hydroxy, a halogen atom, alkyl having 1 to 6 carbon atoms, or alkoxy having 1 to 6 carbon atoms, or represents a bond;

L represents —CH=CH— or a bond; and

M represents a hydrogen atom, alkyl having 1 to 6 carbon atoms optionally substituted by hydroxy, a halogen atom, amino, alkoxy having 1 to 6 carbon atoms, or alkoxycarbonyl having 1 to 4 carbon atoms, cycloalkyl having 3 to 8 carbon atoms optionally substituted by hydroxy, a halogen atom, amino, alkoxy having 1 to 6 carbon atom, alkylcarbonyloxy having 1 to 4 carbon atoms, or alkoxycarbonyl having 1 to 4 carbon atoms, phenyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms, a five- or six-membered, saturated or unsaturated heterocyclic ring containing up to two hetero atoms optionally substituted by alkyl having 1 to 4 carbon atoms, biphenyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms, or diphenylmethyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms.

3. The compound according to claim 1, which is represented by formula (II):

(II)

wherein

A represents group —CR$^1$R$^2$—(CH$_2$)$_i$— wherein R$^1$, R$^2$, and i each are as defined in claim 1,

—CH=CH—,

—O—CH$_2$—, or

—S(O)$_j$—CH$_2$— wherein j is as defined in claim 1;

B represents a hydrogen or halogen atom;

X represents —CR$^3$R$^4$R$^5$ wherein R$^3$, R$^4$, and R$^5$ each are as defined in claim 1, —(CH$_2$—CH=C(CH$_3$)—CH$_2$)$_p$—CH$_2$CH=C(CH$_3$)$_2$ wherein p is as defined in claim 1, alkyl having 1 to 18 carbon atoms, cycloalkyl having 3 to 8 carbon atoms, phenyl optionally substituted by hydroxy, a halogen atom, nitro, alkoxy having 1 to 6 carbon atoms, or phenyl, or cinnamyl optionally substituted by hydroxy, a halogen atom, nitro, phenyl, or alkoxy having 1 to 6 carbon atoms;

Y represents —(CH$_2$)$_q$— wherein q is as defined in claim 1, or a bond;

Z represents carbonyl or a bond;

K represents alkylene having 1 to 6 carbon atoms optionally substituted by hydroxy, a halogen atom, alkyl having 1 to 6 carbon atoms, or alkoxy having 1 to 6 carbon atoms, or represents a bond;

L represents —CH=CH— or a bond; and

M represents a hydrogen atom, alkyl having 1 to 6 carbon atoms optionally substituted by hydroxy, a halogen atom, amino, alkoxy having 1 to 6 carbon atoms, or alkoxycarbonyl having 1 to 4 carbon atom, cycloalkyl having 3 to 8 carbon atoms optionally substituted by hydroxy, a halogen atom, amino, alkoxy having 1 to 6 carbon atoms, alkylcarbonyloxy having 1 to 4 carbon atoms, or alkoxycarbonyl having 1 to 4 carbon atoms, phenyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms, a five- or six-membered, saturated or unsaturated heterocyclic ring containing up to two hetero atoms optionally substituted by alkyl having 1 to 4 carbon atoms, biphenyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms, or diphenylmethyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms, provided that compounds wherein —K—L—M represents —H, are excluded.

4. The compound according to claim 3, wherein

A represents group —CR$^1$R$^2$(CH$_2$)$_i$— wherein R$^1$ and R$^2$ each represent a hydrogen atom and i is an integer of 1;

B represents a hydrogen or halogen atom;

X represents —CR$^3$R$^4$R$^5$ wherein R$^3$, R$^4$, and R$^5$, which may be the same or different, each represent a hydrogen atom or phenyl, provided that any one of R$^3$, R$^4$, and R$^5$ represents phenyl and one or more hydrogen atoms on phenyl may be substituted by a halogen atom, hydroxyl, nitro, phenyl, or alkoxy having 1 to 6 carbon atoms, —(CH$_2$—CH=C(CH$_3$)—CH$_2$)$_p$—CH$_2$CH=C(CH$_3$)$_2$ wherein p is an integer of 0 to 2, alkyl having 1 to 18 carbon atoms, cycloalkyl having 3 to 8 carbon atoms, phenyl optionally substituted by hydroxy, a halogen atom, nitro, alkoxy having 1 to 6 carbon atoms, or phenyl, or cinnamyl optionally substituted by hydroxy, a halogen atom, nitro, phenyl, or alkoxy having 1 to 6 carbon atoms;

Y represents —(CH$_2$)$_q$— wherein q is an integer of 1 to 6, or a bond;

Z represents a bond;

K represents alkylene having 1 to 6 carbon atoms optionally substituted by hydroxy, a halogen atom, alkyl having 1 to 6 carbon atoms, or alkoxy having 1 to 6 carbon atoms, or represents a bond;

L represents —CH=CH— or a bond; and

M represents a hydrogen atom, alkyl having 1 to 6 carbon atoms optionally substituted by hydroxy, a halogen atom, amino, alkoxy having 1 to 6 carbon atoms, or alkoxycarbonyl having 1 to 4 carbon atoms, cycloalkyl having 3 to 8 carbon atoms optionally substituted by hydroxy, a halogen atom, amino, alkoxy having 1 to 6 carbon atoms, alkylcarbonyloxy having 1 to 4 carbon atoms, or alkoxycarbonyl having 1 to 4 carbon atoms, phenyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms, a five- or six-membered, saturated or unsaturated heterocyclic ring containing up to two hetero atoms optionally substituted by alkyl having 1 to 4 carbon atoms, biphenyl optionally substituted by alkyl having 1 to 4 carbon atoms, trifluoromethyl, nitro, hydroxy, a halogen atom, amino, alkoxy having 1 to 4 carbon atoms, alkylcarbonyl 1 to 4 carbon atoms, or alkoxycarbonyl having 1 to 4 carbon atoms, or diphenylmethyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms.

5. The compound according to claim 3, wherein

A represents group —CR$^1$R$^2$—(CH$_2$)$_i$— wherein R$^1$ and R$^2$, which may be the same or different, represent a hydrogen atom or alkyl having 1 to 6 carbon atoms and i is an integer of 1,

—CH=CH—,

—O—CH$_2$—, or

—S(O)$_j$—CH$_2$— wherein j is an integer of 0 to 2;

B represents a hydrogen or halogen atom;

X represents —CR$^3$R$^4$R$^5$ wherein R$^3$, R$^4$, and R$^5$, which may be the same or different, each represent a hydrogen atom or phenyl, provided that any one of R$^3$, R$^4$, and R$^5$ represents phenyl and one or more hydrogen atoms on phenyl may be substituted by a halogen atom, hydroxyl, nitro, phenyl, or alkoxy having 1 to 6 carbon atoms, or —(CH$_2$—CH=C(CH$_3$)—CH$_2$)$_p$—CH$_2$CH=C(CH$_3$)$_2$ wherein p is an integer of 0 to 2;

Y represents —(CH$_2$)$_q$— wherein q is an integer of 1 to 6, or a bond;

Z represents a bond;

K represents alkylene having 1 to 6 carbon atoms optionally substituted by hydroxy, a halogen atom, alkyl having 1 to 6 carbon atoms, or alkoxy having 1 to 6 carbon atoms, or represents a bond;

L represents —CH=CH— or a bond; and

M represents a hydrogen atom, alkyl having 1 to 6 carbon atoms optionally substituted by hydroxy, a halogen atom, amino, alkoxy having 1 to 6 carbon atoms, or alkoxycarbonyl having 1 to 6 carbon atoms, cycloalkyl having 3 to 8 carbon atoms optionally substituted by hydroxy, a halogen atom, amino, alkoxy having 1 to 6 carbon atoms, alkylcarbonyloxy having 1 to 4 carbon atoms, or alkoxycarbonyl having 1 to 4 carbon atoms, phenyl optionally substituted by alkyl, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms, a five- or six-membered, saturated or unsaturated heterocyclic ring containing up to two hetero atoms optionally substituted by alkyl having 1 to 4 carbon atoms, biphenyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms, or diphenylmethyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms.

6. The compound according to claim 3, wherein

A represents group —$CR^1R^2$—$(CH_2)_i$— wherein $R^1$ and $R^2$, which may be the same or different, represent a hydrogen atom or alkyl having 1 to 6 carbon atoms and i is an integer of 1,

—CH=CH—,

—O—$CH_2$—, or

—S(O)$_j$—$CH_2$— wherein j is an integer of 0 to 2;

B represents a hydrogen or halogen atom;

X represents —$CR^3R^4R^5$ wherein $R^3$, $R^4$, and $R^5$, which may be the same or different, each represent a hydrogen atom or phenyl, provided that any one of $R^3$, $R^4$, and $R^5$ represents phenyl and one or more hydrogen atoms on phenyl may be substituted by a halogen atom, hydroxyl, nitro, phenyl, or alkoxy having 1 to 6 carbon atoms, —$(CH_2$—CH=$C(CH_3)$—$CH_2)_p$—$CH_2CH$=$C(CH_3)_2$ wherein p is an integer of 0 to 2, alkyl having 1 to 18 carbon atoms, cycloalkyl having 3 to 8 carbon atoms, phenyl optionally substituted by hydroxy, a halogen atom, nitro, alkoxy having 1 to 6 carbon atoms, or phenyl, or cinnamyl optionally substituted by hydroxy, a halogen atom, nitro, phenyl, or alkoxy having 1 to 6 carbon atoms;

Y represents —$(CH_2)_q$— wherein q is an integer of 1 to 6, or a bond;

Z represents a bond;

K represents alkylene having 1 to 3 carbon atoms optionally substituted by hydroxy, a halogen atom, alkyl having 1 to 6 carbon atoms, or alkoxy having 1 to 6 carbon atoms, or represents a bond;

L represents —CH=CH— or a bond; and

M represents a hydrogen atom, cycloalkyl having 3 to 8 carbon optionally substituted by hydroxy, a halogen atom, amino, alkoxy having 1 to 6 carbon atoms, alkylcarbonyloxy having 1 to 4 carbon atoms, or alkoxycarbonyl having 1 to 4 carbon atoms, phenyl optionally substituted by alkyl having 1 to 4 carbon atoms, trifluoromethyl, nitro, hydroxy, a halogen atom, amino, alkoxy having 1 to 4 carbon atoms, alkylcarbonyl having 1 to 4 carbon atoms, or alkoxycarbonyl having 1 to 4 carbon atoms, or a five- or six-membered, saturated or unsaturated heterocyclic ring containing up to two hetero atoms optionally substituted by alkyl having 1 to 4 carbon atoms.

7. The compound or salt thereof according to claim 3, which is 2-benzyl-7-[4-(3,3-diphenyl-1-propyl)piperazin-1-yl]-3,4-dihydro-2H-isoquinolin-1-one, 2-(4-chlorobenzyl)-7-[4-(3,3-diphenyl-1-propyl)-piperazin-1-yl]-3,4-dihydro-2H-isoquinolin-1-one, 7-[4-(3,3-diphenyl-1-propyl)piperazin-1-yl]-2-(3-methylbenzyl)-3,4-dihydro-2H-isoquinolin-1-one, 7-[4-(3,3-diphenyl-1-propyl)piperazin-1-yl]-2-(3-methoxybenzyl)-3,4-dihydro-2H-isoquinolin-1-one, 7-[4-(3,3-diphenyl-1-propyl)piperazin-1-yl]-2-(3-hydroxybenzyl)-3,4-dihydro-2H-isoquinolin-1-one, or 7-[4-(3,3-diphenyl-1-propyl)piperazin-1-yl]-2-(4-thiazolylmethyl)-3,4-dihydro-2H-isoquinolin-1-one.

8. A pharmaceutical composition comprising an effective amount of the compound or a pharmacologically acceptable salt or solvate thereof according to any one of claims 1 to 7 and a pharmacologically acceptable carrier.

9. A method for treating hyperlipidemia, comprising administering an effective amount of the compound and pharmacologically acceptable salt and solvate thereof according to any one of claims 1 to 7 to animals including human beings.

10. A method for treating arteriosclerotic diseases, comprising administering an effective amount of the compound and pharmacologically acceptable salt and solvate thereof according to any one of claims 1 to 7 to animals including human beings.

11. A method for treating pancreatitis, comprising administering an effective amount of the compound and pharmacologically acceptable salt and solvate thereof according to any one of claims 1 to 7 to animals including human beings.

* * * * *